United States Patent
Adams et al.

(10) Patent No.: US 7,217,710 B2
(45) Date of Patent: May 15, 2007

(54) SUBSTITUTED PYRAZOLOPYRIMIDINES

(75) Inventors: Jerry Leroy Adams, King of Prussia, PA (US); Jiri Kasparec, King of Prussia, PA (US); Domingos J. Silva, Collegeville, PA (US); Catherine C. K. Yuan, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 439 days.

(21) Appl. No.: 10/491,711

(22) PCT Filed: Oct. 1, 2002

(86) PCT No.: PCT/US02/31293

§ 371 (c)(1),
(2), (4) Date: Apr. 2, 2004

(87) PCT Pub. No.: WO03/029209

PCT Pub. Date: Apr. 10, 2003

(65) Prior Publication Data

US 2004/0198751 A1    Oct. 7, 2004

Related U.S. Application Data

(60) Provisional application No. 60/326,506, filed on Oct. 2, 2001.

(51) Int. Cl.
*A61K 31/5355* (2006.01)
*A61K 31/519* (2006.01)
*C07D 487/04* (2006.01)
*C07D 413/12* (2006.01)
*A61P 35/04* (2006.01)

(52) U.S. Cl. .................... 514/234.2; 544/262; 544/118; 514/265.1

(58) Field of Classification Search ................ 544/262, 544/118; 514/265.1, 234.2
See application file for complete search history.

(56) References Cited

U.S. PATENT DOCUMENTS 5,593,997 A    1/1997    Dow et al.

FOREIGN PATENT DOCUMENTS

WO    WO 98/14449    4/1998

*Primary Examiner*—Mark L. Berch
*Assistant Examiner*—Susanna Moore
(74) *Attorney, Agent, or Firm*—John L. Lemanowicz; James C. Kellerman; Loretta J. Sauermelch

(57) ABSTRACT

Pyrazolo-pyrimidine derivatives are described herein. The described invention also includes methods of making such derivatives as well as methods of using the same in the treatment of diseases.

4 Claims, No Drawings

SUBSTITUTED PYRAZOLOPYRIMIDINES

CROSS REFERENCES TO RELATED APPLICATIONS

This application is a National Stage Application filed under 35 U.S.C. § 371 of PCT/US02/31293, filed on Oct. 1, 2002, which claims priority of U.S. Provisional Application No. 60/326,506, filed Oct. 2, 2001.

BACKGROUND OF THE INVENTION

The present invention relates to pyrazolo[3,4-d]pyrimidine derivatives, compositions and medicaments containing the same, as well as processes for the preparation and use of such compounds, compositions and medicaments. Such pyrazolo[3,4-d]pyrimidine derivatives are useful in the treatment of diseases associated with inappropriate angiogenesis.

The process of angiogenesis is the development of new blood vessels, generally capillaries, from pre-existing vasculature. Angiogenesis is defined as involving: (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels. Normal angiogenesis is activated during tissue growth, from embryonic development through maturity, and then enters a period of relative quiescence during adulthood. Normal angiogenesis is also activated during wound healing, and at certain stages of the female reproductive cycle. Inappropriate angiogenesis has been associated with several disease states including various retinopathies; ischemic disease; atherosclerosis; chronic inflammatory disorders; and cancer. The role of angiogenesis in disease states is discussed, for instance, in Fan et al., Trends in Pharmacol. Sci. 16: 54–66; Shawver et al., DDT Vol. 2, No. 2 February 1997; Folkmann, 1995, Nature Medicine 1: 27–31; Colville-Nash and Scott, *Ann. Rheum. Dis.*, 51, 919, 1992; Brooks et al., *Cell*, 79, 1157, 1994; Kahlon et al., *Can. J. Cardiol.* 8, 60, 1992; Folkman, *Cancer Biol*, 3, 65, 1992; Denekamp, *Br. J. Rad.* 66, 181, 1993; Fidler and Ellis, *Cell*, 79, 185, 1994; O'Reilly et al., *Cell*, 79, 315, 1994; Ingber et al., *Nature*, 348, 555, 1990; Friedlander et al., Science, 270, 1500, 1995; Peacock et al., *J. Exp. Med.* 175, 1135, 1992; Peacock et al., *Cell. Immun.* 160, 178, 1995; and Taraboletti et al., *J. Natl. Cancer Inst.* 87, 293, 1995.

In cancer the growth of solid tumors has been shown to be angiogenesis dependent. (See Folkmann, J., J. Nat'l. Cancer Inst., 1990, 82, 4–6.) Consequently, the targeting of pro-angiogenic pathways is a strategy being widely pursued in order to provide new therapeutics in these areas of great, unmet medical need. The role of tyrosine kinases involved in angiogenesis and in the vascularization of solid tumors has drawn interest. Until recently most interest in this area has focused on growth factors such as vascular endothelial growth factor (VEGF) and its receptors termed vascular endothelial growth factor receptor(s) (VEGFR). VEGF, a polypeptide, is mitogenic for endothelial cells in vitro and stimulates angiogenic responses in vivo. VEGF has also been linked to inappropriate angiogenesis (Pinedo, H. M. et al. The Oncologist, Vol. 5, No. 90001, 1–2, April 2000). VEGFR(s) are protein tyrosine kinases (PTKs). PTKs catalyze the phosphorylation of specific tyrosyl residues in proteins involved in the regulation of cell growth and differentiation. (A. F. Wilks, Progress in Growth Factor Research, 1990, 2, 97–111; S. A. Courtneidge, Dev. Supp. 1, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. et al. J. Cell Biol. 1995, 129: 895–898). Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3–10, April 2000).

Angiopoieten 1 (Ang1), a ligand for the endothelium-specific receptor tyrosine kinase TIE-2 is a novel angiogenic factor (Davis et al., Cell, 1996, 87: 1161–1169; Partanen et al., Mol. Cell Biol., 12: 1698–1707 (1992); U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (Partanen et al., Curr. Topics Microbiol. Immunol., 1999, 237: 159–172). Unlike VEGF, which functions during the early stages of vascular development, Ang1 and its receptor TIE-2 function in the later stages of vascular development, i.e., during vascular remodeling (remodeling refers to formation of a vascular lumen) and maturation (Yancopoulos et al., Cell, 1998, 93: 661–664; Peters, K. G., Circ. Res., 1998, 83(3): 342–3; Suri et al., Cell 87, 1996: 1171–1180).

Consequently, inhibition of TIE-2 would be expected to serve to disrupt remodeling and maturation of new vasculature initiated by angiogenesis thereby disrupting the angiogenic process. Furthermore, inhibition at the kinase domain binding site of VEGFR-2 would block phosphorylation of tyrosine residues and serve to disrupt initiation of angiogenesis. Presumably then, inhibition of TIE-2 and/or VEGFR-2 should prevent tumor angiogenesis and serve to retard or eradicate tumor growth. Accordingly, a treatment for cancer or other disorder associated with inappropriate angiogenesis could be provided.

The present inventors have discovered novel pyrazolo[3,4-d]pyrimidine compounds, which are inhibitors of one or more of TIE-2 kinase activity, VEGFR-2 kinase activity, and VEGFR-3 kinase activity, e.g., one or both TIE-2 kinase and VEGFR-2 kinase activity. Such pyrazolo[3,4-d] pyrimidine derivatives are useful in the treatment of disorders, mediated by at least one of inappropriate TIE-2 kinase, VEGFR-2 kinase, and VEGFR-3 activity (which may include cancer and/or diseases afflicting mammals which is characterized by cellular proliferation in the area of disorders associated with neo-vascularization and/or vascular permeability), and/or disorders characterized by inappropriate angiogenesis; and/or for treating cancer and/or a disease afflicting afflicting mammals which is characterized by cellular proliferation in the area of disorders associated with neo-vascularization and/or vascular permeability.

BRIEF SUMMARY OF THE INVENTION

In one aspect of the present invention, there is provided a compound of formula (I):

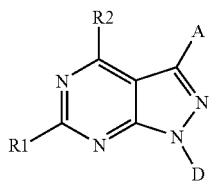

(I)

wherein:

A is hydrogen, halo, $C_1$–$C_6$ alkyl, aryl, heteroaryl (including aryl and heteroaryl substituted with at least one independently selected $R^3$ group and optionally further substituted), heterocyclyl, —$RR^3$, —C(O)O$R^4$, —C(O)N$R^5R^6$, or —C(O)$R^4$;

D is hydrogen, $C_1$–$C_6$ alkyl, aryl, heteroaryl (including aryl and heteroaryl substituted with at least one independently selected $R^3$ group and optionally further substituted), heterocyclyl, —$RR^3$, —C(O)O$R^4$, —C(O)N$R^5R^6$, or —C(O)$R^4$;

R is independently selected from $C_1$–$C_6$ alkylene, $C_2$–$C_6$ alkenylene, or $C_2$–$C_6$ alkynylene;

$R^1$ is hydrogen, $C_1$–$C_6$ alkyl, $C_1$–$C_6$ alkoxy, —SR, —S(O)R, —S(O)$_2$R, —N$R^7R^7$, —N$R^{10}$N$R^{12}R^{13}$, —N$R^7$($R^{10}$N$R^{12}R^{13}$), —C(O)O$R^7$, or —C(O)N$R^7R^7$, with the proviso that, when $R^2$ is —N$R^7R^7$, $R^1$ is $C_1$–$C_6$ alkyl, $C_1$–$C_6$ alkoxy, —SR, —S(O)R, —S(O)$_2$R, —N$R^7R^7$, —N$R^{10}$N$R^{12}R^{13}$, —N$R^7$($R^{10}$N$R^{12}R^{13}$), —C(O)O$R^7$, or —C(O)N$R^7R^7$;

$R^2$ is H, —N$R^7R^7$ or =NH;

$R^3$ is independently selected from halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —NHC(O)$R^4$, —NH—C(=N—CN)$R^4$, —NHC(S)$R^4$, —N$R^5R^6$, —RN$R^5R^6$, —S$R^4$, —S(O)$R^4$, —S(O)$_2R^4$, —RC(O)O$R^4$, —C(O)O$R^4$, —C(O)$R^4$, —C(O)N$R^5R^6$,—NHS(O)$_2R^4$, —S(O)$_2$N$R^5R^6$, —NHC(=NH)$R^4$, and the structure:

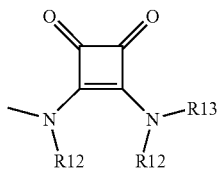

$R^4$ is independently selected from hydrogen, $C_1$–$C_6$ alkyl, aryl, heteroaryl, heterocyclyl, —$RR^3$, —N$R^{12}R^{13}$, —N$R^{10}$N$R^{12}R^{13}$ and —N$R^7$($R^{10}$N$R^{12}R^{13}$);

$R^5$ is independently selected from hydrogen, $C_1$–$C_6$ alkyl, $C_3$–$C_7$ cycloalkyl, cyanoalkyl, —$R^{10}R^{11}$, aryl, aralkyl, heteroaryl, —NHC(O)O$R^{12}$, —$R^{10}$NHC(O)O$R^{12}$, —$R^{10}$NHC(O)N$R^{12}R^{13}$, and —$R^{10}$C(O)O$R^{12}$;

$R^6$ is independently selected from hydrogen, $C_1$–$C_6$ alkyl, $C_3$–$C_7$ cycloalkyl, cyanoalkyl, —$R^{10}R^{11}$, aryl, aralkyl, heteroaryl, —C(O)O$R^{12}$, and —$R^{10}$C(O)N$R^{12}R^{12}$;

$R^7$ is independently selected from hydrogen, $C_1$–$C_6$ alkyl, aryl, —C(O)$R^4$, heterocyclyl, and —C(O)O$R^{12}$;

$R^{10}$ is independently selected from $C_1$–$C_4$ alkylene;

$R^{11}$ is independently selected from heteroalkyl or N$R^{12}R^{13}$;

$R^{12}$ is independently selected from hydrogen, $C_1$–$C_6$ alkyl, aryl, aralkyl, heteroaryl, or $C_3$–$C_7$ cycloalkyl; and $R^{13}$ is independently selected from hydrogen, $C_1$–$C_6$ alkyl, aryl, heteroaryl, or $C_3$–$C_7$ cycloalkyl;

or a salt, solvate, or physiologically functional derivative thereof

In a second aspect of the present invention, there is provided a compound of Formula (I) wherein A is aryl or heteroaryl (including aryl or heteroaryl substituted with at least one independently selected $R^3$ group), heterocyclyl, —$RR^3$, —C(O)O$R^4$, —C(O)N$R^5R^6$, or —C(O)$R^4$, and D, R, $R^1$, $R^2$, $R^3$, $R^4$, $R^5$, $R^6$, $R^7$, $R^{10}$, $R^{11}$, $R^{12}$ and $R^{13}$ are as defined above; or a salt, solvate, or physiologically functional derivative thereof.

In a third aspect of the present invention, there is provided a compound of Formula (I) wherein $R^2$ is H, and A, D, R, $R^1$, $R^3$, $R^4$, $R^5$, $R^6$, $R^7$, $R^{10}$, $R^{11}$, $R^{12}$ and $R^{13}$ are as defined above; or a salt, solvate, or physiologically functional derivative thereof. In such compounds, A is preferably aryl or heteroaryl (including aryl or heteroaryl substituted with at least one independently selected $R^3$ group), heterocyclyl, —$RR^3$, —C(O)O$R^4$, —C(O)N$R^5R^6$, or —C(O)$R^4$.

In a fourth aspect of the present invention, there is provided a compound of Formula (I) wherein $R^1$ is —N$R^7R^7$, —N$R^7$($R^{10}$N$R^{12}R^{13}$) or —N$R^{10}$N$R^{12}R^{13}$, and A, D, R, $R^2$, $R^3$, $R^4$, $R^5$, $R^6$, $R^7$, $R^{10}$, $R^{11}$, $R^{12}$ and $R^{13}$ are as defined above; or a salt, solvate, or physiologically functional derivative thereof. In such compounds A is preferably aryl or heteroaryl (including aryl or heteroaryl substituted with at least one independently selected $R^3$ group), heterocyclyl, —$RR^3$, —C(O)O$R^4$, —C(O)N$R^5R^6$, or —C(O)$R^4$, and $R^2$ is preferably H.

In the foregoing aspects, said A, D, R, $R^1$ to $R^7$ and $R^{10}$ to $R^{13}$ may be optionally substituted as valency permits, unless otherwise stated.

In a fifth aspect of the invention, there are provided compounds of Formula (I) wherein:

A is aryl or heteroaryl substituted with at least one —NHC(O)$R^8$, —NHS(O)$_2R^9$ or —NHC(S)$R^8$ group, which aryl and heteroaryl may optionally be further substituted;

D is hydrogen, $C_1$–$C_6$ alkyl, aryl, heteroaryl, heterocyclyl, —$RR^3$, —C(O)O$R^4$, —C(O)N$R^5R^6$, or —C(O)$R^4$, which alkyl, aryl, heteroaryl, and heterocyclyl may optionally be substituted;

R is independently selected from $C_1$–$C_6$ alkylene, $C_2$–$C_6$ alkenylene, or $C_2$–$C_6$ alkynylene;

$R^1$ is —N$R^7R^7$ or —N$R^7$($R^{10}$N$R^{12}R^{13}$);

$R^2$ is H, —N$R^7R^7$ or =NH;

$R^3$ is independently selected from halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —NHC(O)$R^4$, —NH—C(=N—CN)$R^4$, —NHC(S)

$R^4$, $-NR^5R^6$, $-RNR^5R^6$, $-SR^4$, $-S(O)R^4$, $-S(O)_2R^4$, $-RC(O)OR^4$, $-C(O)OR^4$, $-C(O)R^4$, $-C(O)NR^5R^6$, $-NHS(O)_2R^4$, $-S(O)_2NR^5R^6$, $-NHC(=NH)R^4$, and the structure:

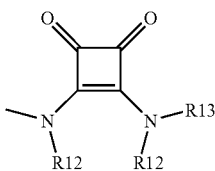

wherein the alkyl, haloalkyl, alkoxy, cycloalkoxy, haloalkoxy, aryl, aralkyl, aryloxy, heteroaryl and heterocyclyl may optionally be substituted;

$R^4$ is independently selected from hydrogen, $C_1$–$C_6$ alkyl, aryl, heteroaryl, heterocyclyl, $-RR^3$, $-NR^{12}R^{13}$, and $-NR^7(R^{10}NR^{12}R^{13})$, wherein the alkyl, aryl, heteroaryl, and heterocyclyl may optionally be substituted;

$R^5$ is independently selected from hydrogen, $C_1$–$C_6$ alkyl, $C_3$–$C_7$ cycloalkyl, cyanoalkyl, $-R^{10}R^{11}$, aryl, aralkyl, heteroaryl, $-NHC(O)OR^{12}$, $-R^{10}NHC(O)OR^{12}$, $-R^{10}NHC(O)NR^{12}R^{13}$, and $-R^{10}C(O)OR^{12}$, wherein the alkyl, cycloalkyl, cyanoalkyl, aryl, aralkyl, and heteroaryl may optionally be substituted;

$R^6$ is independently selected from hydrogen, $C_1$–$C_6$ alkyl, $C_3$–$C_7$ cycloalkyl, cyanoalkyl, $-R^{10}R^{11}$, aryl, aralkyl, heteroaryl, $-C(O)OR^{12}$, and $-R^{10}C(O)NR^{12}R^{12}$, wherein the alkyl, cycloalkyl, cyanoalkyl, aryl, aralkyl and heteroaryl may optionally be substituted;

$R^7$ is independently selected from hydrogen, $C_1$–$C_6$ alkyl, $-C(O)R^4$, aryl, heterocyclyl, and $-C(O)OR^{12}$, wherein the alkyl, aryl and heterocyclyl may optionally be substituted;

$R^8$ is independently selected from $-NR^{12}R^{13}$ or $-NR^7(R^{10}NR^{12}R^{13})$;

$R^9$ is independently selected from aryl or heteroaryl, which aryl and heteroaryl may optionally be substituted;

$R^{10}$ is independently selected from optionally substituted $C_1$–$C_4$ alkylene, preferably C2–C3 alkylene;

$R^{11}$ is independently selected from optionally substituted heteroalkyl and $NR^{12}R^{13}$;

$R^{12}$ is independently selected from hydrogen, $C_1$–$C_6$ alkyl, aryl, aralkyl, heteroaryl, and $C_3$–$C_7$ cycloalkyl, wherein the alkyl, aryl, aralkyl, heteroaryl and cycloalkyl may optionally be substituted; and $R^{13}$ is independently selected from hydrogen, $C_1$–$C_6$ alkyl, aryl, heteroaryl, and $C_3$–$C_7$ cycloalkyl, wherein the alkyl, aryl, heteroaryl, and cycloalkyl may optionally be substituted;

or a salt, solvate, or physiologically functional derivative thereof.

In a sixth aspect of the present invention, there is provided a pharmaceutical composition comprising a therapeutically effective amount of a compound of formula (I), or a salt, solvate, or a physiologically functional derivative thereof and one or more of pharmaceutically acceptable carriers, diluents and excipients.

In a seventh aspect of the present invention, there is provided a method of treating a disorder in a mammal, said disorder being mediated by at least one of inappropriate TIE-2, VEGFR-2, and VEGFR-3 kinase activity, comprising: administering to said mammal a therapeutically effective amount of a compound of formula (I) or a salt, solvate or a physiologically functional derivative thereof.

In a eighth aspect of the present invention, there is provided a compound of formula (I), or a salt, solvate, or a physiologically functional derivative thereof for use in therapy.

In an ninth aspect of the present invention, there is provided the use of a compound of formula (I), or a salt, solvate, or a physiologically functional derivative thereof in the preparation of a medicament for use in the treatment of a disorder mediated by at least one of inappropriate TIE-2, VEGFR-2, and VEGFR-3 kinase activity.

In a tenth aspect of the present invention, there is provided a method of treating a disorder in a mammal, said disorder being mediated by at least one of inappropriate TIE-2, VEGFR-2, and VEGFR-3 kinase activity, comprising: administering to said mammal therapeutically effective amounts of (i) a compound of formula (I), or a salt, solvate or physiologically functional derivative thereof and (ii) an agent to inhibit growth factor receptor function.

In a eleventh aspect of the present invention, there is provided a method of treating a disorder in a mammal, said disorder being characterized by inappropriate angiogenesis, comprising: administering to said mammal a therapeutically effective amount of a compound of formula (I), or a salt, solvate or physiologically functional derivative thereof.

Other aspects of the invention will be apparent from this disclosure.

DETAILED DESCRIPTION

All documents cited or referred to herein, including issued patents, published and unpublished patent applications, and other publications are hereby incorporated herein by reference as though fully set forth.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the numbering of the pyrazolo[3,4-d] pyrimidine scaffold in formula (I) is assigned as shown in the structure following.

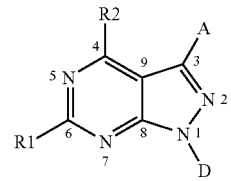

As used herein, the term "alkyl" refers to a straight or branched chain hydrocarbon radical having from one to twelve carbon atoms, optionally substituted with substituents selected from the group which includes $C_1$–$C_6$ alkyl, $C_1$–$C_6$ hydroxyalkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aryl, aryloxy, heteroaryl, aminosulfonyl optionally substituted by alkyl or aryl, nitro, cyano, halogen, or $C_1$–$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$–$C_6$ alkyl" refers to an alkyl group as defined above containing at least 1, and at most 6, carbon atoms. Examples of branched or straight chained "$C_1$–$C_6$ alkyl" groups useful in the present invention include, but are not limited to, methyl, ethyl, n-propyl, isopropyl, isobutyl, n-butyl, t-butyl, n-pentyl, and isopentyl.

As used herein, the term "alkylene" refers to a straight or branched chain divalent hydrocarbon radical having from one to ten carbon atoms, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkylene" as used herein include, but are not limited to, methylene, ethylene, n-propylene, n-butylene, and the like.

As used herein, the terms "$C_1$–$C_6$ alkylene" and "$C_1$–$C_3$ alkylene" refer to an alkylene group, as defined above, which contains at least 1, and, respectively, at most 6 or at most 3, carbon atoms. Examples of "$C_1$–$C_3$ alkylene" groups useful in the present invention include, but are not limited to, methylene, ethylene, and n-propylene.

As used herein, the term "alkenyl" refers to a straight or branched chain hydrocarbon radical having from two to ten carbons and at least one carbon-carbon double bond, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkenyl" as used herein include ethenyl, propenyl, 1-butenyl, 2-butenyl, and isobutenyl.

As used herein, the term "$C_2$–$C_6$ alkenyl" refers to an alkenyl group as defined above containing at least 2, and at most 6, carbon atoms. Examples of "$C_2$–$C_6$ alkenyl" groups useful in the present invention include, but are not limited to, ethenyl, propenyl, 1-butenyl, 2-butenyl, and isobutenyl.

As used herein, the term "alkenylene" refers to a straight or branched chain divalent hydrocarbon radical having from two to ten carbon atoms and one or more carbon-carbon double bonds, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the terms "$C_2$–$C_6$ alkenylene" and "$C_2$–$C_3$ alkenylene" refer to an alkenylene group as defined above containing at least 2, and, respectively, at most 6 or at most 3 carbon atoms. Examples of "$C_2$–$C_3$ alkenylene" groups useful in the present invention include, but are not limited to, ethene-1,2-diyl, propene-1,3-diyl, methylene-1,1-diyl, and the like.

As used herein, the term "alkynyl" refers to a straight or branched chain hydrocarbon radical having from two to ten carbons and at least one carbon-carbon triple bond, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, aryl, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkynyl" as used herein, include but are not limited to acetylenyl, 1-propynyl, 1-butynyl, 2-butynyl, 1-pentynyl, and 1-hexynyl.

As used herein, the term "alkynylene" refers to a straight or branched chain divalent hydrocarbon radical having from two to ten carbon atoms and one or more carbon-carbon triple bonds, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkynylene" as used herein include, but are not limited to, ethyne-1,2-diyl, propyne-1,3-diyl, and the like.

As used herein, the terms "$C_2$–$C_6$ alkynylene" and "$C_2$–$C_3$ alkynylene" refers to an alkynylene group as defined above containing at least 2, and, respectively, at most 6 carbon atoms or at most 3 carbon atoms. Examples of "$C_2$–$C_3$ alkynylene" groups useful in the present invention include, but are not limited to, ethyne-1,2-diyl, propyne-1,3-diyl, and the like.

As used herein, the term "halogen" refers to fluorine (F), chlorine (Cl), bromine (Br), or iodine (I) and the term "halo" refers to the halogen radicals fluoro, chloro, bromo, and iodo.

As used herein, the term "$C_1$–$C_6$ haloalkyl" refers to an alkyl group as defined above containing at least 1, and at most 6, carbon atoms substituted with at least one halo group, halo being as defined herein. Examples of branched or straight chained "$C_1$–$C_6$ haloalkyl" groups useful in the present invention include, but are not limited to, methyl, ethyl, propyl, isopropyl, isobutyl and n-butyl substituted independently with one or more halos, e.g., fluoro, chloro, bromo and iodo, e.g., trifluoromethyl.

As used herein, the term "$C_3$–$C_7$ cycloalkyl" refers to a non-aromatic cyclic hydrocarbon radical having from three to seven carbon atoms and which optionally includes a $C_1$–$C_6$ alkyl linker through which it may be attached, and which is optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen, $C_1$–$C_6$ perfluoroalkyl, multiple degrees of substitution being allowed. The $C_1$–$C_6$ alkyl group is as defined above. Exemplary "$C_3$–$C_7$ cycloalkyl" groups include, but are not limited to, cyclopropyl, cyclobutyl, cyclopentyl, cyclohexyl and cycloheptyl.

As used herein, the term "$C_3$–$C_7$ cycloalkylene" refers to a divalent non-aromatic cyclic hydrocarbon radical having from three to seven carbon atoms, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen, $C_1$–$C_6$ perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered ring containing one or more heteroatomic substitutions selected from S, SO, $SO_2$, O, N, or N-oxide, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen, or $C_1$–$C_6$ perfluoroalkyl, multiple degrees of substitution being allowed. Such a ring can be saturated or have one or more degrees of saturation. Such a ring may be optionally fused to one or more other optionally substituted, "heterocyclic" ring(s), aryl rings (including benzene rings), heteroaryl rings, or cycloalkyl ring(s). Examples of "heterocyclic" moieties include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to an unsaturated three to twelve-membered ring diradical containing one or more heteroatoms selected from S, SO, $SO_2$, O, N, or N-oxide, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Such a ring has one or more degrees of unsaturation. Such a ring may be optionally fused to one or more optionally substituted aryl rings (including benzene rings), heterocyclic rings, heteroaryl rings, or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to an optionally substituted benzene ring or to an optionally substituted benzene ring fused to one or more optionally substituted benzene rings to form a ring system. Exemplary optional substituents include $C_1$–$C_6$ alkyl, $C_1$–$C_6$ alkoxy, $C_1$–$C_6$ haloalkyl, $C_1$–$C_6$ haloalkoxy, $C_1$–$C_6$ alkylsulfanyl, $C_1$–$C_6$ alkylsulfenyl, $C_1$–$C_6$ alkylsulfonyl, $C_1$–$C_6$ alkylsulfonylamino, arylsulfonylamino, alkylcarboxy, alkylcarboxamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halogen, heteroaryl, heterocyclyl, aryl optionally substituted with aryl, halogen, $C_1$–$C_6$ alkyl, $C_1$–$C_6$ haloalkyl, or $C_1$–$C_6$ alkylsulfonyl, ureido, arylurea, alkylurea, cycloalkylurea, alkylthiourea, aryloxy, or aralkoxy, multiple degrees of substitution being allowed. Such a ring or ring system may be optionally fused to one or more optionally substituted aryl rings (including benzene rings) or cycloalkyl rings. Examples of "aryl" groups include, but are not limited to, phenyl, 2-naphthyl, tetrahydronaphthyl, 1-naphthyl, biphenyl, indanyl, anthracyl, phenanthryl, or napthyl, as well as substituted derivatives thereof.

As used herein, the term "arylene" refers to an optionally substituted benzene ring diradical or to a benzene ring system diradical containing an optionally substituted benzene ring fused to one or more optionally substituted benzene rings. Exemplary optional substituents are selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, tetrazolyl, carbamoyl optionally substituted by alkyl or aryl, aminosulfonyl optionally substituted by alkyl or aryl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl and aryl, multiple degrees of substitution being allowed. Such a ring or ring system may be optionally fused to one or more optionally substituted aryl rings (including benzene rings), or cycloalkyl rings. Examples of "arylene" include, but are not limited to, benzene-1,4-diyl, naphthalene-1,8-diyl, anthracene-1,4-diyl, and the like.

As used herein, the term "aralkyl" refers to an aryl or heteroaryl group, as defined herein, attached through a $C_1$–$C_3$ alkylene linker, wherein the $C_1$–$C_3$ alkylene is as defined herein. Examples of "aralkyl" include, but are not limited to, benzyl, phenylpropyl, 2-pyridylmethyl, 3-isoxazolylmethyl, 3-(1-methyl-5-t-butyl-pyrazyl)methyl, 3-isoxazolylmethyl, and 2-imidazolyl ethyl.

As used herein, the term "heteroaryl" refers to an optionally substituted monocyclic five to seven membered aromatic ring containing one or more heteroatomic substitutions selected from S, SO, $SO_2$, O, N, or N-oxide, or to such an aromatic ring fused to one or more, optionally substituted, such heteroaryl rings, aryl rings (including benzene rings), heterocyclic rings, or cycloalkyl rings (e.g., a bicyclic or tricyclic ring system). Examples of optional substituents are selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, tetrazolyl, carbamoyl optionally substituted by alkyl or aryl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl, or aryl, multiple degrees of substitution being allowed. Examples of "heteroaryl" groups used herein include, but are not limited to, furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "heteroarylene" refers to a five- to seven-membered monocyclic aromatic diradical, or to a polycyclic aromatic diradical, containing one or more heteroatomic substitutions selected from S, SO, $SO_2$, O, N, or N-oxide, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, tetrazolyl, carbamoyl optionally substituted by alkyl or aryl, aminosulfonyl optionally substituted by alkyl or aryl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl, or aryl, multiple degrees of substitution being allowed. For polycyclic aromatic system diradicals, one or more of the rings may contain one or more heteroatoms, and one or more of the rings may be aryl, heterocyclic, heteroaryl, or cycloalkyl. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is alkyl as defined above and the term "$C_1$–$C_6$ alkoxy" refers to an alkoxy group as defined herein wherein the alkyl moiety contains at least 1, and at most 6, carbon atoms. Exemplary $C_1$–$C_6$ alkoxy groups useful in the present invention include, but are not limited to, methoxy, ethoxy, n-propoxy, isopropoxy, n-butoxy, and t-butoxy.

As used herein the term "aralkoxy" refers to the group $R_bR_aO$—, where $R_a$ is alkyl and $R_b$ is aryl as defined above.

As used herein the term "aryloxy" refers to the group $R_aO$—, where $R_a$ is aryl as defined above.

As used herein the term "ureido" refers to the group —NHC(O)NH$_2$.

As used herein, the term "arylurea" refers to the group —NHC(O)NHR$_a$ wherein $R_a$ is aryl as defined above.

As used herein, the term "arylthiourea" refers to the group —NHC(S)NHR$_a$ wherein $R_a$ is aryl as defined above.

As used herein, the term "alkylurea" refers to the group —NHC(O)NHR$_a$ wherein $R_a$ is alkyl as defined above.

As used herein, the term "cycloalkylurea" refers to the group —NHC(O)NHR$_a$ wherein $R_a$ is cycloalkyl as defined above.

As used herein, the term "$C_3$-$C_7$ cycloalkoxy" refers to the group $R_aO$—, where $R_a$ is $C_3$–$C_7$ cycloalkyl as defined above. Exemplary $C_3$–$C_7$ cycloalkoxy groups useful in the present invention include, but are not limited to cyclopropoxy, cyclobutoxy, and cyclopentoxy.

As used herein, the term "haloalkoxy" refers to the group $R_aO$—, where $R_a$ is haloalkyl as defined above and the term "$C_1$–$C_6$ haloalkoxy" refers to a haloalkoxy group as defined herein wherein the haloalkyl moiety contains at least 1, and at most 6, carbon atoms. Exemplary $C_1$–$C_6$ haloalkoxy groups useful in the present invention include, but is not limited to, trifluoromethoxy.

As used herein, the term "alkylsulfanyl" refers to the group $R_aS$—, where $R_a$ is alkyl as defined above and the term "$C_1$–$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group $R_aS$—, where $R_a$ is haloalkyl as defined above and the term "$C_1$–$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$–$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$–$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —NHS(O)$_2$R$_a$ wherein $R_a$ is alkyl as defined above and the term "$C_1$–$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —NHS(O)$_2$R$_a$ wherein $R_a$ is aryl as defined above.

As used herein, the term "alkylcarboxyamide" refers to the group —NHC(O)R$_a$ wherein $R_a$ is alkyl, amino, or amino substituted with alkyl, aryl or heteroaryl as described above.

As used herein the term "alkylcarboxy" refers to the group —C(O)R$_a$ wherein $R_a$ is alkyl as described above.

As used herein, the term "oxo" refers to the group =O.

As used herein, the term "mercapto" refers to the group —SH.

As used herein, the term "carboxy" refers to the group —C(O)OH.

As used herein, the term "cyano" refers to the group —CN.

As used herein the term "cyanoalkyl" refers to the group —R$_a$CN, wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —S(O)$_2$NH$_2$.

As used herein, the term "carbamoyl" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "aroylamino" refers to the group $R_aC(O)NH$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s) which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers of the compounds of formula (I) are included within the scope of the compounds of formula (I).

It is to be understood that reference to compounds of formula (I) herein refers to all compounds within the scope of formula (I) as defined above with respect to A, D, R, $R^1$, $R^2$, $R^3$, $R^4$, $R^5$, $R^6$, $R^7$, $R^{10}$, $R^{11}$, $R^{12}$, or $R^{13}$ unless specifically limited otherwise.

Preferred embodiments of the present invention are compounds having Formula (I):

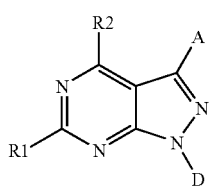

(I)

wherein:

A is aryl or heteroaryl substituted with at least one $-NHC(O)R^8$, $-NHS(O)_2R^9$ or $-NHC(S)R^8$ group, which aryl and heteroaryl may optionally be further substituted;

D is hydrogen, $C_1$–$C_6$ alkyl, aryl, heteroaryl, heterocyclyl, $-RR^3$, $-C(O)OR^4$, $-C(O)NR^5R^6$, or $-C(O)R^4$, which alkyl, aryl, heteroaryl, and heterocyclyl may optionally be substituted;

R is independently selected from $C_1$–$C_6$ alkylene, $C_2$–$C_6$ alkenylene, or $C_2$–$C_6$ alkynylene;

$R^1$ is $-NR^7R^7$ or $-NR^7(R^{10}NR^{12}R^{13})$;

$R^2$ is H, $-NR^7R^7$ or $=NH$;

$R^3$ is independently selected from halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, $-CN$, $-NHC(O)R^4$, $-NH-C(=N-CN)R^4$, $-NHC(S)R^4$, $-NR^5R^6$, $-RNR^5R^6$, $-SR^4$, $-S(O)R^4$, $-S(O)_2R^4$, $-RC(O)OR^4$, $-C(O)OR^4$, $-C(O)R^4$, $-C(O)NR^5R^6$, $-NHS(O)_2R^4$, $-S(O)_2NR^5R^6$, $-NHC(=NH)R^4$, and the structure:

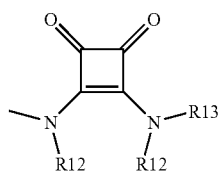

wherein the alkyl, haloalkyl, alkoxy, cycloalkoxy, haloalkoxy, aryl, aralkyl, aryloxy, heteroaryl and heterocyclyl may optionally be substituted;

$R^4$ is independently selected from hydrogen, $C_1$–$C_6$ alkyl, aryl, heteroaryl, heterocyclyl, $-RR^3$, $-NR^{12}R^{13}$, and $-NR^7(R^{10}NR^{12}R^{13})$, wherein the alkyl, aryl, heteroaryl, and heterocyclyl may optionally be substituted;

$R^5$ is independently selected from hydrogen, $C_1$–$C_6$ alkyl, $C_3$–$C_7$ cycloalkyl, cyanoalkyl, $-R^{10}R^{11}$, aryl, aralkyl, heteroaryl, $-NHC(O)OR^{12}$, $-R^{10}NHC(O)OR^{12}$, $-R^{10}NHC(O)NR^{12}R^{13}$, and $-R^{10}C(O)OR^{12}$, wherein the alkyl, cycloalkyl, cyanoalkyl, aryl, aralkyl, and heteroaryl may optionally be substituted;

$R^6$ is independently selected from hydrogen, $C_1$–$C_6$ alkyl, $C_3$–$C_7$ cycloalkyl, cyanoalkyl, $-R^{10}R^{11}$, aryl, aralkyl, heteroaryl, $-C(O)OR^{12}$, and $-R^{10}C(O)NR^{12}R^{12}$, wherein the alkyl, cycloalkyl, cyanoalkyl, aryl, aralkyl and heteroaryl may optionally be substituted;

$R^7$ is independently selected from hydrogen, $C_1$–$C_6$ alkyl, $-C(O)R^4$, aryl, heterocyclyl, and $-C(O)OR^{12}$, wherein the alkyl, aryl and heterocyclyl may optionally be substituted;

$R^8$ is independently selected from $-NR^{12}R^{13}$ or $-NR^7(R^{10}NR^{12}R^{13})$;

$R^9$ is independently selected from aryl or heteroaryl, which aryl and heteroaryl may optionally be substituted;

$R^{10}$ is independently selected from optionally substituted $C_1$–$C_4$ alkylene;

$R^{11}$ is independently selected from optionally substituted heteroalkyl and $-NR^{12}R^{13}$;

$R^{12}$ is independently selected from hydrogen, $C_1$–$C_6$ alkyl, aryl, aralkyl, heteroaryl, and $C_3$–$C_7$ cycloalkyl, wherein the alkyl, aryl, aralkyl, heteroaryl and cycloalkyl may optionally be substituted; and $R^{13}$ is independently selected from hydrogen, $C_1$–$C_6$ alkyl, aryl, heteroaryl, and $C_3$–$C_7$ cycloalkyl, wherein the alkyl, aryl, heteroaryl, and cycloalkyl may optionally be substituted;

or a salt, solvate, or physiologically functional derivative thereof.

In particularly preferred embodiments the compound is a compound of formula (I), wherein:

A is aryl, preferably phenyl, substituted with at least one $-NHC(O)R^8$, $-NHS(O)_2R^9$ or $-NHC(S)R^8$ group (preferably in the para-position), which aryl may optionally be further substituted;

D is $C_1$–$C_6$ alkyl or $-RR^3$, wherein R is $C_1$–$C_6$ alkylene and $R^3$ is aryl, preferably $C_1$–$C_3$ alkyl or benzyl;

R¹ is —NR⁷R⁷, wherein one of R⁷ is H and the other is selected from: optionally substituted $C_1$–$C_6$ alkyl, optionally substituted phenyl, —C(O)R⁴, wherein R⁴ is $C_1$–$C_6$ alkyl (especially $C_1$–$C_3$ alkyl); and heterocyclyl; and R² is H;

or a salt, solvate, or physiologically functional derivative thereof.

In one particularly preferred embodiment, the compounds of formula (I) are ureas wherein:
   A is phenyl para-substituted with —NHC(O)R⁸ and optionally further substituted;
   R⁸ is —NHR¹³;
   R¹³ is aryl or heteroaryl, which aryl and heteroaryl may be optionally substituted;
   D is $C_1$–$C_6$ alkyl or aralkyl;
   R¹ is NHR⁷;
   R⁷ is $C_1$–$C_6$ alkyl substituted by one or more heterocyclyl, $C_1$–$C_6$ alkoxy, hydroxy, —NR⁵R⁶ wherein R⁵ and R⁶ are independently H or $C_1$–$C_6$ alkyl, aryl, —NHS(O)₂R⁴, —NHC(O)R⁴, or —NHC(=NH)R⁴ wherein R⁴ is selected from $C_1$–$C_6$ alkyl and H; optionally substituted phenyl; —C(O)R⁴ wherein R⁴ is $C_1$–$C_6$ alkyl (especially $C_1$–$C_3$ alkyl); or heterocyclyl; wherein any of said heterocyclyl, alkoxy, alkyl, and aryl may be optionally substituted; and
   R² is H;

or a salt, solvate, or physiologically functional derivative thereof.

Such urea compounds include those wherein:
   in moiety A, optional substituent groups are one or more groups, preferably one group, selected from $C_1$–$C_6$ alkyl, halo, and trifluoromethyl, e.g., methyl, fluoro, trifluoromethyl;
   R¹³ is phenyl optionally substituted, preferably mono- or disubstituted, with halo, trifluoromethyl, $C_1$–$C_6$ alkyl, C(O)R⁴ wherein R⁴ is $C_1$–$C_6$ alkyl (e.g., fluoro, chloro, trifluoromethyl, ethyl, acetyl); isoxazol-3-yl; or naphthyl;
   D is methyl, isopropyl, or benzyl;
   R⁷ is hydroxy ethyl, 5-hydroxy pentyl, 3-hydroxypropyl, 4-hydroxybutyl, 2-hydroxy-1-hydroxymethyl-ethyl, 2-((fluoro-trifluoromethyl-phenyl)-carbamic acid)ethyl, 2-oxopyrrolidin-2-yl-propyl, 3-(4-methyl-piperazine-1-yl)propyl, 3-(2-methyl-piperadin-1-yl)propyl, (3-pyrrolidin-1-yl)propyl, (4-pyrrolidin-1-yl)butyl 2-(1-methyl-pyrrolidin-2-yl)ethyl, 1-methyl-1H-pyrrol-2yl-ethyl, (2-oxoimidazolidin-1-yl)ethyl, 3-imidazol-1-yl-propyl, 2-(1H-imidazol-4-yl)ethyl, 2-(3-methyl-3H-imidazol-4yl)ethyl, 3-morpholin-4yl-propyl, 2-morpholin-4-yl-ethyl, 2-pyridin-4-yl-ethyl, 2-pyridin-3-yl-ethyl, 2-pyridin-2-yl-ethyl, pyridin-4-yl-methyl, pyridin-3yl-methyl, 2-methoxy-ethyl, 2-diethylamino-ethyl, 4-diethylamino-butyl, 3-dimethylamino-propyl, 3-diethylamino-propyl, 3-aminopropyl, 4-aminobutyl, (1-methyl-piperidin-4-yl), acetyl, benzyl, 2-phenyl ethyl, 3-chlorophenyl, propyl methane sulfonamide, butyl methane sulfonamide, 2-acetylamino-ethyl or 4-guanidino-butyl.

In another particularly preferred embodiment, the compounds of formula (I) are sulfonamides wherein:
   A is phenyl para-substituted with —NHS(O)₂R⁹ and optionally further substituted;
   R⁹ is phenyl or thiophene, which phenyl and thiophene may be optionally substituted;
   D is $C_1$–$C_6$ alkyl;
   R¹ is —NHR⁷;
   R⁷ is: $C_1$–$C_6$ alkyl substituted by one or more heterocyclyl, $C_1$–$C_6$ alkoxy, hydroxy, —NR⁵R⁶ wherein R⁵ and R⁶ are independently H or $C_1$–$C_6$ alkyl, aryl, —NHS(O)₂R⁴, —NHC(O)R⁴, or —NHC(=NH)R⁴ wherein R⁴ is selected from $C_1$–$C_6$ alkyl and H; optionally substituted phenyl; —C(O)R⁴ wherein R⁴ is $C_1$–$C_6$ alkyl (especially $C_1$–$C_3$ alkyl); or heterocyclyl; especially $C_1$–$C_6$ alkyl substituted by one or more heterocyclyl, hydroxy, —NR⁵R⁶ wherein R⁵ and R⁶ are independently H or $C_1$–$C_6$ alkyl, —NHS(O)₂R⁴, —NHC(O)R⁴, or —NHC(=NH)R⁴ wherein R⁴ is selected from $C_1$–$C_6$ alkyl and H; —C(O)R⁴ wherein R⁴ is $C_1$–$C_6$ alkyl (especially $C_1$–$C_3$ alkyl); or heterocyclyl; wherein any of said hetercyclyl, alkoxy, alkyl, and aryl may be optionally substituted; and
   R² is H;

or a salt, solvate, or physiologically functional derivative thereof.

Such sulfonamides include those wherein:
   A is phenyl para-substituted with —NHS(O)₂R⁹;
   R⁹ is substituted, preferably mono- or di-substituted, with halo, e.g., chloro-substituted phenyl or chloro-substituted thiophene (especially di-chloro-substituted phenyl or thiophene);
   D is methyl or isopropyl; and
   R⁷ is:
3-hydroxypropyl, 4-hydroxybutyl, 2-hydroxy-1-hydroxymethyl-ethyl, 2-oxopyrrolidin-2-yl-propyl, 3-(4-methyl-piperazine-1-yl)propyl, 3-(2-methyl-piperadin-1-yl)propyl, (3-pyrrolidin-1-yl)propyl, (4-pyrrolidin-1-yl)butyl, 2-(1-methyl-pyrrolidin-2-yl)ethyl, 1-methyl-1H-pyrrol-2yl-ethyl, (2-oxoimidazolidin-1-yl)ethyl, 3-imidazol-1-yl-propyl, 3-morpholin-4yl-propyl, 2-morpholin-4-yl-ethyl, (1-methyl-piperidin-4-yl), 3-dimethylamino-propyl, 3-diethylamino-propyl, 3-aminopropyl, 4-aminobutyl, acetyl, 4-methanesulfonyl amino-butyl, 2-acetylamino-ethyl or 4-guanidino-butyl.

In another particularly preferred embodiment, the compounds of formula (I) are thioureas wherein:
   A is phenyl para-substituted with —NHC(S)R⁸ and optionally further substituted;
   R⁸ is —NHR¹³;
   R¹³ is optionally substituted phenyl;
   D is $C_1$–$C_6$ alkyl or aralkyl;
   R¹ is NHR⁷;
   R⁷ is $C_1$–$C_6$ alkyl substituted by one or more heterocyclyl, $C_1$–$C_6$ alkoxy, hydroxy, —NR⁵R⁶ wherein R⁵ and R⁶ are independently H or $C_1$–$C_6$ alkyl, aryl, —NHS(O)₂R⁴, —NHC(O)R⁴, or —NHC(=NH)R⁴ wherein R⁴ is selected from $C_1$–$C_6$ alkyl and H; optionally substituted phenyl; —C(O)R⁴ wherein R⁴ is $C_1$–$C_6$ alkyl (especially $C_1$–$C_3$ alkyl); or heterocyclyl; especially $C_1$–$C_6$ alkyl substituted by one or more heterocyclyl; wherein any of said heterocyclyl, alkoxy, alkyl, and aryl may be optionally substituted; and
   R² is H;

or a salt, solvate, or physiologically functional derivative thereof.

Such thioureas include those wherein:
   in moiety A, optional substituents are $C_1$–$C_6$ alkyl, e.g., methyl, preferably 1 such substituent;
   R¹³ is phenyl substituted, preferably mono- or di-substituted, with trifluromethyl;
   D is methyl or benzyl; and
   R⁷ is 2-morpholin-4-yl-ethyl.

Specific examples of compounds of the present invention include the compounds of Examples 29–58, 61–68, 70, 71, 77, 78, 81–101, 103–122, 127–132, and 134–163 described below, or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and/or salts, solvates and/or physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

For example, pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating comprising a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 1986, 3(6):318.

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to herein.

The compounds of the present invention and their salts and solvates, and physiologically functional derivatives thereof, may be employed alone or in combination with other therapeutic agents for the treatment of the conditions mentioned herein. In particular, in anti-cancer therapy, combination with other chemotherapeutic, hormonal or antibody agents is envisaged as well as combination with surgical therapy and/or radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula (I) include the following:

(1) cell cycle specific anti-neoplastic agents include, but are not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, irinotecan, topotecan, CPT-11 and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR, and TIE-2 (other than those VEGFR and TIE-2 inhibitors described in the present invention); and other tyrosine kinase inhibitors such as inhibitors of CDK2 and CDK4 inhibitors.

The compounds of formula (I) and salts, solvates and physiological functional derivatives thereof, are active as inhibitors of at least one of the protein kinases TIE-2, VEGFR-2, and VEGFR-3.

The present invention thus also provides compounds of formula (I) and pharmaceutically acceptable salts or solvates thereof, or physiologically functional derivatives thereof, for use in medical therapy, and particularly in the treatment of disorders mediated by at least one of inappropriate TIE-2, VEGFR-2, and VEGFR-3 kinase activity.

The inappropriate TIE-2, VEGFR-2, and/or VEGFR-3 kinase activity referred to herein is any TIE-2, VEGFR-2, and/or VEGFR-3 kinase activity that deviates from the normal TIE-2, VEGFR-2, and/or VEGFR-3 kinase activity expected in a particular mammalian subject. Inappropriate TIE-2, VEGFR-2, and/or VEGFR-3 kinase activity may take the form of, for instance, an abnormal increase in activity, or an aberration in the timing and or control of TIE-2, VEGFR-2, and/or VEGFR-3 kinase activity. Such inappropriate activity may result then, for example, from overexpression or mutation of the protein kinase leading to inappropriate or uncontrolled activation. Furthermore, it is also understood that unwanted TIE-2, VEGFR-2, and/or VEGFR-3 kinase activity may reside in an abnormal source, such as a malignancy. That is, the level of TIE-2, VEGFR-2, and/or VEGFR-3 kinase activity does not have to be abnormal to be considered inappropriate, rather the activity derives from an abnormal source.

In a like manner, the inappropriate angiogenesis referred to herein is any angiogenic activity that deviates from the normal angiogenic activity expected in a particular mammalian subject. Inappropriate angiogenesis may take the form of, for instance, an abnormal increase in activity, or an aberration in the timing and or control of angiogenic activity. Such inappropriate activity may result then, for example, from overexpression or mutation of a protein kinase leading to inappropriate or uncontrolled activation. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting TIE-2, VEGFR-2, and/or VEGFR-3 kinase for the prevention and/or treatment of disorders related to inappropriate TIE-2, VEGFR-2, and/or VEGFR-3 activity.

In particular, the compounds of the present invention are useful in the treatment of susceptible forms of cancer, including tumor growth and metastasis. Furthermore, the compounds of the present invention can be used to provide additive or synergistic effects with certain existing cancer chemotherapies, and/or be used to restore effectiveness of certain existing cancer chemotherapies and radiation.

The compounds of the present invention are also useful in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders including glomerulonephritis, diabetic nephropathy, malignant nephrosclerosis, thrombotic microangiopathy syndromes, organ transplant rejection and glomerulopathies; and metabolic disorders including psoriasis, diabetes mellitus, chronic wound healing, inflammatory diseases (e.g., rheumatoid arthritis), stroke and neurodegenerative diseases; also diabetic retinopathy; macular degeneration; other diseases characterized by ocular neovascularization; and diseases characterized by hemangiomas.

A further aspect of the invention provides a method of treatment of a mammal suffering from a disorder mediated by at least one of inappropriate TIE-2, VEGFR-2, and VEGFR-3 activity, which includes administering to said subject an effective amount of a compound of formula (I) or a pharmaceutically acceptable salt, solvate, or a physiologically functional derivative thereof. In a preferred embodiment, the disorder is cancer, e.g., malignant tumors. This aspect of the invention also provides such a method wherein the disorder is a disease afflicting mammals which are characterized by cellular proliferation in the area of disorders associated with neo-vascularization and/or vascular permeability, including those disclosed herein.

A further aspect of the invention provides a method of treatment of a mammal suffering from cancer which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by at least one of inappropriate TIE-2, VEGFR-2 and VEGFR-3 kinase activity. In a preferred embodiment, the disorder is cancer, e.g., malignant tumors. This aspect of the invention also provides such a use wherein the disorder is a disease afflicting mammals which are characterized by cellular proliferation in the area of disorders associated with neo-vascularization and/or vascular permeability, including those disclosed herein.

A further aspect of the present invention provides the use of a compound of formula (I), or a pharmaceutically acceptable salt or solvate thereof, or a physiologically functional derivative thereof, in the preparation of a medicament for the treatment of cancer, e.g., malignant tumors.

The mammal requiring treatment with a compound of the present invention is typically a human being.

In another embodiment, therapeutically effective amounts of (a) the compounds of formula (I) or salts, solvates or physiologically derived derivatives thereof and (b) agents which inhibit growth factor receptor function may be administered in combination to a mammal for treatment of a disorder mediated by at least one of inappropriate TIE-2, VEGFR-2 and VEGFR-3 kinase activity, for instance in the treatment of cancer, e.g., malignant tumors. Such growth factor receptors include, for example, EGFR, PDGFR, erbB2, erbB4, VEGFR, and/or TIE-2. Growth factor receptors and agents that inhibit growth factor receptor function are described, for instance, in Kath, John C., Exp. Opin. Ther. Patents (2000) 10(6): 803–818 and in Shawver et al. DDT Vol 2, No. 2 February 1997.

The compounds of the formula (I) or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds, or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate angiogenesis, including: administering to said mammal a therapeutically effective amount of a compound of formula (I), or a salt, solvate or physiologically functional derivative thereof. In one embodiment, the inappropriate angiogenic activity is due to at least one of inappropriate VEGFR1, VEGFR2, VEGFR3, or TIE-2 activity. In another embodiment, the inappropriate angiogenesis is due to at least one of inappropriate VEGFR-2, VEGFR-3, and TIE-2 kinase activity. In a preferred embodiment, the inappropriate angiogenic activity is due to at least one of inappropriate VEGFR-2 and TIE-2 kinase activity. In a further embodiment, the method further includes administering a therapeutically effective amount of a VEGFR2 inhibitor along with the compounds of formula (I) or salts, solvates or physiologically functional derivatives thereof. Preferably the disorder is cancer, e.g., malignant tumors. This aspect of the invention also provides such methods wherein the disorder is a disease afflicting mammals which are characterized by cellular proliferation in the area of disorders associated with neo-vascularization and/or vascular permeability, including those disclosed herein.

In another aspect of the present invention, there is provided the use of a compound of formula (I), or a salt, solvate or physiologically functional derivative thereof in the preparation of a medicament for use in treating a disorder in a mammal, said disorder being characterized by inappropriate angiogenesis. In one embodiment, the inappropriate angiogenic activity is due to at least one of inappropriate VEGFR1, VEGFR2, VEGFR3 or TIE-2 activity. In another embodiment, the inappropriate angiogenesis is due to at least one of inappropriate VEGFR-2, VEGFR-3, and TIE-2 kinase activity. In a preferred embodiment, the inappropriate angiogenic activity is due to at least one of inappropriate VEGFR-2 and TIE-2 kinase activity. In a further embodiment, the use further includes use of a VEGFR2 inhibitor to prepare said medicament. Preferably the disorder is cancer, e.g., malignant tumors. This aspect of the invention also provides such uses wherein the disorder is a disease afflicting mammals which are characterized by cellular proliferation in the area of disorders associated with neo-vascularization and/or vascular permeability, including those disclosed herein.

The combination of a compound of formula (I) or salts, solvates, or physiologically functional derivatives thereof with a VEGFR2 inhibitor may be employed in combination in accordance with the invention by administration concomitantly in (1) a unitary pharmaceutical composition including both compounds, or (2) separate pharmaceutical compositions each including one of the compounds. Alternatively, the combination may be administered separately in a sequential manner wherein one is administered first and the other second or vice versa. Such sequential administration may be close in time or remote in time.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula (I) can be prepared according to the synthetic sequence illustrated in Schemes 1 and 2, which contain a general route for the synthesis of the targeted pyrazolo[3,4-d]pyrimidines. Specific details of synthetic routes according to Scheme 1 and 2 are shown in the Examples following.

Pyrazolopyrimidine (iii) is prepared by the method described by Hauser et al. (J. Org. Chem. (1960), 1570; J. Org. Chem. (1961), 451). Chloride (i) is reacted with an appropriate hydrazine to give compound (ii), which is then cyclized to the desired pyrazolopyrimidine (iii) by treatment with base, such as aqueous potassium hydroxide. This compound is then treated with phosphorus oxychloride to yield (iv). Reaction of (iv) with an oxidant, such as but not limited to mCBPA or Oxone, yields the corresponding sulfoxide (n=1) or sulfone (n=2). Treatment of (v) with a chosen nucleophile affords (vi). Suzuki coupling of (v) with a boronic acid in the presence of base and a transition metal catalyst, such as a palladium complex, yields the desired coupling product (vii). According to the specific nature of substituents Nu, D' and A', standard chemical manipulations are then performed to allow for the isolation of the desired final product (viii).

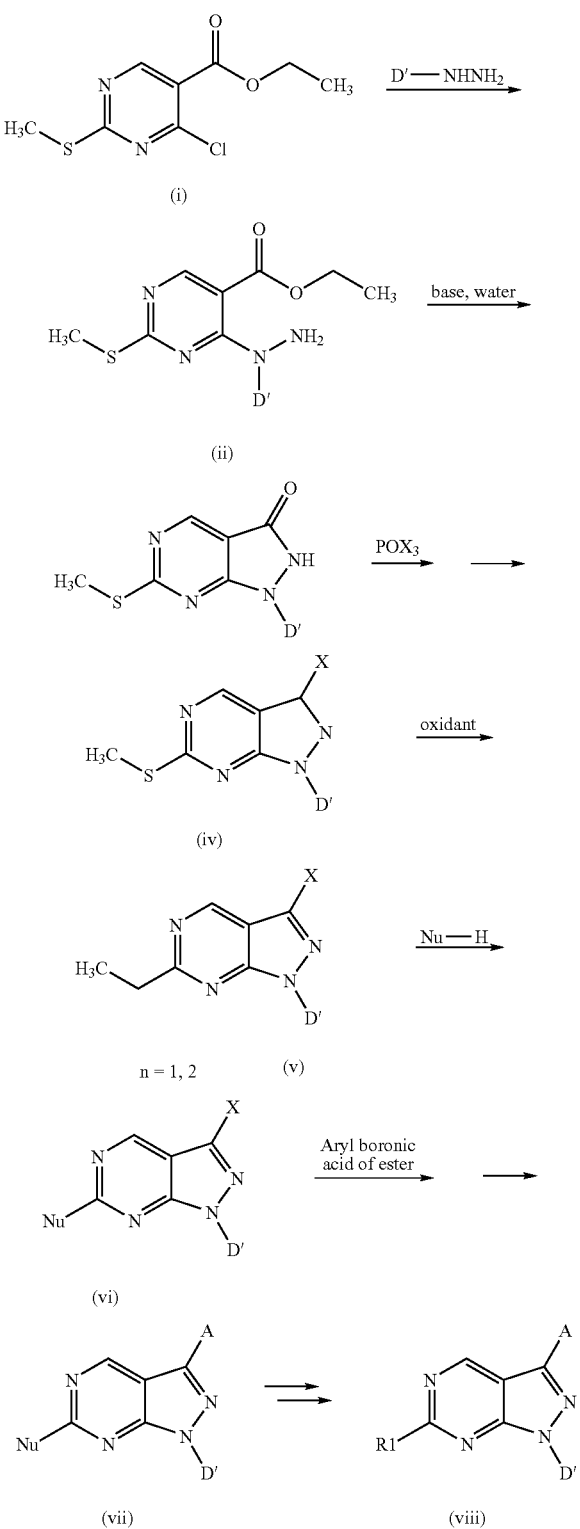

Alternatively in Scheme 1, a coupling reaction could be performed on intermediate (iv), yielding intermediate (ix). Reaction of (ix) with an oxidant followed by treatment with a nucleophile would provide intermediate (vi).

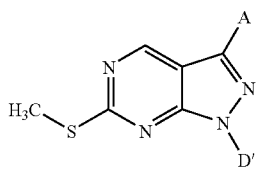

(ix)

Alternatively in Scheme 1, hydrazine may be used to provide compounds represented in Scheme 2 (ix). These may be substituted using methods known to those skilled in the art, including but not limited to, Mitsunobu displacements, alkylation with electrophiles in the presence of base, transition metal catalyzed aryl couplings, Michael additions, and transition-metal catalyzed π-allyl couplings.

Scheme 2

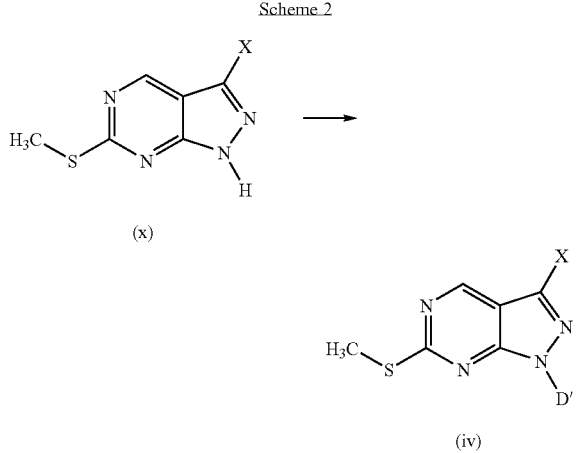

EXAMPLES

Certain embodiments of the present invention will now be illustrated by way of example only. The physical data given for the compounds exemplified is consistent with the assigned structure of those compounds.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams);
mg (milligrams);
L (liters);
mL (milliliters);
μL (microliters);
psi (pounds per square inch);
M (molar);
mM (millimolar);
i. v. (intravenous);
Hz (Hertz);
MHz (megahertz);
mol (moles);
mmol (millimoles);
rt (room temperature);
min (minutes);
h (hours);
mp (melting point);
TLC (thin layer chromatography);
T$_r$ (retention time);
RP (reverse phase);
MeOH (methanol);
i-PrOH (isopropanol);
TEA (triethylamine);
TFA (trifluoroacetic acid);
TFAA (trifluoroacetic anhydride);
THF (tetrahydrofuran);
DMSO (dimethylsulfoxide);
AcOEt (ethyl acetate);
DME (1,2-dimethoxyethane);
DCM (dichloromethane);
DCE (dichloroethane);
DMF (N,N-dimethylformamide);
DMPU (N,N'-dimethylpropyleneurea);
CDI (1,1-carbonyldiimidazole);
IBCF (isobutyl chloroformate);
HOAc (acetic acid);
HOSu (N-hydroxysuccinimide);
HOBT (1-hydroxybenzotriazole);
mCPBA (meta-chloroperbenzoic acid;
EDC (ethylcarbodiimide hydrochloride);
BOC (tert-butyloxycarbonyl);
FMOC (9-fluorenylmethoxycarbonyl);
DCC (dicyclohexylcarbodiimide);
CBZ (benzyloxycarbonyl);
Ac (acetyl);
atm (atmosphere);
TMSE (2-(trimethylsilyl)ethyl);
TMS (trimethylsilyl);
TIPS (triisopropylsilyl);
TBS (t-butyldimethylsilyl);
DMAP (4-dimethylaminopyridine);
BSA (bovine serum albumin)
ATP (adenosine triphosphate);
HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO$_3$ (fumed HNO$_3$); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR (hereinafter also "NMR") spectra were recorded on a Varian VXR-300, a Varian Unity-300, a Varian Unity-400 instrument, a Brucker AVANCE-400, a General Electric QE-300, or a Bruker AM 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC/MS system using electrospray ionization. LC conditions: 4.5% to 90%

CH₃CN (0.02% TFA) in 3.2 min with a 0.4 min hold and 1.4 min re-equilibration; detection by MS, UV at 214 nm, and a light scattering detector (ELS). Column: 1×40 mm Aquasil (C18).

For analytical hplc; ca 0.05 mg of the reaction mixtures were injected in 5 uL of DMSO onto a 4.6×150 mm I. D. Zorbax Eclipse XDB-C18 column at 3 mL/min with a 10 min gradient from 5% CH₃CN (0.1% TFA) to 95% CH₃CN (0.1% TFA) in H₂O (0.1% TFA).

For preparative (prep) hplc; ca 50 mg of the final products were injected in 500 uL of DMSO onto a 50×20 mm I. D. YMC CombiPrep ODS-A column at 20 mL/min with a 10 min gradient from 10% CH₃CN (0.1% TFA) to 90% CH₃CN (0.1% TFA) in H₂O (0.1% TFA) and a 2 min hold. Flash chromatography was run over Merck Silica gel 60 (230–400 mesh).

Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution.

Naming is done using the autonom utility of ISISDRAW.

Example 1

Preparation of 4-(N-Methyl-hydrazino)-2-methylsulfanyl-pyrimidine-5-carboxylic acid ethyl ester A solution of methyl hydrazine (4.0 g, 0.087 mol, 2 eq) in ethanol (50 mL) was slowly added to a solution of ethyl 4-chloro-2-methylthio-5-pyrimidinecarboxylate (10 g, 0.043 mol) in ethanol (50 mL) while keeping the reaction temperature below 15° C. After the addition was completed, the reaction mixture was stirred for 2 hours at the room temperature. Water (100 mL) was then added and the formed product was isolated by filtration. After drying, the product was recrystalized from a 1:1 toluene-hexane mixture to give 7.3 g (69%) of the desired 4-(N-methyl-hydrazino)-2-methylsulfanyl-pyrimidine-5-carboxylic acid ethyl ester; LC/MS (m/e)=243.1 (MH+), Rt=1.15 min.

Example 2

Preparation of 1-Methyl-6-methylsulfanyl-1,2-dihydro-pyrazolo[3,4-d]pyrimidin-3-one 4-(N-Methyl-hydrazino)-2-methylsulfanyl-pyrimidine-5-carboxylic acid ethyl ester (6.0 g, 0.025 mol) was added to a 10% aqueous potassium hydroxide solution. The reaction mixture was heated to reflux for 15 minutes, and then cooled to room temperature. The system was acidified with a 25% aqueous acetic acid solution and the formed product was isolated by filtration. Crude product was recrystalized from a 3:1 ethanol-water mixture to give 4.6 g (95%) of pure 1-methyl-6-methylsulfanyl-1,2-dihydro-pyrazolo[3,4-d]pyrimidin-3-one; LC/MS (m/e)=197.0 (MH+), Rt=1.30 min.

Example 3

Preparation of 3-Chloro-1-methyl-6-methylsulfanyl-1H-pyrazolo[3,4-d]pyrimidine

1-Methyl-6-methylsulfanyl-1,2-dihydro-pyrazolo[3,4-d]pyrimidin-3-one (2.0 g, 0.01 mol) was heated with phosphorus oxychloride (8 mL) in a sealed tube at 140° C. for 6 hours. The reaction mixture was then poured into ice-water and basified with ammonium hydroxide. The formed product was isolated by filtration. The crude product was recrystalized from a 1:1 ethanol-water mixture to give 1.3 g (61%) of pure 3-chloro-1-methyl-6-methylsulfanyl-1H-pyrazolo[3,4-d]pyrimidine; LC/MS (m/e)=215.0 (MH+), Rt=1.94 min.

Example 4

Preparation of 3-Bromo-1-methyl-6-methylsulfanyl-1H-pyrazolo[3,4-d]pyrimidine

1-Methyl-6-methylsulfanyl-1,2-dihydro-pyrazolo[3,4-d]pyrimidin-3-one (2.0 g, 0.01 mol) was refluxed with phosphorus oxybromide (6 g) in acetonitrile (60 mL). Water (100 mL) was then added and the reaction mixture cooled to 5° C., hold for 1 hour and filtered to give 1.6 g (61%) of pure 3-bromo-1-methyl-6-methylsulfanyl-1H-pyrazolo[3,4-d]pyrimidine; ¹H-NMR (DMSO): δ 2.61 (s, 3H), 3.96 (s, 3H), 9.00 (s, 1H), LC/MS (m/e)=260.8 (MH+), Rt=1.89 min.

Example 5

Preparation of 3-Chloro-6-methanesulfonyl-1-methyl-1H-pyrazolo[3,4-d]pyrimidine

To a solution of 3-chloro-1-methyl-6-methylsulfanyl-1H-pyrazolo[3,4-d]pyrimidine (214 mg, 1 mmol) in chloroform (15 mL) was added 3-chloroperoxybenzoic acid (549 mg, 3 mmol, 3 eq) and the reaction mixture was allowed to stir for 5 hours at room temperature. To the reaction mixture were then added 10 mL of 1 M Na₂CO₃ solution and the layers were separated. The organic layer was washed with water, dried over MgSO₄ and evaporated to give 3-chloro-6-methanesulfonyl-1-methyl-1H-pyrazolo[3,4-d]pyrimidine (250 mg, 95% yield); LC/MS (m/e)=260.8 (MH+), Rt=1.81 min.

Example 6

Preparation of 3-Bromo-6-methanesulfonyl-1-methyl-1H-pyrazolo[3,4-d]pyrimidine

To a solution of 3-bromo-1-methyl-6-methylsulfanyl-1H-pyrazolo[3,4-d]pyrimidine (260 mg, 1 mmol) in chloroform (15 mL) was added 3-chloroperoxybenzoic acid (549 mg, 3 mmol, 3 eq) and the reaction mixture was allowed to stir for 5 hours at room temperature. To the reaction mixture were then added 10 mL of 1 M Na₂CO₃ solution and the layers were separated. The organic layer was washed with water, dried over MgSO₄ and evaporated to give 3-bromo-6-methanesulfonyl-1-methyl-1H-pyrazolo[3,4-d]pyrimidine (262 mg, 91% yield); LC/MS (m/e)=291.0 (MH+). Rt=1.39 min.

Example 7

Preparation of 1-Benzyl-3-bromo-6-methanesulfonyl-1-pyrazolo[3,4-d]pyrimidine

Prepared as described above in Example 1 starting with 4-chloro-2-methylthio-5-pyrimidinecarboxylate and benzylhydrazine to give the intermediate pure 1-benzyl-6-methylsulfanyl-1,2-dihydro-pyrazolo[3,4-d]pyrimidin-3-one. The synthesis then follows as in Examples 2 and 3 to give 1-benzyl-3-bromo-6-methylsulfanyl-1H-pyrazolo[3,4-d]pyrimidine. To a solution of 1-benzyl-3-bromo-6-methylsulfanyl-1H-pyrazolo[3,4-d]pyrimidine (334 mg, 1 mmol) in chloroform (15 mL) was added 3-chloroperoxybenzoic acid (549 mg, 3 mmol, 3 eq) and the reaction mixture was allowed to stir for 5 hours at room temperature. To the reaction mixture were then added 10 mL of 1 M Na₂CO₃ solution and the layers were separated. The organic layer was washed with water, dried over MgSO₄ and evaporated to give 1-benzyl-3-bromo-6-methanesulfonyl-1H-pyrazolo[3,4-d]pyrimidin-3-one (291 mg, 78% yield); LC/MS (m/e)=369.0 (MH+), Rt=1.95 min.

Example 8

Preparation of 2-(3-Chloro-1-methyl-1H-pyrazolo[3,4-d]pyrimidin-6-ylamino)-ethanol To a solution of 3-chloro-6-methanesulfonyl-1-methyl-1H-pyrazolo[3,4-d]pyrimidine (131 mg, 0.5 mmol) in 1-methyl-2-pyrrolidinone (5 mL) was added ethanolamine (150 mg, 2.5 mmol, 5 eq) and the reaction mixture was heated to 50° C. After 1 hour, water (20 mL) was added, followed by ethyl acetate (20 mL). The layers were separated. The organic layer was washed with brine, dried over $MgSO_4$, filtered and evaporated. The resulting yellow residue was purified by column chromatography (50% ethyl acetate-hexane) to give 2-(3-chloro-1-methyl-1H-pyrazolo[3,4-d]pyrimidin-6-ylamino)-ethanol (100 mg, 87% yield); LC/MS (m/e)=228.2 (MH+), Rt=1.44 min.

Example 9

Preparation of (3-Chloro-1-methyl-1H-pyrazolo[3,4-d]pyrimidin-6-yl)-(2-morpholin-4-yl-ethyl)-amine Prepared as described above in Example 8 starting from 3-chloro-6-methanesulfonyl-1-methyl-1H-pyrazolo[3,4-d]pyrimidin-3-one and N-aminoethylmorpholine to give the title compound (3-chloro-1-methyl-1H-pyrazolo[3,4-d]pyrimidin-6-yl)-(2-morpholin-4-yl-ethyl)-amine; $^1$H-NMR ($CDCl_3$): δ 2.54 (m, 4H), 2.65 (m, 2H), 3.59 (m, 2H), 3.75 (m, 2H), 3.87 (s, 3H), 6.02 (br s, 1H), 8. (s, 1H), LC/MS (m/e)=297.2 (MH+), Rt=0.95 min.

Example 10

Preparation of (3-Chloro-1-methyl-1H-pyrazolo[3,4-d]pyrimidin-6-yl)-(2-methoxy-ethyl)-amine Prepared as described above in Example 8 starting from 3-chloro-6-methanesulfonyl-1-methyl-1H-pyrazolo[3,4-d]pyrimidin-3-one and 2-methoxyethylamine to give the title compound (3-chloro-1-methyl-1H-pyrazolo[3,4-d]pyrimidin-6-yl)-(2-methoxy-ethyl)-amine. $^1$H-NMR ($CDCl_3$): δ 3.42 (s, 3H), 3.62 (m, 2H), 3.71 (m, 2H), 3.87 (s, 3H), 8.56 (s, 1H). LC/MS (m/e)=242.0.2 (MH+). Rt=1.47 min.

Example 11

Preparation of N'-(3-Chloro-1-methyl-1H-pyrazolo[3,4-d]pyrimidin-6-yl)-N,N-diethyl-ethane-1,2-diamine Prepared as described above in Example 8 starting from 3-chloro-6-methanesulfonyl-1-methyl-1H-pyrazolo[3,4-d]pyrimidin-3-one and N,N-diethylethylenediamine to give the title compound N'-(3-chloro-1-methyl-1H-pyrazolo[3,4-d]pyrimidin-6-yl)-N,N-diethyl-ethane-1,2-diamine; LC/MS (m/e)=283.0 (MH+). Rt=1.20 min.

Example 12

Preparation of N'-(3-Chloro-1-methyl-1H-pyrazolo[3,4-d]pyrimidin-6-yl)-N,N -diethyl-butane-1,4-diamide Prepared as described above in Example 8 starting from 3-chloro-6-methanesulfonyl-1-methyl-1H-pyrazolo[3,4-d]pyrimidin-3-one and N,N-diethyl-1,4-butyldiamide to give the title compound N'-(3-chloro-1-methyl-1H-pyrazolo[3,4-d]pyrimidin-6-yl)-N,N -diethyl-butane-1,4-diamine. LC/MS (m/e)=311.2 (MH+). Rt=1.22 min.

Example 13

Preparation of (3-Bromo-1-methyl-1H-pyrazolo[3,4-d]pyrimidin-6-yl)-(2-morpholin-4-yl-ethyl)-amine Prepared as described above in Example 8 starting from 3-bromo-6-methanesulfonyl-1-methyl-1H-pyrazolo[3,4-d]pyrimidine and N-aminoethylmorpholine to give the title compound (3-bromo-1-methyl-1H-pyrazolo[3,4-d]pyrimidin-6-yl)-(2-morpholin-4-yl-ethyl)-amine; $^1$H-NMR (DMSO): δ 2.43 (m, 4H), 2.50 (m, 2H), 3.47 (m, 2H), 3.55 (m, 2H), 3.77 (s, 3H), 7.61 (br s, 1H), 8.63 (s, 1H); LC/MS (m/e)=340.21 (MH+), Rt=1.13 min.

Example 14

Preparation of (1-Benzyl-3-bromo-1H-pyrazolo[3,4-d]pyrimidin-6-yl)-(2-morpholin-4-yl-ethyl)-amine Prepared as described above in Example 8 starting from 1-benzyl-3-bromo-6-methanesulfonyl-1H-pyrazolo[3,4-d]pyrimidine and N-aminoethylmorpholine to give the title compound (1-benzyl-3-bromo-1H-pyrazolo[3,4-d]pyrimidin-6-yl)-(2-morpholin-4-yl-ethyl)-amine; LC/MS (m/e)=419.2 (MH+), Rt=1.47 min.

Example 15

Preparation of 2-[3-(4-Amino-phenyl)-1-methyl-1H-pyrazolo[3,4-d]pyrimidin-6-ylamino)-ethanol To a solution of 2-(3-chloro-1-methyl-1H-pyrazolo[3,4-d]pyrimidin-6-ylamino)-ethanol (244 mg, 1.07 mmol) in dioxane (21 mL) and $H_2O$ (7 mL) was added anhydrous potassium carbonate (443 mg, 3.21 mmol, 3 eq), followed by 4-(4,4,5,5-tetramethyl-1,3,2-dioxaborolan-2-yl)aniline (350 mg, 1.6 mmol, 1.5 eq). The reaction mixture was degassed and tetrakis(triphenylphosphine)palladium (61 mg, 0.053 mmol, 0.05 eq) was added. The system was then heated under reflux for 24 hours and cooled to room temperature. The layers were separated. The organic solution was treated with ethyl acetate (50 mL) and water (10 mL). The resulting organic layer was then separated, washed with brine, dried over $MgSO_4$, filtered and evaporated. The product was purified by column chromatography (100% ethyl acetate) to give 130 mg (42% yield) of pure 2-[3-(4-amino-phenyl)-1-methyl-1H-pyrazolo[3,4-d]pyrimidin-6-ylamino)-ethanol; $^1$H-NMR (DMSO): δ 3.44 (m, 2H), 3.59 (m, 2H), 3.79 (s, 3H), 4.70 (br s, 1H), 5.32 (br s, 2H), 6.65 (d, 2H, J=8.5 Hz), 7.23 (br s, 1 H) 7.64 (d, 2H, J=8.5 Hz), 9.05 (br, 1H); LC/MS (m/e)=285.4 (MH+), Rt=1.54 min.

Example 16

Preparation of [3-(4-Amino-phenyl)-1-methyl-1H-pyrazolo[3,4-d]pyrimidin-6-yl]-(2-morpholin-4-yl-ethyl)-amine Prepared as described above in Example 15 starting from (3-chloro-1-methyl-1H-pyrazolo[3,4-d]pyrimidin-6-yl)-(2-morpholin-4-yl-ethyl)-amine and 4-(4,4,5,5-tetramethyl-1,3,2-dioxaborolan-2-yl)aniline to give the title compound [3-(4-amino-phenyl)-1-methyl-1H-pyrazolo[3,4-d]pyrimidin-6-yl]-(2-morpholin-4-yl-ethyl)-amine; LC/MS (m/e)=354.4 (MH+), Rt=1.12 min.

Example 17

Preparation of [3-(4-Amino-phenyl)-1-methyl-1H-pyrazolo[3,4-d]pyrimidin-6-yl]-(2-methoxy-ethyl)-amine Prepared as described above in Example 15 starting from (3-chloro-1-methyl-1H-pyrazolo[3,4-d]pyrimidin-6-yl)-(2-methoxy-ethyl)-amine and 4-(4,4,5,5-tetramethyl-1,3,2-dioxaborolan-2-yl)aniline to give the title compound [3-(4-amino-phenyl)-1-methyl-1H-pyrazolo[3,4-d]pyrimidin-6-yl]-(2-methoxy-ethyl)-amine; LC/MS (m/e)=299.0 (MH+), Rt=1.42 min.

Example 18

Preparation of N-[3-(4-Amino-phenyl)-1-methyl-1H-pyrazolo[3,4-d]pyrimidin-6-yl]-N',N'-diethyl-ethane-1,2-diamine Prepared as described above in Example 15 starting from N'-(3-chloro-1-methyl-1H-pyrazolo[3,4-d]pyrimidin-6-yl)-N,N-diethyl-ethane-1,2-diamine and 4-(4,4,5,5-tetramethyl-1,3,2-dioxaborolan-2-yl)aniline to give the title compound N-[3-(4-amino-phenyl)-1-methyl-1H-pyrazolo[3,4-d]pyrimidin-6-yl]-N',N'-diethyl-ethane-1,2-diamine; $^1$H-NMR (MeOH): δ 1.38 (m, 6H), 3.36 (m, 4H), 3.82 (m, 2H), 3.92 (m, 2H), 3.98 (s, 3H), 7.46 (d, 2H, J=8.4 Hz), 8.09 (d, 2H, J=8.4 Hz), 9.18 (s, 1H), LC/MS (m/e)=340.2 (MH+), Rt=0.98 min.

Example 19

Preparation of N-[3-(4-Amino-phenyl)-1-methyl-1H-pyrazolo[3,4-d]pyrimidin-6-yl]-N',N'-diethyl-1,4-diamine Prepared as described above in Example 15 starting from N'-(3-chloro-1-methyl-1H-pyrazolo[3,4-d]pyrimidin-6-yl)-N,N-diethyl-butane-1,4-diamine and 4-(4,4,5,5-tetramethyl-1,3,2-dioxaborolan-2-yl)aniline to give the title compound N-[3-(4-amino-phenyl)-1-methyl-1H-pyrazolo[3,4-d]pyrimidin-6-yl]-N',N'-diethyl-butane-1,4-diamine; $^1$H-NMR (MeOH): δ 1.33 (m, 6H), 1.86 (m, 4H), 3.28 (m, 4H), 3.82 (m, 2H), 3.69 (m, 2H), 3.98 (s, 3H), 7.44 (d, 2H, J=8.4 Hz), 8.07 (d, 2H, J=8.4 Hz), 9.23 (s, 1H); LC/MS (m/e)=368.2 (MH+), Rt=1.20 min.

Example 20

Preparation of {2-Methyl-4-[1-methyl-6-(2-morpholin-4-yl-ethylamino)-1H-pyrazolo[3,4-d]pyrimidin-3-yl]-phenyl}-carbamic acid tert-butyl ester Prepared as described above in Example 15 starting from (3-chloro-1-methyl-1H-pyrazolo[3,4-d]pyrimidin-6-yl)-(2-morpholin-4-yl-ethyl)-amine and [2-methyl-4-(4,4,5,5-tetramethyl-[1,3,2]dioxaborolan-2-yl)-phenyl]-carbamic acid tert-butyl ester to give the title compound {2-methyl-4-[1-methyl-6-(2-morpholin-4-yl-ethylamino)-1H-pyrazolo[3,4-d]pyrimidin-3-yl]-phenyl}-carbamic acid tert-butyl ester; LC/MS (m/e)=468.2 (MH+), Rt=1.40 min

Example 21

Preparation of [3-(3-Amino-phenyl)-1-methyl-1H-pyrazolo[3,4-d]pyrimidin-6-yl]-(2-morpholin-4-yl-ethyl)-amine Prepared as described above in Example 15 starting from (3-chloro-1-methyl-1H-pyrazolo[3,4-d]pyrimidin-6-yl)-(2-morpholin-4-yl-ethyl)-amine and 3-anilinoboronic acid to give the title compound [3-(3-amino-phenyl)-1-methyl-1H-pyrazolo[3,4-d]pyrimidin-6-yl]-(2-morpholin-4-yl-ethyl)-amine; LC/MS (m/e)=354.4 (MH+), Rt=1.18 min

Example 22

Preparation of {2-Fluoro-4-[1-methyl-6-(2-morpholin-4-yl-ethylamino)-1H-pyrazolo[3,4]pyrimidin-3-yl]-phenyl}-carbamic acid tert-butyl ester Prepared as described above in Example 15 starting from (3-bromo-1-methyl-1H-pyrazolo[3,4-d]pyrimidin-6-yl)-(2-morpholin-4-yl-ethyl)-amine and [2-fluoro-4-(4,4,5,5-tetramethyl-[1,3,2]dioxaborolan-2-yl)-phenyl]-carbamic acid tert-butyl ester to give the title compound {2-fluoro-4-[1-methyl-6-(2-morpholin-4-yl-ethylamino)-1H-pyrazolo[3,4-d]pyrimidin-3-yl]-phenyl}-carbamic acid tert-butyl ester; LC/MS (m/e)=472.2 (MH+), Rt=1.72 min

Example 23

Preparation of [(Amino-trifluoromethyl-phenyl)-methyl-1H-pyrazolo[3,4-d]pyrimidin-6-yl]-(2-morpholin-4-yl-ethyl)-amine Prepared as described above in Example 15 starting from (3-bromo-1-methyl-1H-pyrazolo[3,4-d]pyrimidin-6-yl)-(2-morpholin-4-yl-ethyl)-amine and (4,4,5,5-tetramethyl-[1,3,2]dioxaborolan-2-yl)-trifluoromethyl-phenylamine to give the title compound {[(amino-trifluoromethyl-phenyl)-methyl-1H-pyrazolo[3,4-d]pyrimidin-6-yl]-(2-morpholin-4-yl-ethyl)-amine; LC/MS (m/e)=422.3 (MH+), Rt=0.99 min

Example 24

Preparation of [3-(4-Amino-phenyl)-1-benzyl-1H-pyrazolo[3,4-d]pyrimidin-6-yl]-N',N'-diethyl-ethane-1,2-diamine Prepared as described above in Example 15 starting from 1-benzyl-3-bromo-6-methanesulfonyl-1H-pyrazolo[3,4-d]pyrimidine and 4-(4,4,5,5-tetramethyl-1,3,2-dioxaborolan-2-yl)aniline to give the title compound [3-(4-amino-phenyl)-

1-benzyl-1H-pyrazolo[3,4-d]pyrimidin-6-yl]-N',N'-diethyl-ethane-1,2-diamine; LC/MS (m/e)=429.0 (MH+), Rt=1.42 min.

Example 25

Preparation of {3-[1-Methyl-6-(2-morpholin-4-yl-ethylamino)-1H-pyrazolo[3,4-d]pyrimidin-3-yl]-benzyl}-carbamic acid tert-butyl ester Prepared as described above in Example 15 starting from (3-bromo-1-methyl-1H-pyrazolo[3,4-d]pyrimidin-6-yl)-(2-morpholin-4-yl-ethyl)-amine and [3-(4,4,5,5-tetramethyl-[1,3,2]dioxaborolan-2-yl)-benzyl]-carbamic acid carbamic acid tert-butyl ester to give the title compound {3-[1-methyl-6-(2-morpholin-4-yl-ethylamino)-1H-pyrazolo[3,4-d]pyrimidin-3yl]-benzyl}-carbamic acid tert-butyl ester; LC/MS (m/e)=468.4 (MH+), Rt=1.39 min

Example 26

Preparation of [3-(4-Amino-3-methyl-phenyl)-1-methyl-1H-pyrazolo[3,4-d]pyrimidin-6-yl]-(2morpholin-4yl-ethyl)-amine {2-Methyl-4-[1-methyl-6-(2-morpholin-4-yl-ethylamino)-1H-pyrazolo[3,4-d]pyrimidin-3-yl]-phenyl}-carbamic acid tert-butyl ester (468 mg, 1 mmol) was dissolved in 10 mL of trifluoroacetic acid. After 1 hour the reaction mixture was evaporated, and methanol (10 mL) followed by water (10 mL) was added. The reaction mixture was then neutralised with 1 M NaOH to pH~8 and product was filtered and dryed to give pure [3-(4-amino-3-methyl-phenyl)-1-methyl-1H-pyrazolo[3,4-d]pyrimidin-6-yl]-(2-morpholin-4-yl-ethyl)-amine; LC/MS (m/e)=368.2 (MH+), Rt=1.02 min.

Example 27

Preparation of [3-(4-Amino-3-fluoro-phenyl)-1-methyl-1H-pyrazolo[3,4-d]pyrimidin-6-yl]-(2-morpholin-4-yl-ethyl)-amine Prepared as described above in Example 26 starting from {2-fluoro-4-[1-methyl-6-(2-morpholin-4-yl-ethylamino)-1H-pyrazolo[3,4-d]pyrimidin-3-yl]-phenyl}-carbamic acid tert-butyl ester to give the title compound [3-(4-amino-3-fluoro-phenyl)-1-methyl-1H-pyrazolo[3,4-d]pyrimidin-6-yl]-(2morpholin-4-yl-ethyl)-amine: LC/MS (m/e)=372.0 (MH+), Rt=1.12 min.

Example 28

Preparation of [3-(3-Aminomethyl-phenyl)-1-methyl-1H-pyrazolo[3,4-d]pyrimidin-6-yl]-(2-morpholin-4-yl-ethyl)-amine Prepared as described above in Example 26 starting from {3-[1-methyl-6-(2-morpholin-4-yl-ethylamino)-1H-pyrazolo[3,4-d]pyrimidin-3-yl]-benzyl}-carbamic acid tert-butyl ester to give the title compound [3-(3-aminomethyl-phenyl)-1methyl-1H-pyrazolo[3,4-d]pyrimidin-6-yl]-(2-morpholin-4-yl-ethyl)-amine; LC/MS (m/e)=368.4 (MH+), Rt=0.80 min.

Example 29

Preparation of 1-(2-Fluoro-5-trifluoromethyl-phenyl)-3-{4-[(2-hydroxy-ethylamino)-methyl-1H-pyrazolo[3,4-d]pyrimidin-3-yl]-phenyl}-urea To a solution of 2-[3-(4-amino-phenyl)-1-methyl-1H-pyrazolo[3,4-d]pyrimidin-6-ylamino)-ethanol (25.4 mg, 0.1 mmol) in N-methylpyrollidine (0.5 mL) was added 2-fluoro-5-trifluoromethyl-phenyl isocyanate (22 mg, 0.11 mmol, 1.1 eq). The reaction mixture was stirred for 1 hour at room temperature while monitored by TLC. The mixture was then evaporated and the crude product was purified by prep. HPLC to give pure 1-(2-fluoro-5-trifluoromethyl-phenyl)-3-{4-[(2-hydroxy-ethylamino)-methyl-1H-pyrazolo[3,4-b]pyrimidin-3-yl]-phenyl}-urea as its TFA salt; $^1$H-NMR (DMSO): δ 3.46 (m, 2H), 3.58 (m, 2H), 3.89 (s, 3H), 4.11 (br s, 1H), 4.72 (br s, 1H), 7.41 (m, 1H), 7.58 (m, 3H), 7.93 (m, 2H), 8.58 (br s, 1 H), 8.9 (m, 1H), 9.13 (br s, 1H), 9.40 (br s, 1H); LC/MS (m/e)=490.2 (MH+).

Example 30

Preparation of (Fluoro-trifluoromethyl-phenyl)-carbamic acid 2-(3-{4-[3-(fluoro-trifluoromethyl-phenyl)-ureido]-phenyl}-1-methyl-1H-pyrazolo[3,4-d]pyrimidin-6-ylamino)-ethyl ester To a solution of 2-[3-(4-amino-phenyl)-1-methyl-1H-pyrazolo[3,4-d]pyrimidin-6-ylamino)-ethanol (25.4 mg, 0.1 mmol) in N-methylpyrrolidinine (0.5 mL) was added 2-fluoro-5-trifluoromethyl-phenyl isocyanate (22 mg, 0.11 mmol, 2.1 eq). The reaction mixture was stirred for 1 hour at room temperature while monitored by TLC. The mixture was then evaporated and the crude product was purified by preparative HPLC to give pure (2-fluoro-5-trifluoromethyl-phenyl)-carbamic acid 2-(3-{4-[3-(2-fluoro-5-trifluoromethyl-phenyl)-ureido]-phenyl}-1-methyl-1H-pyrazolo[3,4-d]pyrimidin-6-ylamino)-ethyl ester; $^1$H-NMR (DMSO): δ 3.71 (m, 2H), 3.81 (s, 3H), 4.34 (m, 2H), 7.41–7.60 (m, 4H), 7.92 (d, 2H, J=8.4 Hz), 8.11 (br s, 1H), 8.63 (s, 1H), 8.94 (s, 1 H), 9.15 (s, 1H), 9.36 (br s, 1H), 9.75 (br s, 1H); LC/MS (m/e)=695.2 (MH+).

Example 31

Preparation of 1-(2-Fluoro-5-trifluoromethyl-phenyl)-3-{4-[1-methyl-6-(2-morpholin-4-yl-ethylamino)-1H-pyrazolo[3,4-d]pyrimidin-3-yl]-phenyl}urea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 2-fluoro-5-trifluoromethyl-phenyl isocyanate to give the title compound 1-(2-fluoro-5-trifluoromethyl-phenyl)-3-{4-[1-methyl-6-(2-morpholin-4-yl-ethylamino)1H-pyrazolo[3,4-d]pyrimidin-3-yl]-phenyl}-urea as its TFA salt; LC/MS (m/e)=559.2 (MH+), Rt=1.95 min.

Example 32

Preparation of 1-(2-Fluoro-5-trifluoromethyl-phenyl)-3-{4-[(2-methoxy-ethylamino)-methyl-1H-pyrazolo[3,4-d]pyrimidin-3-yl]-phenyl}-urea Prepared as described above in Example 29 starting from [3-(4-amino-phenyl)-1-methyl-1H-pyrazolo[3,4-d]pyrimidin-6-yl]-(2-methoxy-ethyl)-amine and 2-fluoro-5-trifluoromethyl-phenyl isocyanate to give the title compound 1-(2-Fluoro-5-trifluoromethyl-phenyl)-3-{4-[(2-methoxy-ethylamino)-methyl-1H-pyrazolo[3,4-d]pyrimidin-3-yl]-phenyl}-urea as its TFA salt; LC/MS (m/e)=504.0 (MH+), Rt=2.29 min.

Example 33

Preparation of 1-{4-[(2-Diethylamino-ethylamino)-methyl-1H-pyrazolo[3,4-d]pyrimidin-3-yl]-phenyl}-3-(2-fluoro-5-trifluoromethyl-phenyl)-urea Prepared as described above in Example 29 starting from N-[3-(4-amino-phenyl)-1-methyl-1H-pyrazolo[3,4-d]pyrimidin-6-yl]-N',N'-diethyl-ethane-1,2-diamine. and 2-fluoro-5-trifluoromethyl-phenyl isocyanate to give the title compound 1-{4-[(2-Diethylamino-ethylamino)-methyl-1H-pyrazolo[3,4-d]pyrimidin-3-yl]-phenyl}-3-(2-fluoro-5-trifluoromethyl-phenyl)-urea as its TFA salt; LC/MS (m/e)=545.0 (MH+), Rt=2.07 min.

Example 34

Preparation of 1-{4-[(4-Diethylamino-butylamino)-methyl-1H-pyrazolo[3,4-d]pyrimidin-3-yl]-phenyl}-3-(2-fluoro-5-trifluoromethyl-phenyl)-urea Prepared as described above in Example 29 starting from N-[3-(4-amino-phenyl)-1-methyl-1H-pyrazolo[3,4-d]pyrimidin-6-yl]-N',N'-diethyl-butane-1,2-diamine. and 2-fluoro-5-trifluoromethyl-phenyl isocyanate to give the title compound 1-{4-[(4-Diethylamino-butylamino)-methyl-1H-pyrazolo[3,4-d]pyrimidin-3-yl]-phenyl)-}-3-(2-fluoro-5-trifluoromethyl-phenyl)-urea as its TFA salt; LC/MS (m/e)=573.2 (MH+), Rt=2.02 min.

Example 35

Preparation of 1-(5-tert-Butyl-isoxazol-3-yl)-3-{4-[1-methyl-6-(2-morpholin-4-yl -ethylamino)-1H-pyrazolo[3,4-d]]pyrimidin-3-yl]-phenyl}-urea To the solution of [3-(4-amino-phenyl)-1-methyl-1H-pyrazolo[3,4-d]pyrimidin-6-yl]-(2-morpholin-4-yl-ethyl)-amine (110 mg, 0.31 mmol) in 5 mL of anhydrous THF was added (5-tert-butyl-isoxazol-3-yl)-carbamic acid phenyl ester (96 mg, 0.37 mmol, 1.2 eq) followed by triethylamine (37 mg, 0.37 mmol, 1.2 eq). The reaction mixture was heated under reflux for 16 hours, then evaporated. Crude product was purified column chromatography (MeOH) to give 82 mg of pure 1-(5-tert-butyl -isoxazol-3-yl)-3-{4-[1-methyl-6-(2-morpholin-4-yl-ethylamino)-1H-pyrazolo[3,4-d]]pyrimidin-3-yl]-phenyl}-urea; LC/MS (m/e)=520.4 (MH+), Rt=2.16 min.

Example 36

Preparation of 1-{4-[1-Methyl-6-(2-morpholin-4-yl-ethylamino)-1H-pyrazolo[3,4-d]pyrimidin-3-yl]-phenyl}-3-(3-trifluoromethyl-phenyl)-thiourea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 3-trifluoromethyl-phenylthioisocyanate to give the title compound 1-{4-[1-methyl-6-(2-morpholin-4-yl-ethylamino)-1H-pyrazolo[3,4-d]pyrimidin-3-yl]-phenyl}-3-(3-trifluoromethyl-phenyl)-thiourea as its TFA salt; LC/MS (m/e)=557.4 (MH+), Rt=1.75 min.

Example 37

Preparation of 1-(Chloro-trifluoromethyl-phenyl)-3-{4-[methyl-(2-morpholin-4-yl -ethylamino)-1H-pyrazolo[3,4-d]pyrimidin-3-yl]-phenyl}-urea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 2-chloro-5-trifluoromethyl -phenylisocyanate to give the title compound 1-(chloro-trifluoromethyl-phenyl)-3-{4-[methyl-(2-morpholin-4-yl-ethylamino)-1H-pyrazolo[3,4-d]pyrimidin-3-yl]-phenyl}-urea as its TFA salt; LC/MS (m/e)=574.8 (MH+), Rt=2.12 min.

Example 38

Preparation of 1-(3-Ethyl-phenyl)-3-{4-[1-methyl-6-(2-morpholin-4-yl-ethylamino) -1H-pyrazolo[3,4-d]pyrimidin-3-yl]-phenyl}-urea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 3-ethylphenylisocyanate to give the title compound 1-(3-ethyl-phenyl)-3-{4-[1-methyl -6-(2-morpholin-4-yl-ethylamino)-1H-pyrazolo[3,4-d]pyrimidin-3-yl]-phenyl}-urea as its TFA salt; LC/MS (m/e)=501.2 (MH+), Rt=1.65 min.

Example 39

Preparation of 1-{4-[1-Methyl-6-(2-morpholin-4-yl-ethylamino)-1H-pyrazolo[3,4-d]pyrimidin-3-y]-phenyl}-3-naphthalen-2-yl-urea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 2-napthylisocyanate to give the title compound 1-{4-[1-methyl-6-(2-morpholin-4-yl -ethylamino)-1H-pyrazolo[3,4-d]pyrimidin-3-yl]-phenyl }-3-naphthalen-2-yl-urea as its TFA salt; LC/MS (m/e)=523.2 (MH+), Rt=1.87 min.

Example 40

Preparation of 1-(3-Acetyl-phenyl)-3-{4-[1-methyl-6-(2-morpholin-4-yl -ethylamino)-1H-pyrazolo[3,4-d]pyrimidin-3-yl]-phenyl}-urea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 3-acetylphenylisocyanate to give the title compound 1-(3-acetyl-phenyl)-3-{4-[1-methyl-6-(2-morpholin-4-yl-ethylamino)-1H-pyrazolo[3,4-d]pyrimidin-3-yl]-phenyl}-urea as its TFA salt; LC/MS (m/e)=514.6 (MH+), Rt=1.60 min.

Example 41

Preparation of 1-(Bis-trifluoromethyl-phenyl)-3-{4-[1-methyl-6-(2-morpholin-4-yl -ethylamino)-1H-pyrazolo[3,4-d]pyrimidin-3-yl]-phenyl}-urea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 3,5-bistrofluoromethylphenylisocyanate to give the title compound 1-(bis -trifluoromethyl-phenyl)-3-{4-[1-methyl-6-(2-morpholin-4-yl-ethylamino) -1H-pyrazolo[3,4-d]pyrimidin-3-yl]-phenyl}-urea as its TFA salt; LC/MS (m/e)=609.4 (MH+), Rt=2.04 min.

Example 42

Preparation of 1-{4-[1-Methyl-6-(2-morpholin-4-yl-ethylamino)-1H-pyrazolo[3,4-d]pyrimidin-3-yl]-phenyl}-3-(3-trifluoromethyl-phenyl)-urea Prepared as described above in Example 29 starting from [3-(4-amino-phenyl)-1-methyl-1H-pyrazolo[3,4-d]pyrimidin-6-yl]-(2-morpholin-4-yl-ethyl)-amine and 3-trifluoromethylphenylisocyanate to give the title compound 1-{4-[1-methyl-6-(2-morpholin-4-yl-ethylamino)-1H-pyrazolo[3,4-d]pyrimidin-3-yl]-phenyl}-3-(3-trifluoromethyl-phenyl)-urea as its TFA salt; LC/MS (m/e)=541.4 (MH+), Rt=1.82 min.

Example 43

Preparation of 1-(2-Fluoro-5-trifluoromethyl-phenyl)-3-{methyl-[methyl-(2-morpholin-4-yl-ethylamino)-1H-pyrazolo[3,4-d]pyrimidin-3-yl]-phenyl}-urea Prepared as described above in Example 29 starting from [3-(4-amino-3-methyl -phenyl)-1-methyl-1H-pyrazolo[3,4-d]pyrimidin-6-yl]-(2-morpholin-4-yl-ethyl) -amine and 2-fluoro-5-trifluoromethylphenylisocyanate to give the title compound 1-(2-fluoro-5-trifluoromethyl-phenyl)-3-{methyl-[methyl-(2-morpholin-4-yl -ethylamino)-1H-pyrazolo[3,4-d]pyrimidin-3-yl]-phenyl}-urea as its TFA salt; LC/MS (m/e)=573.2 (MH+), Rt=1.90 min.

Example 44

Preparation of 1-(Chloro-trifluoromethyl-phenyl)-3-{methyl-[methyl-(2-morpholin- 4-yl-ethylamino)-1H-pyrazolo[3,4-d]pyrimidin-3-yl]-phenyl}-urea Prepared as described above in Example 29 starting from [3-(4-amino-3-methyl -phenyl)-1-methyl-1H-pyrazolo[3,4-d]pyrimidin-6-yl]-(2-morpholin-4-yl-ethyl) -amine and 2-chloro-5-trifluoromethylphenylisocyanate to give the title compound 1-(chloro-trifluoromethyl-phenyl)-3-{methyl-[methyl-(2-morpholin-4-yl -ethylamino)-1H-pyrazolo[3,4-d]pyrimidin-3-yl]-phenyl}-urea as its TFA salt; LC/MS (m/e)=589.0 (MH+), Rt=2.00 min.

Example 45

Preparation of 1-(3-Ethyl-phenyl)-3-{2-methyl-4-[1-methyl-6-(2-morpholin-4-yl -ethylamino)-1H-pyrazolo[3,4-d]pyrimidin-3-yl]-phenyl}-urea Prepared as described above in Example 29 starting from [3-(4-amino-3-methyl -phenyl)-1-methyl-1H-pyrazolo[3,4-d]pyrimidin-6-yl]-(2-morpholin-4-yl-ethyl) -amine and 3-ethylphenylisocyanate to give the title compound 1-(3-ethyl-phenyl)-3-{2-methyl-4-[1-methyl-6-(2-morpholin-4-yl-ethylamino)-1H-pyrazolo[3,4-d]pyrimidin-3-yl]-phenyl}-urea as its TFA salt; LC/MS (m/e)=515.4 (MH+), Rt=1.80 min.

Example 46

Preparation of 1-{2-Methyl-4-[1-methyl-6-(2-morpholin-4-yl-ethylamino)-1H -pyrazolo[3,4-d]pyrimidin-3-yl]-phenyl}-3-naphthalen-2-yl-urea Prepared as described above in Example 29 starting from [3-(4-amino-3-methyl -phenyl)-1-methyl-1H-pyrazolo[3,4-d]pyrimidin-6-yl]-(2-morpholin-4-yl-ethyl) -amine and 2-naphthylisocyanate to give the title compound 1-(3-ethyl-phenyl)-3-{2-methyl-4-[1-methyl-6-(2-morpholin-4-yl-ethylamino)-1H-pyrazolo[3,4-d]pyrimidin -3-yl]-phenyl}-urea as its TFA salt; LC/MS (m/e)=537.2 (MH+), Rt=1.92 min.

Example 47

Preparation of 1-(Bis-trifluoromethyl-phenyl)-3-{methyl-[methyl-(2-morpholin-4-yl -methylamino)-1H-pyrazolo[3,4-d]pyrimidin-3-yl]-phenyl}-urea Prepared as described above in Example 29 starting from [3-(4-amino-3-methyl -phenyl)-1-methyl-1H-pyrazolo[3,4-d]pyrimidin-6-yl]-(2-morpholin-4-yl-ethyl )-amine and 3,5-bistrifluoromethylphenylisocyanate to give the title compound 1-(bis -trifluoromethyl-phenyl)-3-{methyl-[methyl-(2-morpholin-4-yl-methylamino)-1H -pyrazolo[3,4-d]pyrimidin-3-yl]-phenyl}-urea as its TFA salt; LC/MS (m/e)=623.0 (MH+), Rt=2.14 min.

Example 48

Preparation of 1-{2-Methyl-4-[methyl-(2-morpholin-4-yl-ethylamino)-1H -pyrazolo[3,4-d]pyrimidin-3-yl]-phenyl}-3-(3-trifluoromethyl-phenyl)-urea Prepared as described above in Example 29 starting from [3-(4-amino-3-methyl -phenyl)-1-methyl-1H-pyrazolo[3,4-d]pyrimidin-6-yl]-(2-morpholin-4-yl-ethyl) -amine and 3-trifluoromethylphenylisocyanate to give the title compound 1-{2-Methyl-4-[methyl-(2-morpholin-4-yl-ethylamino)-1H-pyrazolo[3,4-d]pyrimidin-3-yl]-phenyl}-3-(3-trifluoromethyl-phenyl)-urea as its TFA salt; LC/MS (m/e)=555.2 (MH+), Rt=1.85 min.

Example 49

Preparation of 1-{2-Fluoro-[methyl-(2-morpholin-4-yl-ethylamino)-1H-pyrazolo[3,4-d]]pyrimidin-3-yl]-phenyl}-3-(2-fluoro-5-trifluoromethyl-phenyl)-urea Prepared as described above in Example 29 starting from [3-(4-amino-3-fluoro -phenyl)-1-methyl-1H-pyrazolo[3,4-d]pyrimidin-6-yl]-(2-morpholin-4-yl-ethyl) -amine and 2-fluoro-5-trifluoromethyl-phenylisocyanate to give the title compound 1-{2-fluoro-[methyl-(2-morpholin-4-yl-ethylamino)-1H-pyrazolo[3,4-d]pyrimidin-3-yl]-phenyl}-3-(2-fluoro-5-trifluoromethyl-phenyl)-urea as its TFA salt; LC/MS (m/e)=577.2 (MH+), Rt=2.47 min.

Example 50

Preparation of 1-{4-[Benzyl-(2-morpholin-4-yl-ethylamino)-1H-pyrazolo[3,4-d]pyrimidin-3-yl]-phenyl}-3-(fluoro-trifluoromethyl-phenyl)-urea Prepared as described above in Example 29 starting from [3-(4-amino-phenyl)-1-benzyl-1H-pyrazolo[3,4-d]pyrimidin-6-yl]-(2-morpholin-4-yl-ethyl)-amine and 2-fluoro-5-trifluoromethyl-phenyl isocyanate to give the title compound 1-{4-[benzyl-(2-morpholin-4-yl-ethylamino)-1H-pyrazolo[3,4-d]pyrimidin-3yl]-phenyl}-3-(fluoro-trifluoromethyl-phenyl)-urea as its TFA salt; LC/MS (m/e)=635.2 (MH+), Rt=2.12 min.

Example 51

Preparation of 1-{4-[Benzyl-(2-morpholin-4-yl-ethylamino)-1H-pyrazolo[3,4-d]pyrimidin-3-yl]-phenyl}-3-(fluoro-trifluoromethyl-phenyl)-thiourea Prepared as described above in Example 29 starting from [3-(4-amino-phenyl)-1-benzyl-1H-pyrazolo[3,4-d]pyrimidin-6-yl]-(2-morpholin-4-yl-ethyl)-amine and 3-trifluoromethyl-phenylthioisocyanate to give the title compound 1-{4-[benzyl-(2-morpholin-4-yl-ethylamino)-1H-pyrazolo[3,4-d]pyrimidin-3-yl]-phenyl}-3-(fluoro-trifluoromethyl-phenyl)-thiourea as its TFA salt; LC/MS (m/e)=633.2 (MH+), Rt=1.95 min.

Example 52

Preparation of 1-{4-[Benzyl-(2-morpholin-4-yl-ethylamino)-1H-pyrazolo[3,4-d]pyrimidin-3-yl]-phenyl}-3-(ethyl-phenyl)-urea Prepared as described above in Example 29 starting from [3-(4-amino-phenyl)-1-benzyl-1H-pyrazolo[3,4-d]pyrimidin-6-yl]-(2-morpholin-4-yl-ethyl)-amine and 3-ethyl-phenyl isocyanate to give the title compound 1-{4-[benzyl-(2-morpholin-4-yl-ethylamino)-1H-pyrazolo[3,4-d]pyrimidin-3-yl]-phenyl}-3-(ethyl-phenyl)-urea as its TFA salt; LC/MS (m/e)=577.3 (MH+), Rt=1.89 min.

Example 53

Preparation of 1-(3,5-Bis-trifluoromethyl-phenyl)-3-{2-fluoro-[methyl-(2-morpholin-4-yl-ethylamino)-1H-pyrazolo[3,4-d]pyrimidin-3-yl]-phenyl}-urea Prepared as described above in Example 29 starting from [3-(4-amino-3-fluoro-phenyl)-1-methyl-1H-pyrazolo[3,4-d]pyrimidin-6-yl]-(2-morpholin-4-yl-ethyl)-amine and 3,5-bistrifluoromethyl-phenylisocyanate to give the title compound 1-(3,5-bbs-trifluoromethyl-phenyl)-3-{2-fluoro-[methyl-(2-morpholin-4-yl-ethylamino)-1H-pyrazolo[3,4-d]pyrimidin-3-yl]-phenyl}-urea as its TFA salt; LC/MS (m/e)=627.2 (MH+), Rt=2.20 min.

Example 54

Preparation of 1-(3-Acetyl-phenyl)-3-{2-fluoro-4-[1-methyl-6-(2-morpholin-4-yl-ethylamino)-1H-pyrazolo[3,4-d]pyrimidin-3-yl]-phenyl}-urea Prepared as described above in Example 29 starting from [3-(4-amino-3-fluoro-phenyl)-1-methyl-1H-pyrazolo[3,4-d]pyrimidin-6-yl]-(2-morpholin-4-yl-ethyl)-amine and 3-acetyl-phenylisocyanate to give the title compound 1-(3-Acetyl-phenyl)-3-{2-fluoro-4-[1-methyl-6-(2-morpholin-4-yl-ethylamino)-1H-pyrazolo[3,4-d]pyrimidin-3-yl]-phenyl}-urea as its TFA salt; LC/MS (m/e)=533.2 (MH+), Rt=1.64 min.

Example 55

Preparation of 1-{2-Fluoro-4-[1-methyl-6-(2-morpholin-4-yl-ethylamino)-1H-pyrazolo[3,4-d]pyrimidin-3-yl]-phenyl]}-3-naphthalen-2-yl-urea Prepared as described above in Example 29 starting from [3-(4-amino-3-fluoro-phenyl)-1-methyl-1H-pyrazolo[3,4-d]pyrimidin-6-yl]-(2-morpholin-4-yl-ethyl)-amine and 2-nepthylisocyanate to give the title compound 1-{2-fluoro-4-[1-methyl-6-(2-morpholin-4-yl-ethylamino)-1H-pyrazolo[3,4-d]pyrimidin-3-yl]-phenyl]}-3-naphthalen-2-yl-urea as its TFA salt; LC/MS (m/e)=541.4 (MH+), Rt=2.17 min.

Example 56

Preparation of 1-(2-Fluoro-5-trifluoromethyl-phenyl)-3-{[methyl-(2-morpholin-4-yl-ethylamino)-1H-pyrazolo[3,4-d]pyrimidin-3-yl]-(2-trifluoromethyl-phenyl)}-urea Prepared as described above in Example 29 starting from {[(amino-trifluoromethyl-phenyl)-methyl-1H-pyrazolo[3,4-d]pyrimidin-6-yl]-(2-morpholin-4-yl-ethyl)-amine and 2-fluoro-5-trifluoromethyl-phenylisocyanate to give the title compound 1-(2,5-fluoro-trifluoromethyl-phenyl)-3-{[methyl-(2-morpholin-4-yl-ethylamino)-1H-pyrazolo[3,4-d]pyrimidin-3-yl]-(2-trifluoromethyl-phenyl)}-urea as its TFA salt; LC/MS (m/e)=627.0 (MH+), Rt=2.49 min.

Example 57

Preparation of 1-(5-tert-Butyl-isoxazol-3-yl)-3-{2-fluoro-4-[1-methyl-6-(2-morpholin-4-yl-ethylamino)-1H-pyrazolo[3,4-d]pyrimidin-3-yl]-phenyl}-urea Prepared as described above in Example 35 starting from [3-(4-amino-3-fluoro-phenyl)-1-methyl-1H-pyrazolo[3,4-d]pyrimidin-6-yl)-(2-morpholin-4-yl-ethyl)-amine to give the title compound 1-(5-tert-butyl-isoxazol-3-yl)-3-{2-fluoro-4-{1-methyl-6-(2-morpholin-4-yl-ethylamino)-1H-pyrazolo[3,4-d]]pyrimidin-3-yl]-phenyl)-urea as its TFA salt; $^1$H-NMR (DMSO): • 1.30 (s, 9H), 2.45 (m, 8H), 3.58 (m, 4H), 3.84 (s, 3H), 6.52 (s, 1H), 6.75 (m, 1H), 7.12 (m, 1H), 7.82 (m, 2H), 8.30 (m, 1H), 8.98 (s, 1H), 9.32 (s, 1H), 9.91 (s, 1H); LC/MS (m/e)=538.2 (MH+), Rt=1.90 min.

Example 58

Preparation of 1-{2-Methyl-4-[1-methyl-6-(2-morpholin-4-yl-ethylamino)-1H-pyrazolo[3,4-d]-pyrimidin-3-yl]-phenyl }-3-(3-trifluoromethyl-phenyl)-thiourea Prepared as described above in Example 29 starting from [3-(4-amino-3-methyl-phenyl)-1-methyl-1H-pyrazolo[3,4-d]pyrimidin-6-yl]-(2-morpholin-4-yl-ethyl)-amine and 3-trifluoromethylphenylthioisocyanate to give the title compound 1-{2-methyl-4-[1-methyl-6-(2-morpholin-4-yl-ethylamino)-1H-pyrazolo[3,4-d]-pyrimidin-3-yl]-phenyl}-3-(3-trifluoromethyl-phenyl)-thiourea as its TFA salt; LC/MS (m/e)=571.2 (MH+), Rt=1.77 min.

Example 59

Preparation of 4-(1-methyl-6-methylsulfanyl-1H-pyrazolo[3,4-d]pyrimidin-3-yl) -phenylamine To a solution of 3-bromo-1-methyl-6-methylsulfanyl-1H-pyrazolo[3,4-d]pyrimidine (2.6 g, 10 mmol) in dioxane (40 mL) and H$_2$O (20 mL) was added anhydrous potassium carbonate (4.14 g, 30 mmol, 3 eq), followed by 4-(4,4,5,5-tetramethyl-1,3,2-dioxaborolan-2-yl)aniline (3.28 g, 15 mmol, 1.5 eq). The reaction mixture was degassed and tetrakis(triphenylphosphine)palladium (58 mg, 0.5 mmol, 0.05 eq) was added. The system was then heated under reflux for 24 hours and cooled to room temperature. The mixture was treated with water (150 mL) and cooled to 0° C. and allowed to sit for three hours. The resulting mixture was then filtered. The filtrate was dried in a vacuum oven overnight to afford 1.66 g (61% yield) of 4-(1-methyl-6-methylsulfanyl-1H-pyrazolo[3,4-d]pyrimidin-3-yl)-phenylamine; $^1$H-NMR (CDCl$_3$): • 2.69 (s, 3H), 3.90 (br s, 2H), 4.08 (s, 3H), 6.82 (d, 2H), 7.77 (d, 2H), 9.11 (s, 1H); LC/MS (m/e)=272.4 (MH+). Rt=1.57 min.

Example 60

Preparation of {4-(1-Methyl-6-methylsulfonyl-1H-pyrazolo[3,4-d]pyrimidin-3-yl -phenyl}carbamic acid tert-butylester To the solution of 4-(1-methyl-6-methylsulfanyl-1H-pyrazolo[3,4-d]pyrimidin-3-yl) -phenylamine (680 mg, 2.4 mmol) in 10 mL of anhydrous 1,4-Dioxane was added Di-tert-butyl dicarbonate (791 mg, 3.6 mmol, 1.5 eq). The reaction mixture was heated to 60° C. for 24 hours, then 0.5 eq more Di-tert-butyl dicarbonate was added. After 18 hours the reaction was cooled to room temperature, the solvent was removed, and the crude reaction mixture was triturated with hexanes and filtered to give a pale brown solid (830 mg, 91% yield) of [4-(1-Methyl-6-methylsulfanyl-1H-pyrazolo[3,4-d]pyrimidin-3-yl-phenyl carbamic acid tert-butylester; LC/MS (m/e)=372.5 (MH+).

To a solution of [4-(1-Methyl-6-methylsulfanyl-1H-pyrazolo[3,4-d]pyrimidin-3-yl -phenyl]carbamic acid tert-butylester (830 mg, 2.2 mmol) in 20 mL methylene chloride was added 3-chloro peroxybenzoic acid (827 mg, 4.8 mmol). The reaction was stirred for 4 hours, at which time 1 mmol more 3-chloro peroxybenzoic acid was added. After 2 hours the reaction was diluted with methylene chloride and washed with concentrated aq. NaHCO$_3$ and Brine. The organic layer was dried over MgSO$_4$, filtered, and concentrated. The final product was obtained via column chromatography (0–5% methanol/methylene chloride) to give [4-(1-Methyl-6-methylsulfonyl-1H-pyrazolo[3,4-d]pyrimidin-3-yl-phenyl]carbamic acid tert-butylester (600 mg, 1.4 mmol) as a pale green solid; $^1$H-NMR (CDCl$_3$): • 1.58 (s, 9H), 3.8 (s, 3H), 4.23 (s, 3H), 6.67 (s, 1H), 7.60 (d, 2H), 7.92 (d, 2H), 9.46 (s, 1H); LC/MS (m/e)=404.46 (MH+).

Example 61

Preparation of 1-(2-fluoro-5-trifluoromethyl-phenyl)-3-(4-{methyl-6-(2-oxopyrrolidin-2-yl)-1H-pyrazolo[3,4-d]pyrimidin-3-yl}-phenyl)-urea To a solution of [4-(1-Methyl-6-methylsulfonyl-1H-pyrazolo[3,4-d]pyrimidin-3-yl -phenyl]carbamic acid tert-butyl ester (162 mg, 0.4 mmol) in 1-methyl-2-pyrrolidinone (2 mL) was added 1-(3-aminopropyl)-2-pyrrolidinone (112 uL, 0.8 mmol, 2 eq) and the reaction mixture was heated to 50° C. After 2 hour, water (20 mL) was added, followed by methylene chloride (20 mL). The layers were separated. The organic layer was washed with water and brine, dried over MgSO$_4$, filtered and evaporated: LC/MS (m/e)=466.2 (MH+), Rt=2.05 min.

The crude material was dissolved in 10 mL trifluoroacetic acid and stirred at room temperature for 1 hour. The TFA was removed, and the resultant solid was azeotroped with toluene the give 1-{3-[3-(4-Amino-phenyl)-1-methyl-1H-pyrazolo[3,4-d]pyrimidin-6-ylamino]-propyl }-pyrrolidin-2-one; Analytical HPLC (Zorbax, C18) Rt=3.515 min, LC/MS (m/e)=366.44 (MH+).

To a solution of 1-{3-[3-(4-Amino-phenyl)-1-methyl-1H-pyrazolo[3,4-d]pyrimidin -6-ylamino]-propyl}-pyrrolidin-2-one (30 mg, 0.08 mmol) in DCM (1 mL) was added 2-fluoro-5-trifluoromethyl-phenyl isocyanate (22 mg, 0.11 mmol) and 2 drops Hunigs base. The reaction mixture was stirred for 1 hour at room temperature while monitored by TLC. The mixture was then evaporated and the crude product was purified by prep. HPLC to give pure 1-(2-fluoro-5-trifluoromethyl-phenyl)-3-(4-{methyl-6-(2-oxopyrrolidin-2-yl)-1H-pyrazolo[3,4-d]pyrimidin-3-yl}-phenyl)-urea as its TFA salt; LC/MS (m/e)=490.2 (MH+), Rt=2.15.

Example 62

Preparation of 1-(2-fluoro-5-trifluoromethyl-phenyl)-3-{4-[1-methyl-6-(benzylamino)-1H-pyrazolo[3,4-d]pyrimidin-3-yl]-phenyl}-urea Prepared as described above in Example 61 starting from [4-(1-Methyl-6-methylsulfonyl-1H-pyrazolo[3,4-d]pyrimidin-3-yl-phenyl]carbamic acid tert-butyl ester and benzyl amine to provide the title compound 1-(2-fluoro-5-trifluoromethyl-phenyl)-3-{4-[1-methyl-6-(benzylamino)-1H-pyrazolo[3,4-d]pyrimidin-3-yl]-phenyl }-urea as its TFA salt; LC/MS (m/e)=536.0 (MH+), Rt=2.6 min.

Example 63

Preparation of 1-(2-fluoro-5-trifluoromethyl-phenyl)-3-{4-[1-methyl-6-(3-chloroanilino)-1H-pyrazolo[3,4-d]pyrimidin-3-yl[-phenyl}-urea Prepared as described above in Example 61 starting from [4-(1-Methyl-6-methylsulfonyl-1H-pyrazolo[3,4-d]pyrimidin-3-yl-phenyl]carbamic acid tert-butyl ester and 3-chloro aniline to provide the title compound 1-(2-fluoro-5-trifluoromethyl-phenyl) -3-{4-[1methyl-6-(3 -chloroanilino)-1H-pyrazolo[3,4-d]pyrimidin-3-yl]-phenyl }-urea as its TFA salt; LC/MS (m/e)=565.0 (MH+), Rt=2.99 min.

Example 64

Preparation of 1-(2-fluoro-5-trifluoromethyl-phenyl)-3-(4-methyl -[3-(4-methyl -piperazine-1-yl)-propylamino]-1H-pyrazolo[3,4-d]pyrimidin-3-yl]-phenyl}-urea Prepared as described above in Example 61 starting from [4-(1-Methyl-6-methylsulfonyl-1H-pyrazolo[3,4-d]pyrimidin-3-yl-phenyl] carbamic acid tert-butyl ester and 4-methyl-1-propylamino piperazine to provide the title compound 1-(2-fluoro-5-trifluoromethyl-phenyl)-3-(4-methyl-[3-(4-methyl-piperazine-1-yl)-propylamino]-1H-pyrazolo

Example 65

Preparation of 1-(2-fluoro-5-trifluoromethyl-phenyl)-3-(4-[methyl-(1-methyl -piperidin-4-ylamino]-1H-pyrazolo[3,4-d]pyrimidin-3-yl]-phenyl}-urea Prepared as described above in Example 61 starting from [4-(1-Methyl-6-methylsulfonyl-1H-pyrazolo[3,4-d]pyrimidin-3-yl-phenyl]carbamic acid tert-butyl ester and methyl -piperidine-4-ylamine to provide the title compound 1-(2-fluoro-5-trifluoromethyl -phenyl)-3-(4-[methyl-(1-methyl-piperidin-4-ylamino)-propylamino]-1H-pyrazolo[3,4-d]pyrimidin-3-yl]-phenyl}-urea as its TFA salt; LC/MS (m/e)=543.5 (MH+).

Example 66

Preparation of 2,5-Dichloro-{4-{1-methyl-6-[3-(4-methyl-piperazin-1yl) -propylamino]-1H-pyrazolo[3,4-d]pyrimidin-3-yl}-phenyl}-thiophene-3-sulfonamide Prepared as described above in Example 61 starting with [4-(6-Amino-1-methyl-1H-pyrazolo[3,4-d]pyrimidin-3-yl-phenyl]carbamic acid tert-butyl ester, 4-methyl-1-propylamino piperazine and 2,5-dichloro thiophene-3-sulfonylchloride to provide the title compound 2,5-Dichloro-{4-{1-methyl-6-[3-(4-methyl-piperazin-1yl) -propylamino]-1H-pyrazolo[3,4-d]pyrimidin-3-yl}-phenyl}-thiophene-3-sulfonamide as its TFA salt; LC/MS (m/e)=547.4 (MH+).

Example 67

Preparation of 2,3-Dichloro-N-{4-(1-methyl-6-(2-oxopyrrolidin-2-yl)-1H-pyrazolo[3,4-d]pyrimidin-3-yl}-phenyl}-benzenesulfonamide To a solution of [4-(1-Methyl-6-methylsulfonyl-1H-pyrazolo[3,4-d]pyrimidin-3-yl-phenyl]carbamic acid tert-butyl ester (162 mg, 0.4 mmol) in 1-methyl-2-pyrrolidinone (2 mL) was added 1-(3-aminopropyl)-2-pyrrolidinone (112 uL, 0.8 mmol, 2 eq) and the reaction mixture was heated to 50° C. After 2 hour, water (20 mL) was added, followed by DCM (20 mL). The layers were separated. The organic layer was washed with water and brine, dried over MgSO$_4$, filtered and evaporated: LC/MS (m/e)=466.2 (MH+), Rt=2.05 min.

The crude material was dissolved in 10 mL trifluoroacetic acid and stirred at room temperature for 1 hour. The TFA was removed, and the resultant solid was azeotroped with toluene the give 1-{3-[3-(4-Amino-phenyl)-1-methyl-1H-pyrazolo[3,4-d]pyrimidin-6-ylamino]-propyl}-pyrrolidin-2-one; HPLC (Zorbax, C18) Rt=3.515, LC/MS (m/e)=366.44 (MH+).

To a solution of 1-{3-[3-(4-Amino-phenyl)-1-methyl-1H-pyrazolo[3,4-d]pyrimidin -6-ylamino]-propyl}-pyrrolidin-2-one (30 mg, 0.08 mmol) in DCM (1 mL) was added 2,3-Dichlorophenylsulfonyl chloride (27 mg, 0.11 mmol) and 2 drops Hunigs base. The reaction mixture was stirred for 1 hour at room temperature while monitored by TLC. The mixture was then evaporated and the crude product was purified by prep. HPLC to give 2,3-Dichloro-N-{4-(1-methyl-6-(2-oxopyrrolidin-2-yl)-1H-pyrazolo[3,4-d]pyrimidin-3-yl)-phenyl}-benzenesulfonamide as its TFA salt. LC/MS (m/e)=574.0 (MH+), Rt=2.12 min.

Example 68

Preparation of 2,3-Dichloro-{4-{1-methyl-6-[1-methyl-piperadin-4-ylamino) -propylamino]-1H-pyrazolo[3,4-d]pyrimidin-3-yl}-phenyl}-benzenesulfonamide Prepared as described above in Example 67 starting with [4-(6-Amino-1-methyl-1H -pyrazolo[3,4-d]pyrimidin-3-yl-phenyl]carbamic acid tert-butyl ester and 1-methyl -piperidine-4-ylamine to provide the title compound 2,3-Dichloro-{4-{1-methyl-6-[1-methyl-piperadin-4-ylamino)-propylamino]-1H-pyrazolo[3,4-d]pyrimidin-3-yl}-phenyl}-benzenesulfonamide as its TFA salt; LC/MS (m/e)=546.0 (MH+), Rt=1.89 min.

Example 69

Preparation of [4-(6-Amino-1-methyl-1H-pyrazolo[3,4-d]pyrimidin-3-yl-phenyl]carbamic acid tert-butyl ester To a solution of [4-(1-Methyl-6-methylsulfonyl-1H-pyrazolo[3,4-d]pyrimidin-3-yl -phenyl]carbamic acid tert-butyl ester (140 mg, 0.34 mmol) in 1,4-dioxane (5 mL) in a sealable tube was added 5 mL NH$_4$H. The tube was sealed and the reaction mixture was stirred at 100° C. for 18 hours. After cooling to room temperature, the solvent was removed, the resultant solid was dissolved in methylene chloride and washed with water. The organic phase was dried over MgSO4, filtered and concentrated to give the desired [4-(6-Amino-1-methyl-1H-pyrazolo[3,4-d]pyrimidin-3-yl-phenyl]carbamic acid tert-butyl ester; $^1$H-NMR (CDCl$_3$): • 3.9 (s, 3H), 7.45 (d, 2H), 7.70 (d, 2H), 8.77 (s, 1H); LC/MS (m/e)=342.0 (MH+), Rt=1.64 min.

Example 70

Preparation of 1-(2-fluoro-5-trifluoromethyl-phenyl)-3-{4-[6-acetylamino-1-methyl]-1H-pyrazolo[3,4-d]pyrimidin-3-yl]-phenyl}-urea Prepared as described above in Example 61 starting with [4-(6-Amino-1-methyl-1H-pyrazolo[3,4-d]pyrimidin-3-yl-phenyl]carbamic acid tert-butyl ester and acetic anhydride to provide the title compound 1-(2-fluoro-5-trifluoromethyl-phenyl)-3-{4-[6-acetylamino-1-methyl]-1H-pyrazolo[3,4-d]pyrimidin-3-yl]-phenyl}-urea as its TFA salt; LC/MS (m/e)=488.2 (MH+), Rt=2.12 min.

Example 71

Preparation of 2,3-Dichloro-N-{4-(6-(acylamino)-1-methyl)-1H-pyrazolo[3,4-d]pyrimidin-3-yl}-phenyl}-benzenesulfonamide Prepared as described above in Example 67 starting with [4-(6-Amino-1-methyl-1H-pyrazolo[3,4-d]pyrimidin-3-yl-phenyl]carbamic acid tert-butyl ester and acetic anhydride to provide the title compound 2,3-Dichloro-N-{4-(6-(acylamino)-1-methyl)-1H-pyrazolo[3,4-d]pyrimidin-3-yl}-phenyl}-benzenesulfonamide as its TFA salt; LC/MS (m/e)=490.8 (MH+), Rt=1.84 min.

Example 72

Preparation of 3-Chloro-6-methylsulfanyl-1H-pyrazolo[3,4-d]pyrimidine

Prepared as described above in Example 1 starting with 4-chloro-2-methylthio-5-pyrimidinecarboxylate and hydrazine. The synthesis then follows as in Example 2 and 3 to give 3-Chloro-6-methylsulfanyl-1H-pyrazolo[3,4-d]pyrimidine as a pale yellow solid; LC/MS (m/e)=201.2 (MH+), Rt=1.42 min.

Example 73

Preparation of 3-Chloro-1-isopropyl-6-methylsulfanyl-1H-pyrazolo[3,4-d]pyrimidine Triphenylphosphine (387 mg, 1.5 mmol) was dissolved in THF (15 mL) and the solution was cooled to −78° C. Diethyl azodicarboxylate (225 uL, 1.5 mmol) was added slowly to the reaction mixture. The reaction was stirred for 5 min and then isopropanol was added (115 uL, 1.5 mmol) dropwise. After stirring an additional 5 min. the 3-Chloro-6-methylsulfanyl-1H-pyrazolo[3,4-d]pyrimidine (305 mg, 1.6 mmol) was added as a solid. The resulting suspension was kept at −78° C. for 5 min then the cooling bath was removed. The reaction was stirred for 3 hours at room temperature. After concentration the desired 3-Chloro-1-isopropyl-6-methylsulfanyl-1H-pyrazolo[3,4-d]pyrimidine was obtained by column chromatography (0–5% MeOH/methylene chloride); $^1$H-NMR (CDCl$_3$): • 1.46 (d, 1H), 2.66 (s, 3H), 4.53 (q, 6H), 8.87 (s, 1H); LC/MS (m/e)=243.0 (MH+), Rt=2.25 min.

Example 74

Preparation of 3-Chloro-1-isopropyl-6-methylsulfonyl-1H-pyrazolo[3,4-d]pyrimidine Prepared as described above in Example 5 starting with 3-Chloro-1-isopropyl-6-methylsulfanyl-1H-pyrazolo[3,4-d]pyrimidine to provide the title compound; $^1$H -NMR (CDCl$_3$): • 1.37 (d, 1H), 3.37 (s, 3H), 4.44 (q, 6H), 9.16 (s, 1H); LC/MS (m/e)=243.0 (MH+), Rt=2.25 min.

Example 75

Preparation of (3-Chloro-1-isopropyl-1H-pyrazolo[3,4-d]pyrimidin-6-yl)-(2-morpholin-4-yl-ethyl)-amine Prepared as described above in Example 8 starting from 3-chloro-6-methanesulfonyl-1-isopropyl-1H-pyrazolo[3,4-d]pyrimidin-3-one and N -aminoethylmorpholine to give the title compound (3-chloro-1-isopropyl-1H -pyrazolo[3,4-d]pyrimidin-6-yl)-(2-morpholin-4-yl-ethyl)-amine; LC/MS (m/e)=324.81 (MH+). Rt=1.40 min.

Example 76

Preparation of [3-(4-amino-phenyl)-1-isopropyl-1H-pyrazolo[3,4-d]pyrimidin-6-yl]-(2-morpholin-4-yl-ethyl)-amine Prepared as described above in Example 15 starting from (3-chloro-1-methyl-1H -pyrazolo[3,4-d]pyrimidin-6-yl)-(2-morpholin-4-yl-ethyl)-amine and 4-(4,4,5,5-tetramethyl-1,3,2-dioxaborolan-2-yl)aniline to give the title compound [3-(4-amino -phenyl)-1-isopropyl-1H-pyrazolo[3,4-d]pyrimidin-6-yl]-(2-morpholin-4-yl-ethyl) -amine; LC/MS (m/e)=382.2 (MH+), Rt=1.17 min.

Example 77

Preparation of 2,3-Dichloro-N-{4-(1-isopropyl-6-(2-morpholin-4-yl-ether)-1H -pyrazolo[3,4-d]pyrimidin-3-yl}-phenyl}-benzenesulfonamide The [3-(4-amino-phenyl)-1-isopropyl-1H-pyrazolo[3,4-d]pyrimidin-6-yl]-(2-morpholin-4-yl-ethyl)-amine (20 mg, 0.05 mmol) was dissolved in pyridine (1 mL) and the 2,3-Dichlorophenylsulfonyl chloride (15 mg, 0.06 mmol) was added. After 2 hours the crude mixture was purified via prep HPLC to give 2,3-Dichloro-N-{4-(1-methyl-6-(2-morpholin-4-yl-ether)-1H-pyrazolo[3,4-d]pyrimidin-3-yl}-phenyl}-benzenesulfonamide as its TFA salt; LC/MS (m/e)=590.0 (MH+), Rt=2.05 min.

Example 78

Preparation of 1-(2-Fluoro-5-trifluoromethyl-phenyl)-3-{4-[(2-morpholin-4yl -ethyl)-isopropyl-1H-pyrazolo[3,4-d]pyrimidin-3-yl]-phenyl}-urea To a solution of [3-(4-amino-phenyl)-1-isopropyl-1H-pyrazolo[3,4-d]pyrimidin-6-yl]-(2-morpholin-4-yl-ethyl)-amine (20 mg, 0.05 mmol) was dissolved in pyridine (1 mL) and 2-fluoro-5-trifluoromethyl-phenyl isocyanate (22 mg, 0.11 mmol) was added. The reaction mixture was stirred for 2 hour at room temperature. The mixture purified by prep. HPLC to give pure 1-(2-fluoro-5-trifluoromethyl-phenyl)-3-{4-[(2-morpholin-4-yl-ethyl)-isopropyl-1H-pyrazolo[3,4-d]pyrimidin-3-yl]-phenyl)-urea as its TFA salt; LC/MS (m/e)=587.2 (MH+), Rt=2.19 min.

Example 79

Preparation of 4-(6-Methanesulfonyl-1-methyl-1H-pyrazolo[3,4-d]pyrimidin-3-yl) -phenyl amine

[4-(6-Methanesulfonyl-1-methyl-1H-pyrazolo[3,4-d]pyrimidin-3-yl)-phenyl]carbamic acid tert-butyl ester (1.49 g, 3.70 mmol) was treated with TFA (30% in CH$_2$Cl$_2$, 40 ml) at room temperature for 1 hr. Solvent was removed on rotavap and the residual was taken into 5% Na$_2$CO$_3$ (50 ml) and the product was extracted by CH$_2$Cl$_2$×10, the organic extracts were combined and washed by brine, drying and concentration left 750 mg as a light brown solid; LC/MS (m/e)=304 (MH$^+$).

Example 80

Preparation of 1-(2-Fluoro-5-trifluoromethyl-phenyl)-3-{4-[1-methyl-6-methanesulfonyl-1H-pyrazolo[3,4-d]pyrimidin-3-yl)-phenyl]} urea 4-(6-Methanesulfonyl-1-methyl-1H-pyrazolo[3,4-d]pyrimidin-3-yl)-phenyl amine (413 mg, 1.36 mmol) from Example 79 was treated with 2-Fluoro-5-trifluoromethyl phenyl isocyanate (237 µl, 1.2 equiv.) in CH$_2$Cl$_2$ (50 ml) for 16 hrs. The mixture was concentrated on rotavap to about 5 ml and the product was collected by filtration and washed with CH2Cl2 (2×1 ml), gave 370 mg as an off white solid; LC/MS(m/e)=508.8 (MH$^+$).

Example 81

Preparation of 1-(2-Fluoro-5-trifluoromethyl-phenyl)-3-{4-[(1-methyl-6-phenethylamino)-1H-pyrazolo[3,4-d]pyrimidin-3-yl]-phenyl} urea A mixture of 1-(2-Fluoro-5-trifluoromethyl-phenyl)-3-{4-[1-methyl-6-methanesulfonyl-1H-pyrazolo[3,4-d]pyrimidin-3-yl)-phenyl]} urea (25 mg, 0.049 mmol) from Example 80 and phenethylamine (2.5 equiv., 15 μl) in DMF (0.5 ml) was heated at 60° C. for 2 hrs and monitored by LC/MS. The crude reaction mixture was then purified by prep. HPLC to give the title compound as its TFA salt; LC/MS(m/e)=550.0 (MH$^+$), Rt=2.67 min.

Example 82

1-(2-Fluoro-5-trifluoromethyl-phenyl)-3-{4-[(1-methyl-6-(5-hydroxy-pentylamino)-1H-pryrazolo[3,4-d]pyrimidin-3-yl]-phenyl} urea Following the procedure of Example 81, replacing phenethylamine by 5-Amino-pentan-1-ol gave the title compound as its TFA salt; LC/MS(m/e)=532.0 (MH$^+$), Rt =2.19 min.

Example 83

Preparation of 1-(2-Fluoro-5-trifluoromethyl-phenyl)-3-{4-[(1-methyl-6-(2-hydroxy-1-hydroxymethyl-ethylamino)-1H-pyrazolo[3,4-d]pyrimidin-3-yl]-phenyl} urea Following the procedure of Example 81, replacing phenethylamine by serinol gave the title compound as its TFA salt; LC/MS(m/e)=520.2 (MH$^+$), Rt=1.90 min.

Example 84

Preparation of 1-(2-Fluoro-5-trifluoromethyl-phenyl)-3-{4-[(1-methyl-6-(3-morpholin-4-yl-propylamino)-1H-pyrazolo[3,4-d]pyrimidin-3-yl]-phenyl} urea Following the procedure of Example 81, replacing phenethylamine by 4-(3-Aminopropyl)morpholine gave the title compound as its TFA salt; LC/MS(m/e)=573.0 (MH$^+$), Rt=1.89 min.

Example 85

Preparation of 1-(2-Fluoro-5-trifluoromethyl-phenyl)-3-{4-[(1-methyl-6-[3-(2-methyl-piperidin-1-yl)-propylamino]-1H-pyrazolo[3,4-d]pyrimidin-3-yl]-phenyl} urea Following the procedure of Example 81, replacing phenethylamine by 4-(3-Aminopropyl)-2-pipecoline gave the title compound as its TFA salt; LC/MS(m/e)=585.0 (MH$^+$), Rt=2.09 min.

Example 86

Preparation of 1-(2-Fluoro-5-trifluoromethyl-phenyl)-3-{4-[1-methyl-6-(3-pyrrolidin-1-yl)-propylamino]-1H-pyrazolo[3,4-d]pyrimidin-3-yl]-phenyl} urea Following the procedure of Example 81, replacing phenethylamine by 1-(3-Aminopropyl)-pyrrolidine gave the title compound as its TFA salt; LC/MS(m/e)=557.2 (MH$^+$), Rt=2.24 min.

Example 87

Preparation of 1-(2-Fluoro-5-trifluoromethyl-phenyl)-3-{4-[1-methyl-6-(3-dimethylamino-propylamino)-1H-pyrazolo[3,4-d]pyrimidin-3-yl]-phenyl} urea Following the procedure of Example 81, replacing phenethylamine by N,N-dimethyl-1,3-propanediamine gave the title compound as its TFA salt; LC/MS(m/e)=531.2 (MH$^+$).

Example 88

Preparation of 1-(2-Fluoro-5-trifluoromethyl-phenyl)-3-{4-[1-methyl-6-(3-diethylamino-propylamino)-1H-pyrazolo[3,4-d]pyrimidin-3-yl]-phenyl} urea Following the procedure of Example 81, replacing phenethylamine by N,N-diethyl-1,3-propanediamine gave the title compound as its TFA salt; LC/MS(m/e)=559.0 (MH$^+$), Rt=2.04 min.

Example 89

Preparation of 1-(2-Fluoro-5-trifluoromethyl-phenyl)-3-{4-[1-methyl-6-[2-(1-methyl-pyrrolidin-2-yl)-ethylamino]-1H-pyrazolo[3,4-d]pyrimidin-3-yl]-phenyl} urea Following the procedure of Example 81, replacing phenethylamine by 2-(2-Aminoethyl)-1-methylpyrrolidine gave the title compound as its TFA salt; LC/MS(m/e)=557.0 (MH$^+$), Rt=2.04 min.

Example 90

Preparation of 1-(2-Fluoro-5-trifluoromethyl-phenyl)-3-{4-[1-methyl-6-[2-(2-oxo-imidazolidin-1-yl-ethylamino]-1H-pyrazolo[3,4-d]pyrimidin-3-yl]-phenyl} urea Following the procedure of Example 81, replacing phenethylamine by 1-(2-Aminoethyl)-2-imidazolidinone gave the title compound as its TFA salt; LC/MS(m/e)=558.0 (MH$^+$), Rt=2.28 min.

Example 91

Preparation of 1-(2-Fluoro-5-trifluoromethyl-phenyl)-3-{4-[1-methyl-6-[(4-pyrrolidin-1-yl)-butylamino]-1H-pyrazolo[3,4-d]pyrimidin-3-yl]-phenyl} urea Following the procedure of Example 81, replacing phenethylamine by 4-Pyrrolidinobutylamine gave the title compound as its TFA salt; LC/MS(m/e)=571.2 (MH$^+$), Rt=2.14 min.

Example 92

Preparation of 1-(2-Fluoro-5-trifluoromethyl-phenyl)-3-{4-[1-methyl-6-(3-hydroxy-propylamino)-1H-pyrazolo[3,4-d]pyrimidin-3-yl]-phenyl} urea Following the procedure of Example 81, replacing phenethylamine by 3-Amino-1-propanol gave the title compound as its TFA salt; LC/MS(m/e)=504.2 (MH$^+$), Rt=2.22 min.

Example 93

Preparation of 1-(2-Fluoro-5-trifluoromethyl-phenyl)-3-{4-[1-methyl-6-(4-hydroxy-butylamino)-1H-pyrazolo[3,4-d]pyrimidin-3-yl]-phenyl} urea Following the procedure of Example 81, replacing phenethylamine by 4-Amino-1-butanol gave the title compound as its TFA salt; LC/MS(m/e)=518.2 (MH$^+$), Rt=2.10 min.

Example 94

Preparation of 1-(2-Fluoro-5-trifluoromethyl-phenyl)-3-{4-[1-methyl-6-(3-amino-propylamino)-1H-pyrazolo[3,4-d]pyrimidin-3-yl]-phenyl} urea Following the procedure of Example 81, replacing phenethylamine by 1,3-Diaminopropane gave the title compound as its TFA salt; LC/MS(m/e)=503.3 (MH$^+$), Rt=1.91 min.

Example 95

Preparation of 1-(2-Fluoro-5-trifluoromethyl-phenyl)-3-{4-[1-methyl-6-(4-amino-butylamino)-1H-pyrazolo[3,4-d]pyrimidin-3-yl]-phenyl} urea Following the procedure of Example 81, replacing phenethylamine by 1,4-Diaminobutane gave the title compound as its TFA salt; LC/MS(m/e)=517.4 (MH$^+$), Rt=2.07 min.

Example 96

Preparation of N-[3-(3-{4-[3-(2-Fluoro-5-trifluoromethyl-phenyl)-ureido]-phenyl}-1-methyl-1H-pyrazolo[3,4-d]pyrimidin-6-ylamino)-propyl]-methanesulfonamide 1-(2-Fluoro-5-trifluoromethyl-phenyl)-3-{4-[1-methyl-6-(3-amino-propylamino)-1H-pyrazolo[3,4-d]pyrimidin-3-yl]-phenyl} urea from Example 94 was treated with methanesulfonyl chloride in pyridine at room temperature for 2 hrs and monitored by LC/MS. The crude reaction mixture was then purified by prep HPLC to gave the title compound as its TFA salt; LC/MS(m/e)=581.4 (MH$^+$), Rt=2.04 min.

Example 97

Preparation of N-[4-(3-{4-[3-(2-Fluoro-5-trifluoromethyl-phenyl)-ureido]-phenyl} -1-methyl-1H-pyrazolo[3,4-d]pyrimidin-6-ylamino)-butyl]-methanesulfonamide Following the procedure of Example 96, 1-(2-Fluoro-5-trifluoromethyl-phenyl)-3-{4-[1-methyl-6-(4-amino-butylamino)-1H-pyrazolo[3,4-d]pyrimidin-3-yl]-phenyl}urea from Example 17 gave the title compound as its TFA salt; LC/MS(m/e)=595.2 (MH$^+$), Rt=2.08 min.

Example 98

Preparation of 1-(2-Fluoro-5-trifluoromethyl-phenyl)-3-{4-[1-methyl-6-(2-acetylamino-ethylamino))-1H-pyrazolo[3,4-d]pyrimidin-3-yl]-phenyl} urea Following the procedure of Example 81, replacing phenethylamine by N-Acetylethylenediamine gave the title compound as its TFA salt; LC/MS(m/e)=531.2 (MH$^+$), Rt=2.12 min.

Example 99

Preparation of 1-(2-Fluoro-5-trifluoromethyl-phenyl)-3-{4-[1-methyl-6-(4-guanidino-butylamino)-1H-pyrazolo[3,4-d]pyrimidin-3-yl]-phenyl} urea Following the procedure of Example 81, replacing phenethylamine by Agmatine gave the title compound as its TFA salt; LC/MS(m/e)=559.2 (MH$^+$), Rt=1.92 min.

Example 100

Preparation of 1-(2-Fluoro-5-trifluoromethyl-phenyl)-3-{4-[1-methyl-6-(3-imidazol-1-yl-propylamino)-1H-pyrazolo[3,4-d]pyrimidin-3-yl]-phenyl} urea Following the procedure of Example 81, replacing phenethylamine by 1-(3-Aminopropyl)imidazole gave the title compound as its TFA salt; LC/MS(m/e)=554.2 (MH$^+$), Rt=2.05 min.

Example 101

Preparation of 1-(2-Fluoro-5-trifluoromethyl-phenyl)-3-{4-[1-methyl-6-(2-[1-methyl-1H-pyrrol-2-yl]-ethylamino)-1H-pyrazolo[3,4-d]pyrimidin-3-yl]-phenyl} urea Following the procedure of Example 81, replacing phenethylamine by (2-Aminoethyl)-1-methyl pyrrole gave the title compound as its TFA salt; LC/MS(m/e)=553.2 (MH$^+$), Rt=2.49 min.

Example 102

Preparation of 2,3-Dichloro-N-[4-(6-methanesulfonyl-1-methyl-1H-pyrazolo[3,4-d]pyrimidin-3-yl)-phenyl]-benzenesulfonamide 2,3-Dichlorobenzenesulfonyl chloride (342 mg, 1.5 equiv.) was added to a mixture of 4-(6-Methanesulfonyl-1-methyl-1H-pyrazolo[3,4-d]pyrimidin-3-yl)-phenyl amine (283 mg., 0.93 mmol) and DIEA (325 µl, 2 equiv.) in $CH_2Cl_2$ (10 ml) at room temperature. After 2 hrs, the mixture was diluted by $CH_2Cl_2$ (10 ml) and washed by 10% NaHCO3, brine, drying and concentration left 420 mg as a golden yellow solid; LC/MS(m/e)=512.0 ($MH^+$).

Example 103

Preparation of 2,3-Dichloro-N-{4-[1-methyl-6-(3-morpholin-4-yl-propylamino)-1H-pyrazolo[3,4-d]pyrimidin-3-yl)-phenyl}-benzenesulfonamide A mixture of 2,3-Dichloro-N-[4-(6-methanesulfonyl-1-methyl-1H-pyrazolo[3,4-d]pyrimidin-3-yl)-phenyl]-benzenesulfonamide from Example 24 and 4-(3-Aminopropyl)morpholine(2.5 equiv) in DMF (0.5 mL) was heated at 60° C. for 2 hrs and monitored by LC/MS. The crude reaction mixture was then purified by prep HPLC gave the title compound as its TFA salt; LC/MS(m/e)=576.0 ($MH^+$), Rt=1.75 min.

Example 104

Preparation of 2,3-Dichloro-N-(4-{1-methyl-6-[3-(2-methyl-piperidin-1-yl)-propylamino]-1H-pyrazolo[3,4-d]pyrimidin-3-yl)-phenyl}-benzenesulfonamide Following the procedure of Example 103, replacing 4-(3-Aminopropyl)morpholine by by 1-(3-Aminopropyl)-2-pipecoline gave the title compound as its TFA salt; LC/MS(m/e)=588.2 ($MH^+$), Rt=1.79 min.

Example 105

Preparation of 2,3-Dichloro-N-{4-[1-methyl-6-(3-pyrrolidin-1-yl -propylamino)-1H-pyrazolo[3,4-d]pyrimidin-3-yl]-phenyl}-benzenesulfonamide Following the procedure of Example 103, replacing 4-(3-Aminopropyl)morpholine by 1-(3-Aminopropyl)pyrrolidine gave the title compound as its TFA salt; LC/MS(m/e)=560.0, Rt=1.66 min.

Example 106

Preparation of 2,3-Dichloro-N-{4-[1-methyl-6-(3-dimethylamino-propylamino)-1H-pyrazolo[3,4-d]pyrimidin-3-yl]-phenyl}-benzenesulfonamide Following the procedure of Example 103, replacing 4-(3-Aminopropyl)morpholine by N,N-dimethyl-1,3-propanediamine gave the title compound as its TFA salt; LC/MS(m/e)=533.8 ($MH^+$), Rt=1.59 min.

Example 107

Preparation of 2,3-Dichloro-N-{4-[1-methyl-6-(3-diethylamino -propylamino)-1H-pyrazolo[3,4-d]pyrimidin-3-yl]-phenyl}-benzenesulfonamide Following the procedure of Example 103, replacing 4-(3-Aminopropyl)morpholine by N,N-dimethyl-1,3-propanediamine gave the title compound as its TFA salt; LC/MS(m/e)=533.8 ($MH^+$), Rt at 1.59 min.

Example 108

Preparation of 2,3-Dichloro-N-(4-{1-methyl-6-[2-(1-methyl-pyrrolidin-2-yl)-ethylamino]-1H-pyrazolo[3,4-d]pyrimidin-3-yl]-phenyl}-benzenesulfonamide Following the procedure of Example 103, replacing 4-(3-Aminopropyl)morpholine by 2-(2-Aminoethyl)-1-methylpyrrolidine gave the title compound as its TFA salt; LC/MS(m/e)=562.0 ($MH^+$), Rt=1.71 min.

Example 109

Preparation of 2,3-Dichloro-N-(4-{1-methyl-6-[2-(2-oxo-imidazolidin-1-yl)-ethylamino]-1H-pyrazolo[3,4-d]pyrimidin-3-yl]-phenyl}-benzenesulfonamide Following the procedure of Example 103, replacing 4-(3-Aminopropyl)morpholine by 1-(2-Aminoethyl)-2-imidazolidinone gave the title compound as its TFA salt; LC/MS(m/e)=561.0 ($MH^+$), Rt=1.92 min.

Example 110

Preparation of 2,3-Dichloro-N-{4-[1-methyl-6-(4-pyrrolidin 1-yl-butylamino)-1H-pyrazolo[3,4-d]pyrimidin-3-yl]-phenyl}-benzenesulfonamide Following the procedure of Example 103, replacing 4-(3-Aminopropyl)morpholine by 4-Pyrrolidinobutylamine gave the title compound as its TFA salt; LC/MS(m/e)=574.0 ($MH^+$), Rt=1.71 min.

Example 111

Preparation of 2,3-Dichloro-N-(4-{1-methyl-6-[3-(4-methyl-piperazin-1-yl)-propylamino]-1H-pyrazolo[3,4-d]pyrimidin-3-yl]-phenyl}-benzenesulfonamide Following the procedure of Example 103, replacing 4-(3-Aminopropyl)morpholine by 1-(3-Aminopropyl)-4-methylpiperizine gave the title compound as its TFA salt; LC/MS(m/e)=589.0 ($MH^+$), Rt=1.59 min.

Example 112

Preparation of 2,3-Dichloro-N-{4-[1-methyl-6-(3-hydroxy-propylamino)-1H-pyrazolo[3,4-d]pyrimidin-3-yl]-phenyl}-benzenesulfonamide Following the procedure of Example 103, replacing 4-(3-Aminopropyl)morpholine by 3-Amino-1-propanol gave the title compound as its TFA salt; LC/MS(m/e)=507.2 ($MH^+$), Rt=1.81 min.

Example 113

Preparation of 2,3-Dichloro-N-{4-[1-methyl-6-(4-hydroxy-butylamino)-1H-pyrazolo[3,4-d]pyrimidin-3-yl]-phenyl}-benzenesulfonamide Following the procedure of Example 103, replacing 4-(3-Aminopropyl)morpholine by 4-Amino-1-butanol gave the title compound as its TFA salt; LC/MS(m/e)=521.0 ($MH^+$), Rt=1.96 min.

Example 114

Preparation of 2,3-Dichloro-N-{4-[1-methyl-6-(5-hydroxy-pentylamino)-1H-pyrazolo[3,4-d]pyrimidin-3-yl]-phenyl}-benzenesulfonamide Following the procedure of Example 103, replacing 4-(3-Aminopropyl)morpholine by 5-Amino-1-pentanol gave the title compound as its TFA salt; LC/MS(m/e)=535.0 (MH$^+$), Rt=1.99 min.

Example 115

Preparation of 2,3-Dichloro-N-{4-[1-methyl-6-(2-acetylamino-ethylamino)-1H-pyrazolo[3,4-d]pyrimidin-3-yl]-phenyl}-benzenesulfonamide Following the procedure of Example 103, replacing 4-(3-Aminopropyl)morpholine by N-Acetylethylenediamine gave the title compound as its TFA salt; LC/MS(m/e)=533.8 (MH$^+$), Rt=1.90 min.

Example 116

Preparation of 2,3-Dichloro-N-{4-[1-methyl-6-(3-imidazol-1-yl-propylamino)-1H-pyrazolo[3,4-d]pyrimidin-3-yl]-phenyl}-benzenesulfonamide Following the procedure of Example 103, replacing 4-(3-Aminopropyl)morpholine by 1-(3-Aminopropyl)imidazole gave the title compound as its TFA salt; LC/MS(m/e)=556.8 (MH$^+$), Rt=1.6 min.

Example 117

Preparation of 2,3-Dichloro-N-(4-{1-methyl-6-[2-(1-methyl-1H-pyrrol-2-yl)ethylamino]-1H-pyrazolo[3,4-d]pyrimidin-3-yl]-phenyl}-benzenesulfonamide Following the procedure of Example 103, replacing 4-(3-Aminopropyl)morpholine by (2-Aminoethyl)-1-methylpyrrole gave the title compound as its TFA salt; LC/MS(m/e)=556.0 (MH$^+$), Rt=2.35 min.

Example 118

Preparation of 2,3-Dichloro-N-{4-[1-methyl-6-(2-hydroxy-1-hydroxymethyl-ethylamino)-1H-pyrazolo[3,4-d]pyrimidin-3-yl]-phenyl}-benzenesulfonamide Following the procedure of Example 103, replacing 4-(3-Aminopropyl)morpholine by Serinol gave the title compound as its TFA salt; LC/MS(m/e)=523.0 (MH$^+$), Rt=1.67 min.

Example 119

Preparation of 2,3-Dichloro-N-{4-[1-methyl-6-(3-amino-propylamino)-1H-pyrazolo[3,4-d]pyrimidin-3-yl]-phenyl}-benzenesulfonamide Following the procedure of Example 103, replacing 4-(3-Aminopropyl)morpholine by 1,3-Diaminopropane gave the title compound as its TFA salt; LC/MS(m/e)=506.2 (MH$^+$), Rt=1.64 min.

Example 120

Preparation of 2,3-Dichloro-N-{4-[1-methyl-6-(4-amino-butylamino)-1H-pyrazolo[3,4-d]pyrimidin-3-yl]-phenyl}-benzenesulfonamide Following the procedure of Example 103, replacing 4-(3-Aminopropyl)morpholine by 1,4-Diaminobutane gave the title compound as its TFA salt; LC/MS(m/e)=520.0 (MH$^+$), Rt=1.62 min.

Example 121

Preparation of 2,3-Dichloro-N-{4-[1-methyl-6-(4-guanidino-butylamino)-1H-pyrazolo[3,4-d]pyrimidin-3-yl]-phenyl}-benzenesulfonamide Following the procedure of Example 103, replacing 4-(3-Aminopropyl)morpholine by Agmatine gave the title compound as its TFA salt; LC/MS(m/e)=562.0 (MH$^+$), Rt=1.77 min.

Example 122

Preparation of 2,3-Dichloro-N-{4-[1-methyl-6-(4-methanesulfonylamino-butylamino)-1H-pyrazolo[3,4-d]pyrimidin-3-yl]-phenyl}-benzenesulfonamide Following the procedure of Example 96, 2,3-Dichloro-N-{4-[1-methyl-6-(4-amino-butylamino)-1H-pyrazolo[3,4-d]pyrimidin-3-yl]-phenyl}-benzenesulfonamide from Example 120 gave the title compound as its TFA salt; LC/MS(m/e)=597.8 (MH$^+$), Rt=1.99 min.

Example 123

Preparation of [2-Fluoro-4-(1-methyl-6-methylsulfanyl-1H-pyrazolo[3,4-d]pyrimidin-3-yl)-phenyl]-carbamic acid tert-butyl ester Following the procedure of Example 15, 3-Bromo-1-methyl-6-methylsulfanyl-1H -pyrazolo[3,4-d]pyrimidine and [2-Fluoro-4-(4,4,5,5-tetramethyl-[1,3,2]dioxaborolan-2-yl)-phenyl]-carbamic acid tert-butyl ester gave the title compound as an off white solid; LC/MS(m/e) at 390.2 (MH$^+$), Rt=2.56 min.

Example 124

Preparation of [2-Fluoro-4-(1-methyl-6-methylsulfonyl-1H-pyrazolo[3,4-d]pyrimidin-3-yl)-phenyl]-carbamic acid tert-butyl ester Following the procedure of Example 5, [2-Fluoro-4-(1-methyl-6-methylsulfanyl-1H-pyrazolo[3,4-d]pyrimidin-3-yl)-phenyl]-carbamic acid tert-butyl ester was converted to the title compound as a mustard yellow solid; LC/MS(m/e=at 422.8 (MH$^+$), Rt=2.12 min.

Example 125

Preparation of [2-Fluoro-4-(1-methyl-6-methylsulfonyl-1H-pyrazolo[3,4-d]pyrimidin-3-yl)-phenylamine Following the procedure of Example 79, [2-Fluoro-4-(1-methyl-6-methylsulfonyl-1H-pyrazolo[3,4-d]pyrimidin-3-

Example 126

Preparation of 1-(2-Fluoro-5-trifluoromethyl-phenyl)-3-{2-fluoro-4-[1-methyl-6-methanesulfonyl-1H-pyrazolo[3,4-d]pyrimidin-3-yl)-phenyl]} urea Following the procedure of Example 80, [2-Fluoro-4-(1-methyl-6-methylsulfonyl-1H-pyrazolo[3,4-d]pyrimidin-3-yl)-phenylamine was converted the title compound as an off white solid; LC/MS(m/e)=527.0 (MH$^+$), Rt=2.35 min.

Example 127

Preparation of 1-(2-Fluoro-5-trifluoromethyl-phenyl)-3-{2-fluoro-4-[1-methyl-6-(3-morpholin-4-yl-propylamino)-1H-pyrazolo[3,4-d]pyrimidin-3-yl)-phenyl]} urea Following the procedure of Example 81, 1-(2-Fluoro-5-trifluoromethyl-phenyl)-3-{2-fluoro-4-[1-methyl-6-methanesulfonyl-1H-pyrazolo[3,4-d]pyrimidin-3-yl)-phenyl]}urea and 4-(3-Aminopropyl)morpholine gave the title compound as its TFA salt; LC/MS(m/e)=590.8 (MH$^+$), Rt=2.27 min.

Example 128

Preparation of 1-(2-Fluoro-5-trifluoromethyl-phenyl)-3-{2-fluoro-4-[1-methyl-6-(3-(2-methyl-piperidin-1-yl)-propylamino)-1H-pyrazolo[3,4-d]pyrimidin-3-yl)-phenyl]} urea Following the procedure of Example 81, 1-(2-Fluoro-5-trifluoromethyl-phenyl)-3-{2-fluoro-4-[1-methyl-6-methanesulfonyl-1H-pyrazolo[3,4-d]pyrimidin-3-yl)-phenyl]} urea and 1-(3-Aminopropyl)-2-pipecoline gave the title compound as its TFA salt; LC/MS(m/e)=603.2 (MH$^+$), Rt=2.39 min.

Example 129

Preparation of 1-(2-Fluoro-5-trifluoromethyl-phenyl)-3-{2-fluoro-4-[1-methyl-6-(3-diethylamino-propylamino)-1H-pyrazolo[3,4-d]pyrimidin-3-yl)-phenyl]} urea Following the procedure of Example 81, 1-(2-Fluoro-5-trifluoromethyl-phenyl)-3-{2-fluoro-4-[1-methyl-6-methanesulfonyl-1H-pyrazolo[3,4-d]pyrimidin-3-yl)-phenyl]} urea and N,N-Diethyl-1,3-propanediamine gave the title compound as its TFA salt; LC/MS(m/e)=577.0 (MH$^+$), Rt=2.27 min.

Example 130

Preparation of 1-(2-Fluoro-5-trifluoromethyl-phenyl)-3-{2-fluoro-4-[1-methyl-6-(2-(1-methyl-pyrrolidin-2-yl)-ethylamino)-1H-pyrazolo[3,4-d]pyrimidin-3-yl)-phenyl]} urea Following the procedure of Example 81, 1-(2-Fluoro-5-trifluoromethyl-phenyl)-3-{2-fluoro-4-[1-methyl-6-methanesulfonyl-1H-pyrazolo[3,4-d]pyrimidin-3-yl)-phenyl]} urea and 2-(2-Aminoethyl)-1-methylpyrrolidine gave the title compound as its TFA salt; LC/MS(m/e)=575.0 (MH$^+$), Rt=2.2 min.

Example 131

Preparation of 1-(2-Fluoro-5-trifluoromethyl-phenyl)-3-{2-fluoro-4-[1-methyl-6-(3-(4-methyl-piperazin-1-yl)-propylamino)-1H-pyrazolo[3,4-d]pyrimidin-3-yl)-phenyl]} urea Following the procedure of Example 81, 1-(2-Fluoro-5-trifluoromethyl-phenyl)-3-{2-fluoro-4-[1-methyl-6-methanesulfonyl-1H-pyrazolo[3,4-d]pyrimidin-3-yl)-phenyl]} urea and 1-(3-Aminopropyl)-4-methylpiperizine gave the title compound as its TFA salt; LC/MS(m/e)=604.4 (MH$^+$), Rt=1.75 min.

Example 132

Preparation of 1-(2-Fluoro-5-trifluoromethyl-phenyl)-3-{2-fluoro-4-[1-methyl-6-(3-(imidazol-1-yl propylamino)-1H-pyrazolo[3,4-d]pyrimidin-3-yl)-phenyl]} urea Following the procedure of Example 81, 1-(2-Fluoro-5-trifluoromethyl-phenyl)-3-{2-fluoro-4-[1-methyl-6-methanesulfonyl-1H-pyrazolo[3,4-d]pyrimidin-3-yl)-phenyl]} urea and 1-(3-Aminopropyl)imidazole gave the title compound as its TFA salt; LC/MS(m/e)=572.4 (MH$^+$), Rt=1.86 min.

Example 133

Preparation of 1-(5-tert-Butyl-isoxazol-3-yl)-3-{2-fluoro-4-[1-methyl-6-methanesulfonyl-1H-pyrazolo[3,4-d]pyrimidin-3-yl)-phenyl]} urea A mixture of 2-Fluoro-4-(1-methyl-6-methylsulfonyl-1H-pyrazolo[3,4-d]pyrimidin-3-yl)-phenylamine (440 mg, 1.37 mmol), (5-tert-Butyl-isoxazol-3-yl)-carbamic acid phenyl ester(712.4 mg, 2 equiv.) and Et$_3$N (477 µl, 2.5 equiv.) in THF was degassed and refluxed under argon overnight. Solvent was removed on rotavap and the residual was treated with CH$_2$Cl$_2$ (5 ml) and CH$_3$OH(0.5 ml). The product was collected by filtration, washed by CH$_2$Cl$_2$, drying left 260 mg as an off white solid; LC/MS(m/e)=488.2 (MH$^+$), Rt=3.54 min.

Example 134

Preparation of 1-(5-tert-Butyl-isoxazol-3-yl)-3-{2-fluoro-4-[1-methyl-6-(3-morpholin-4-yl-propylamino)-1H-pyrazolo[3,4-d]pyrimidin-3-yl)-phenyl]} urea Following the procedure of Example 81, 1-(5-tert-Butyl-isoxazol-3-yl)-3-{2-fluoro-4-[1-methyl-6-methanesulfonyl-1H-pyrazolo[3,4-d]pyrimidin-3-yl)-phenyl]} urea and 4-(3-Aminopropyl)morpholine gave the title compound as its TFA salt; LC/MS(m/e)=552.4 (MH$^+$), Rt=2.01 min.

Example 135

Preparation of 1-(5-tert-Butyl-isoxazol-3-yl)-3-{2-fluoro-4-[1-methyl-6-(3-(2-methyl-piperidin-1-yl)-propylamino)-1H-pyrazolo[3,4-d]pyrimidin-3-yl)-phenyl]} urea Following the procedure of Example 81, 1-(5-tert-Butyl-isoxazol-3-yl)-3-{2-fluoro-4-[1-methyl-6-methanesulfonyl-1H-pyrazolo[3,4-d]pyrimidin-3-yl)-phenyl]} urea and 1-(3-Aminopropyl)-2-pipecoline gave the title compound as its TFA salt; LC/MS(m/e)=564.2 (MH$^+$), Rt=2.03 min.

Example 136

Preparation of 1-(5-tert-Butyl-isoxazol-3-yl)-3-{2-fluoro-4-[1-methyl-6-(3-diethylamino-propylamino)-1H-pyrazolo[3,4-d]pyrimidin-3-yl)-phenyl]} urea Following the procedure of Example 81, 1-(5-tert-Butyl-isoxazol-3-yl)-3-{2-fluoro-4-[1-methyl-6-methanesulfonyl-1H-pyrazolo[3,4-d]pyrimidin-3-yl)-phenyl]} urea and N,N-Diethyl-1,3-propanediamine gave the title compound as its TFA salt; LC/MS(m/e)=538.4 (MH$^+$), Rt=2.07 min.

Example 137

Preparation of 1-(5-tert-Butyl-isoxazol-3-yl)-3-{2-fluoro-4-[1-methyl-6-(2-(1-methyl-pyrrolidin-2-yl)-ethylamino)-1H-pyrazolo[3,4-d]pyrimidin-3-yl)-phenyl]} urea Following the procedure of Example 81, 1-(5-tert-Butyl-isoxazol-3-yl)-3-{2-fluoro-4-[1-methyl-6-methanesulfonyl-1H-pyrazolo[3,4-d]pyrimidin-3-yl)-phenyl]} urea and 2-(2-Aminoethyl)-1-methylpyrrolidine gave the title compound as its TFA salt; LC/MS(m/e)=536.4 (MH$^+$), Rt=2.0 min.

Example 138

Preparation of 1-(5-tert-Butyl-isoxazol-3-yl)-3-{2-fluoro-4-[1-methyl-6-(3-(4-methyl-piperazin-1-yl)-propylamino)-1H-pyrazolo[3,4-d]pyrimidin-3-yl)-phenyl]} urea Following the procedure of Example 81, 1-(5-tert-Butyl-isoxazol-3-yl)-3-{2-fluoro-4-[1-methyl-6-methanesulfonyl-1H-pyrazolo[3,4-d]pyrimidin-3-yl)-phenyl]} urea and 1-(3-Aminopropyl)-4-methylpiperizine gave the title compound as its TFA salt; LC/MS(m/e)=565.0 (MH$^+$), Rt=1.67 min.

Example 139

Preparation of 1-(5-tert-Butyl-isoxazol-3-yl)-3-{2-fluoro-4-[1-methyl-6-(3-(imidazol-1-yl propylamino)-1H-pyrazolo[3,4-d]pyrimidin-3-yl)-phenyl]} urea Following the procedure of Example 81, 1-(5-tert-Butyl-isoxazol-3-yl)-3-{2-fluoro-4-[1-methyl-6-methanesulfonyl-1H-pyrazolo[3,4-d]pyrimidin-3-yl)-phenyl]} urea and 1-(3-Aminopropyl)imidazole gave the title compound as its TFA salt; LC/MS(m/e)=532.6 (MH$^+$), Rt=1.92 min.

Example 140

Preparation of 1-(2-Fluoro-5-trifluoromethyl-phenyl)-3-{4-[(1-methyl-6-(2-pyridin-4-yl-ethylamino)-1H-pyrazolo[3,4-d]pyrimidin-3-yl]-phenyl]} urea Following the procedure of Example 81, replacing phenethylamine by 4-(2-Aminoethyl)pyridine gave the title compound as its TFA salt; LC/MS(m/e)=551.0 (MH$^+$), Rt=1.91 min.

Example 141

Preparation of 1-(2-Fluoro-5-trifluoromethyl-phenyl)-3-{4-[(1-methyl-6-(2-pyridin-3-yl-ethylamino)-1H-pyrazolo[3,4-d]pyrimidin-3-yl]-phenyl} urea Following the procedure of Example 81, replacing phenethylamine by 3-(2-Aminoethyl)pyridine gave the title compound as its TFA salt; LC/MS(m/e)=551.2 (MH$^+$), Rt=1.84 min.

Example 142

Preparation of 1-(2-Fluoro-5-trifluoromethyl-phenyl)-3-{4-[(1-methyl-6-(2-pyridin-2-yl-ethylamino)-1H-pyrazolo[3,4-d]pyrimidin-3-yl]-phenyl} urea Following the procedure of Example 81, replacing phenethylamine by 2-(2-Aminoethyl)pyridine gave the title compound as its TFA salt; LC/MS(m/e)=551.2 (MH$^+$), Rt=2.05 min.

Example 143

Preparation of 1-(2-Fluoro-5-trifluoromethyl-phenyl)-3-{4-[(1-methyl-6-(pyridin-4-ylmethyl)-amino)-1H-pyrazolo[3,4-d]pyrimidin-3-yl]-phenyl} urea Following the procedure of Example 81, replacing phenethylamine by 4-(Aminomethyl)pyridine gave the title compound as its TFA salt; LC/MS(m/e)=537.0 (MH$^+$), Rt=2.02 min.

Example 144

Preparation of 1-(2-Fluoro-5-trifluoromethyl-phenyl)-3-{4-[(1-methyl-6-(pyridin-3-ylmethyl)-amino)-1H-pyrazolo[3,4-d]pyrimidin-3-yl]-phenyl} urea Following the procedure of Example 81, replacing phenethylamine by 3-(Aminomethyl)pyridine gave the title compound as its TFA salt; LC/MS(m/e)=537.2 (MH$^+$), Rt=2.06 min.

Example 145

Preparation of 1-(2-Fluoro-5-trifluoromethyl-phenyl)-3-{4-[(1-methyl-6-(2-[1H-imidazol-4-yl)-ethylamino)-1H-pyrazolo[3,4-d]pyrimidin-3-yl]-phenyl} urea Following the procedure of Example 81, replacing phenethylamine by Histamine gave the title compound as its TFA salt; LC/MS(m/e)=540.4 (MH$^+$), Rt=1.96 min.

Example 146

Preparation of 1-(2-Fluoro-5-trifluoromethyl-phenyl)-3-{4-[(1-methyl-6-(2-[3-methyl-3H-imidazol-4-yl)-ethylamino)-1H-pyrazolo[3,4-d]pyrimidin-3-yl]-phenyl]} urea Following the procedure of Example 81, replacing phenethylamine by 3-Methylhistamine gave the title compound as its TFA salt; LC/MS(m/e)=554.2 (MH⁺), Rt=2.04 min.

The following compounds were prepared in an analogous manner to the above experimental compounds. All were prepared as the TFA salt.

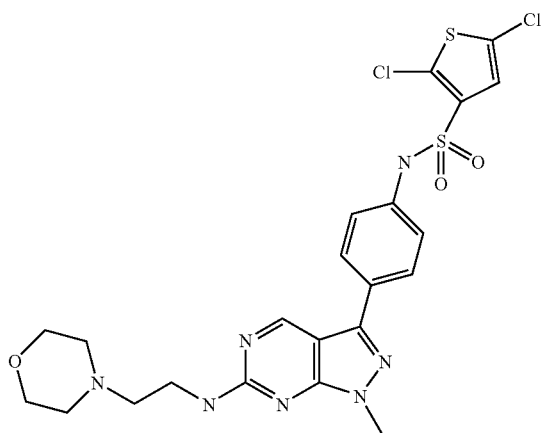

Ex. 149

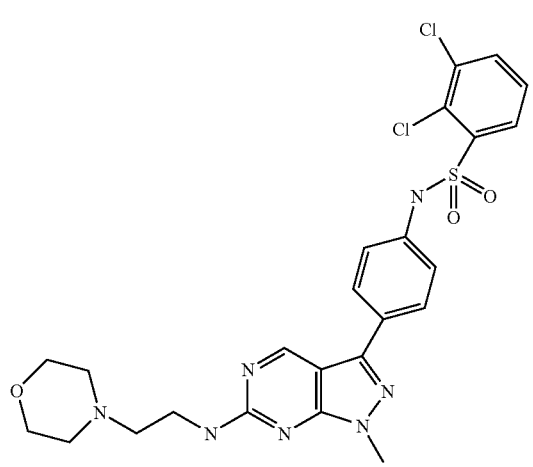

Ex. 147

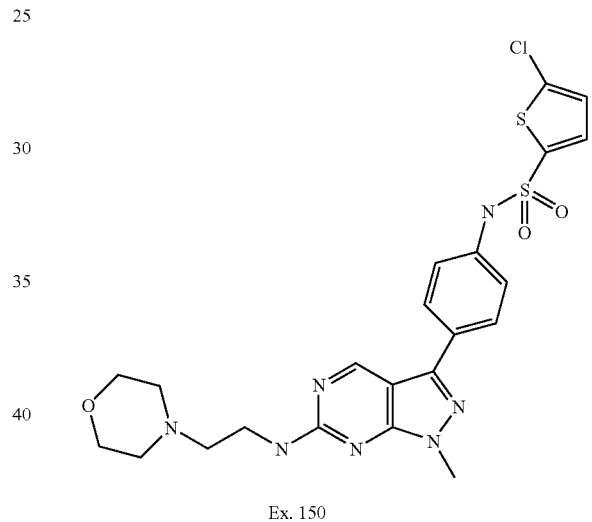

Ex. 150

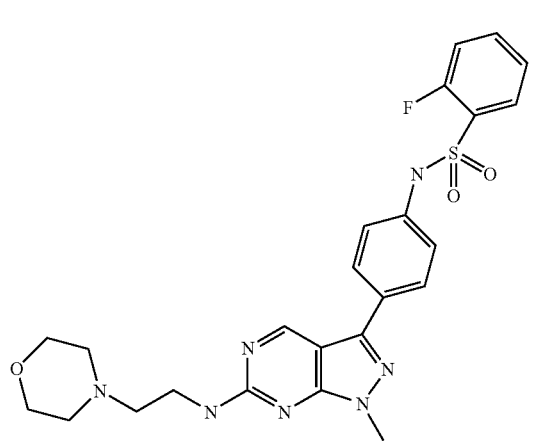

Ex. 148

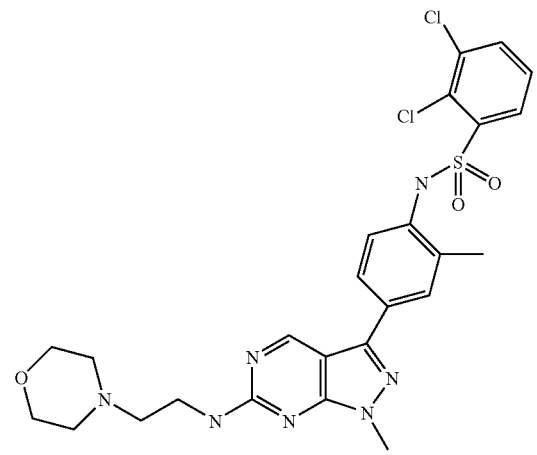

Ex. 151

-continued
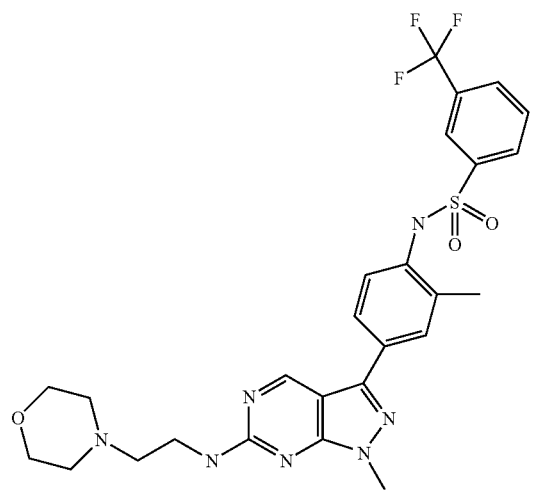
Ex. 152
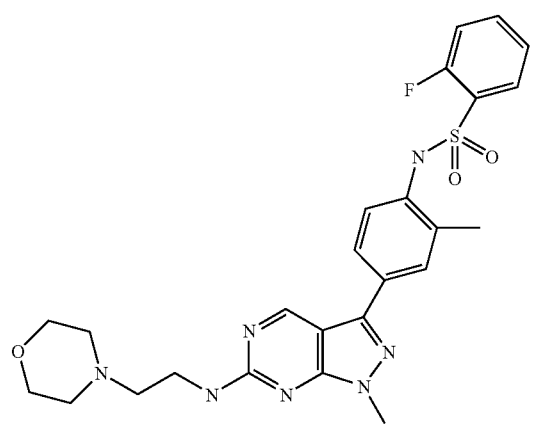
Ex. 153
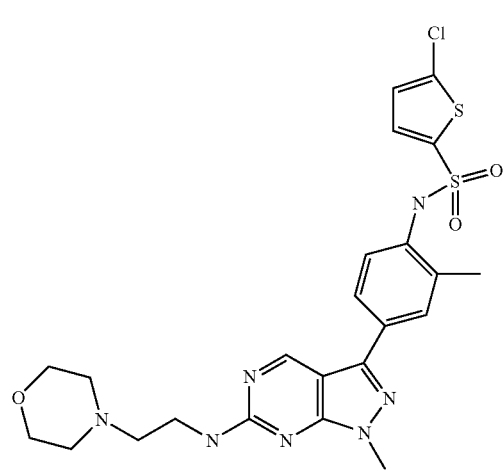
Ex. 154
-continued
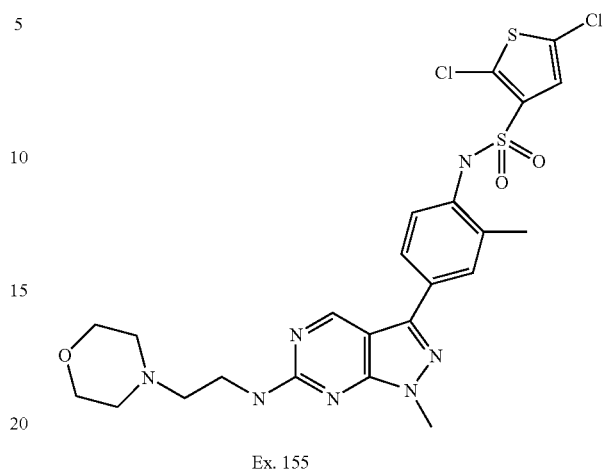
Ex. 155
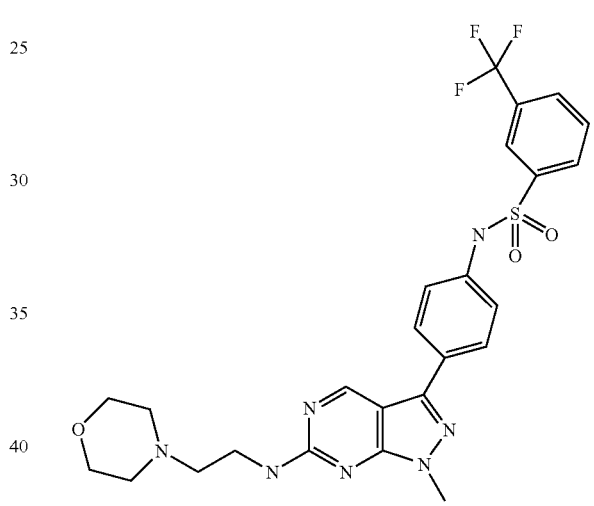
Ex. 156
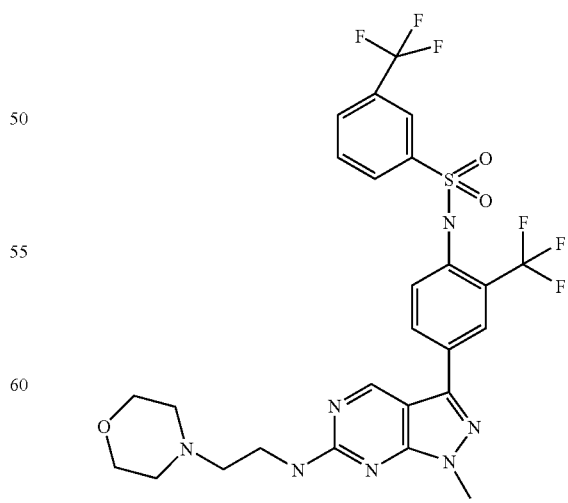
Ex. 157

-continued
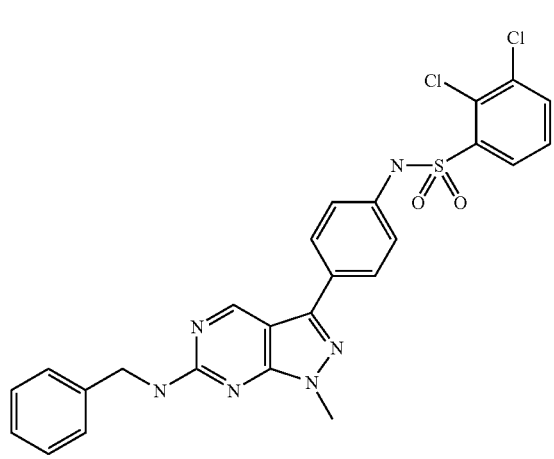
Ex. 158
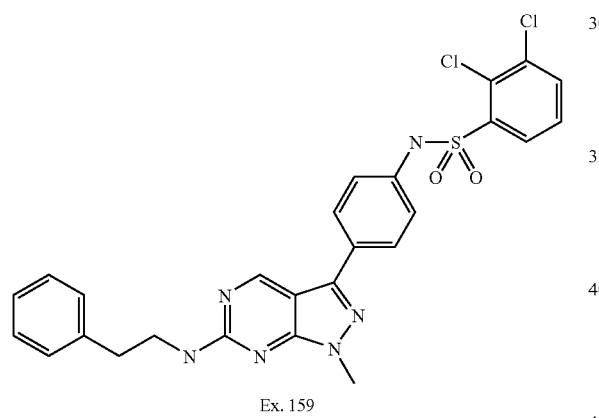
Ex. 159
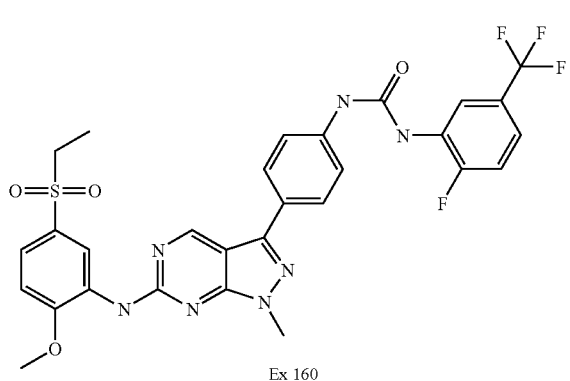
Ex 160
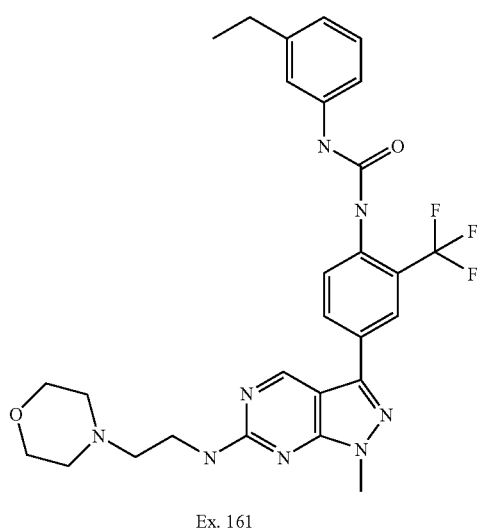
Ex. 161
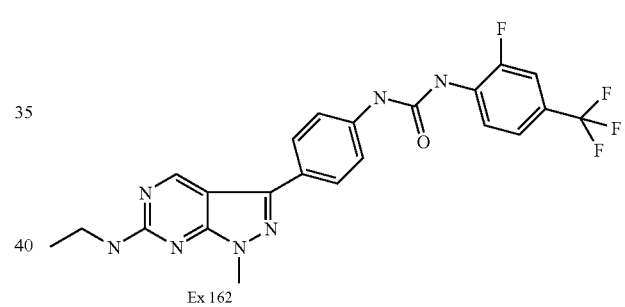
Ex 162
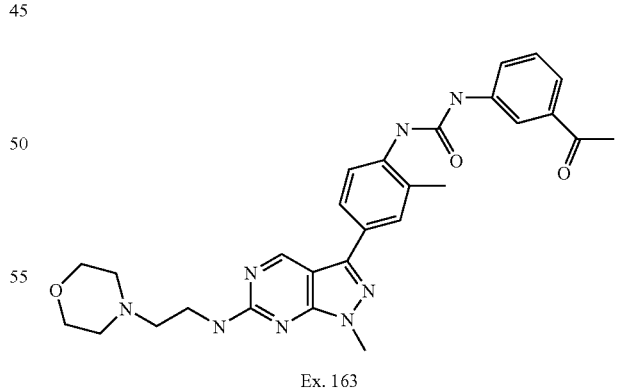
Ex. 163
Biological Data
Compounds are tested for TIE-2 kinase and VEGFR kinase inhibition activity according to one or more of the following methods.

TIE-2 Enzyme Assay (TIE2-E)

The TIE-2 enzyme assay uses the LANCE method (Wallac) and GST-TIE2, baculovirus expressed recombinant constructs of the intracellular domains of human TIE2 (amino acids 762–1104, GenBank Accession # L06139) tagged by GST). The method measures the ability of the purified enzymes to catalyse the transfer of the γ-phosphate from ATP onto tyrosine residues in a biotinylated synthetic peptide, D1–15 (biotin-C6-LEARLVAYEGWVAGKKKamide). This peptide phosphorylation is detected using the following procedure: for enzyme preactivation, GST-TIE2 is incubated for 30 mins at room temperature with 2 mM ATP, 5 mM MgCl2 and 12.5 mM DTT in 22.5 mM HEPES buffer (pH7.4). Preactivated GST-TIE2 is incubated for 30 mins at room temperature in 96 well plates with 1 uM D1–15 peptide, 80 uM ATP, 10 mM MgCl2, 0.1 mg/ml BSA and the test compound (diluted from a 10 mM stock in DMSO, final DMSO concentration is 2.4%) in 1 mM HEPES (pH7.4). The reaction is stopped by the addition of EDTA (final concentration 45 mM). Streptavidin linked-APC (allophycocyanin, Molecular Probe) and Europium-labeled anti-phosphorylated tyrosine antibody (Wallac) are then added at the final concentration of 17 ug/well and 2.1 ug/well, respectively. The APC signal is measured using an ARVO multilabel counter. (Wallac Berthold Japan). The percent inhibition of activity is calculated relative to blank control wells. The concentration of test compound that inhibits 50% of activity ($IC_{50}$) is interpolated using nonlinear regression (Levernberg-Marquardt) and the equation, y=Vmax (1-x/(K+x))+Y2, where "K" is equal to the $IC_{50}$. The $IC_{50}$ values are converted to $pIC_{50}$ values, i.e., $-\log IC_{50}$ in Molar concentration.

TIE-2 Enzyme Assay (TIE2-E2

The TIE-2 enzyme assay uses the LANCE method (Wallac) and GST-TIE2, baculovirus-expressed recombinant constructs of the intracellular domains of human TIE2 (amino acids 762–1104, GenBank Accession # L06139) tagged by GST). The method measures the ability of the purified enzymes to catalyse the transfer of the γ-phosphate from ATP onto tyrosine residues in a biotinylated synthetic peptide, D1–15 (biotin-C6-LEARLVAYEGWVAGKKKamide). This peptide phosphorylation is detected using the following procedure: for enzyme preactivation, GST-TIE2 is incubated for 2 hours at room temperature with 80 μM ATP, 10 mM MgCl2, 0.1 mg/ml BSA, 0.01% Tween 20 and 1 mM DTT in 100 mM HEPES buffer (pH7.4). 5 nM preactivated GST-TIE2 is incubated for 2 hours at room temperature in 96 well plates with 1 uM D1–15 peptide, 80 uM ATP, 10 mM MgCl2, 0.1 mg/ml BSA, 0.01% Tween 20 and titrated test compound (diluted from a 10 mM stock in DMSO, final DMSO concentration is 2.4%) in 100 mM HEPES (pH7.4). The reaction is stopped by the addition of EDTA (final concentration 45 mM). Streptavidin linked-APC (allophycocyanin, PerkinElmer) and europium-labeled anti-phosphotyrosine antibody (PerkinElmer) are then added at the final concentration of 8 nM and 1 nM, respectively. The APC signal is measured using an Wallac Multilabel 1420 counter. (Wallac Berthold Japan). The percent inhibition of activity is calculated relative to blank control wells. The concentration of test compound that inhibits 50% of activity ($IC_{50}$) is interpolated using nonlinear regression (Levernberg-Marquardt) and the equation, y=Vmax (1-x/(K+x))+Y2, where "K" is equal to the $IC_{50}$. The $IC_{50}$ values are converted to $pIC_{50}$ values, i.e., $-\log IC_{50}$ in Molar concentration.

TIE-2 Autophosphorylation Assay (TIE2-C)

The TIE-2 autophosphorylation assay uses an ELISA method and a TIE2 intracellular domain/c-fms extracellular domain (TIE2/c-fms) chimeric protein expressing mouse 3T3 cell line. This assay measures the autophosphorylation level of TIE2 protein expressed in cells. The cells are cultured in 96 well plates and grown in high glucose DMEM containing 10% serum at 37° C. in a humidified 10% CO2, 90% air incubator. On the day of the assay, the serum containing medium is removed from the cells and replaced with serum free medium for one hour. The test compound (diluted from a 10 mM stock in DMSO, final DMSO concentration is 0.1%) is incubated with TIE2/c-fms expressing cells for 30 minutes in serum free DMEM. Intrinsic cellular dephosphorylation of the receptor is blocked by the addition of the tyrosine phosphatase inhibitor, sodium orthovanadate, from a 100 mM aqueous stock to a final concentration of 1 mM. The culture media is removed by aspiration and the cells incubated for 30 to 60 mins on ice with lysis buffer containing 137 mM NaCl, 2 mM EDTA, 10% glycerol, 1 mM sodium ortho vanadate, 1×tyrosine phosphatase inhibitor cocktail (Sigma) and complete protease inhibitor cocktail (Roche) in 20 mM Tris-HCl (pH8.0). The cell extracts are transferred into Rat anti-c-fms antibody (Zymed-clone 12-2d6) (2.5 mg/ml) coated 96 well plates and incubated for 12 hrs at 4 degrees. The extracts are removed by aspiration and the plate, washed in a buffer comprising PBS, 0.05% Tween-20, 0.05% NP-40 and 5% SuperBlock (Pierce) followed by incubation with an HRP (horseradish peroxidase) conjugated anti-phosphotyrosine antibody, (Upstate Biotech) The plates are again washed with the aforementioned wash buffer and the colorimetric HRP substrate, TMB is added. The reaction progresses for 90 seconds and is stopped with the addition of 2M $H_2SO_4$. The optical density at 450 nm derived from HRP catalyzed TMB is measured with a plate reader capable of reading at the appropriate wavelength (e.g. SpectroMax from Molecular Dynamics). The percent inhibition of activity is calculated relative to non-vanadate treated control wells. The concentration of test compound that inhibits 50% of activity ($IC_{50}$) is interpolated using nonlinear regression (Levernberg-Marquardt) and the equation, y=Vmax (1-x/(K+x))+Y2, where "K" is equal to the $IC_{50}$.

Tie2 Fluorescence Polarization Kinase Activity Assay: (TIE2-FP)

Activation of Recombinant Tie2 Activation:

Recombinant GST-Tie2 is activated by incubating the enzyme in 20 mM Tris-HCl, pH 7.5, 12 mM $MgCl_2$, 100 mM NaCl, 20 μM sodium vanidate, 1 mM DTT and 300 μM ATP at room temperature for 2 hours. The activation mixture is then passed through a NAP-25 desalting column (Pharmacia Biotech cat. no. 17-0852-02) to remove the free ATP. The activated enzyme is stored as aliquots at −80° C. in 20 mM Tris-HCl, pH 7.5 and 100 mM NaCl.

Assay Conditions:

The final assay conditions are 50 mM HEPES, pH 7.5, 5% DMSO (when screening compounds), 200 μM ATP, 5 mM $MgCl_2$, 1 mM DTT, 50 μM sodium vanidate, 1 nM activated enzyme, and 200 μM peptide. $IC_{50}$'s of compounds are measured under subsaturating ATP (200 μM) and varying concentrations of activated Tie2 and peptide substrate (RF-WKYEFWR-OH; MW 1873 Da, TFA salt). Panvera Anti-phosphotyrosine antibody (Cat#P2840) and PTK Green Tracer (Cat#P2842) are used to detect the phosphorylated peptide. Polarization is measured on a TECAN Polarion in 138-second cycles for 30 minutes at room temperature. IC$_{50}$'s are then determined from the % polarization using normal calculation methods. The IC$_{50}$ values are converted to pIC$_{50}$ values, i.e., –log IC$_{50}$ in Molar concentration.

VEGF-R2 Enzyme Assay (VEGF-E)

The VEGF enzyme assay uses the LANCE method (Wallac) and GST-VEGFR2, baculovirus expressed recombinant constructs of the intracellular domains of human TIE2 tagged by GST. The method measures the ability of the purified enzymes to catalyse the transfer of the γ-phosphate from ATP onto tyrosine residues in a biotinylated synthetic peptide, (biotin-aminohexyl-EEEEYFELVAKKKK-NH2). This peptide phosphorylation is detected using the following procedure: GST-VEGFR2 is incubated for 40–60 mins at room temperature with 75 uM ATP, 5 mM MgCl2, 0.1 mM DTT, 0.1 mg/mL BSA and the test compound (diluted from a 10 mM stock in DMSO for desired concentration) in 100 mM HEPES buffer. The reaction is stopped by the addition, of EDTA (final concentration 50 mM). Streptavidin linked-APC (allophycocyanin, Molecular Probe) and Europium-labeled anti-phosphorylated tyrosine antibody (Wallac) are then added at the final concentration of 15 nM and 1 nM, respectively. The APC signal is measured using an ARVO multilabel counter (Wallac Berthold, Japan). The percent inhibition of activity is calculated relative to blank control wells. The concentration of test compound that inhibits 50% of activity (IC$_{50}$) is interpolated using nonlinear regression (Levernberg-Marquardt) and the equation, y=V$_{max}$(1–x/(K+x))+Y2, where "K" is equal to the IC$_{50}$. The IC$_{50}$ values are converted to pIC$_{50}$ values, i.e., –log IC$_{50}$ in Molar concentration.

VEGF-R2 Enzyme Assay (VEGF-E2)

The VEGF enzyme assay uses the LANCE method (Wallac) and GST-VEGFR2, baculovirus expressed recombinant constructs of the intracellular domains of human TIE2 tagged by GST. The method measures the ability of the purified enzymes to catalyse the transfer of the γ-phosphate from ATP onto tyrosine residues in a biotinylated synthetic peptide, (biotin-aminohexyl-EEEEYFELVAKKKK-NH2). This peptide phosphorylation is detected using the following procedure: GST-VEGFR2 is incubated for 40–60 mins at room temperature with 75 uM ATP, 5 mM MgCl2, 0.1 mM DTT, 0.1 mg/mL BSA and the test compound (diluted from a 10 mM stock in DMSO for desired concentration) in 100 mM HEPES buffer. The reaction is stopped by the addition of EDTA (final concentration 50 mM). Streptavidin linked-APC (allophycocyanin, Molecular Probe) and Europium-labeled anti-phosphorylated tyrosine antibody (Wallac) are then added at the final concentration of 15 nM and 1 nM, respectively. The APC signal is measured using an ARVO multilabel counter (Wallac Berthold, Japan). The percent inhibition of activity is calculated relative to blank control wells. The concentration of test compound that inhibits 50% of activity (IC$_{50}$) is interpolated using nonlinear regression (Levernberg-Marquardt) and the equation, y=V$_{max}$(1–x/(K+x))+Y2, where "K" is equal to the IC$_{50}$. The IC$_{50}$ values are converted to pIC$_{50}$ values, i.e., –log IC$_{50}$ in Molar concentration.

VEGF-Driven Cellular Proliferation Assay: BrdU Incorporation Assay (VEGF-C)

Human umbilical cord endothelial cells (HUVEC, Clonetics, CC2519) are passaged in Type I collagen-coated 100-mm petridishes in EGM-MV medium (Clonetics, CC3125) at 37C in a humidified 5% CO2, 95% air incubator. (HUVEC passaged more than 6 times in vitro are discarded and not subjected to assaying.) The cells are harvested using trypsin/EDTA, counted using a haemocytometer and plated at 5000 cells/well in a Type I-collagen coated 96-well plate (Becton Dickinson, 354407) in M199 medium (Gibco BRL, 12340-030) containing 5% FBS (Hyclone, A 1115-L) and gentamicin (at 50 ug/ml, Gibco BRL). After incubation overnight at 37° C., the media are replaced with 100 ul of M199 serum-free medium containing compounds at various concentrations with 0.6% DMSO and gentamicin. The compounds are diluted in serum-free M199 medium from 10 mM stock solutions prepared in 100% DMSO. After a 30 min incubation at 37° C., the cells are fed with 100 ul of serum-free M199 medium containing gentamicin, 0.2% culture-grade bovine serum albumin (BSA, Sigma A1993) and 20 ng/ml of VEGF (R&D systems, 293-VE) or 0.6 ng/ml of basic FGF (R&D systems, 233-FB), and cultured at 37° C. for another 24 h. The cells are pulsed with bromodeoxyuridine (BrdU at 10 uM in serum-free M199) at 37° C. for an additional 24 h. The incorporation of BrdU into the proliferating HUVEC are analyzed using BrdU Cell Proliferation ELISA (Roche Molecular Biochemicals, 1647229) according to the manufacturer's protocols. The optical density at 450 nm is measured with a multilabel counter (ARVO SX, Wallac). The percent inhibition of cell growth is calculated relative to blank control wells. The concentration of test compound that inhibits 50% of cell growth (IC$_{50}$) is interpolated using nonlinear regression (Levernberg-Marquardt) and the equation, y=Vmax (1–x/(K+x))+Y2, where "K" is equal to the IC$_{50}$. The IC$_{50}$ values are converted to pIC$_{50}$ values, i.e., –log IC$_{50}$ in Molar concentration.

VEGFR—3-Homogenous Time-Resolved Fluorescence Assay (VEGFR-3-HTRF)

This assay assesses Vascular Endothelial Growth Factor 3 (VEGFR3) tyrosine kinase inhibitory activity in substrate phosphorylation assays. The assay examines the ability of small molecule organic compounds to inhibit the tyrosine phosphorylation of a peptide substrate.

The substrate phosphorylation assays use the VEGFR3 catalytic domain, which is expressed in Sf. 9 insect cells as an amino-terminal GST-tagged fusion protein. The catalytic domain of human VEGFR3 (AA residues #819–1298 based upon GenBank Accession #XM003852) is cloned by PCR from human Placenta Marathon Ready cDNA (Clontech). The PCR product is subcloned into pFastBac1 vector containing an N-terminal GST tag. The resulting pFB/GST/VEGFR3icd vector is used to generate a recombinant baculovirus for protein expression. The VEGFR3 catalytic domain translated sequence is:

```
MSPILGYWKI KGLVQPTRLL LEYLEEKYEE HLYERDEGDK

WRNKKFELGL EFPNLPYYID GDVKLTQSMA IIRYIADKHN

MLGGCPKERA EISMLEGAVL DIRYGVSRIA YSKDFETLKV

DFLSKLPEML KMFEDRLCHK TYLNGDHVTH PDFMLYDALD

VVLYMDPMCL DAFPKLVCFK KRIEAIPQID KYLKSSKYIA

WPLQGWQATF GGGDHPPKSD LLVPRGSPEF KGLPGEVPLE

EQCEYLSYDA SQWEFPRERL HLGRVLGYGA FGKVVEASAF

GIHKGSSCDT VAVKMLKEGA TASEQRALMS ELKILIHIGN

HLNVVNLLGA CTKPQGPLMV IVEFCKYGNL SNFLRAKRDA

FSPCAEKSPE QRGRFRAMVE LARLDRRRPG SSDRVLFARF
```

-continued

```
SKTEGGARRA SPDQEAEDLW LSPLTMEDLV CYSFQVARGM

EFLASRKCIH RDLAARNILL SESDVVKICD FGLARDIYKD

PDYVRKGSAR

LPLKWMAPES IFDKVYTTQS DVWSFGVLLW EIFSLGASPY

PGVQINEEFC QRLRDGTRMR APELATPAIR RIMLNCWSGD

PKARPAFSEL VEILGDLLQG RGLQEEEEVC MAPRSSQSSE

EGSFSQVSTM

ALHIAQADAE DSPPSLQRHS LAARYYNWVS FPGCLARGAE

TRGSSRMKTF EEFPMTPTTY KGSVDNQTDS GMVLASEEFE

QIESRHRQES GFR
```

Autophosphorylation allows enzymes to be fully activated prior to addition to peptide substrates. The assays are performed using enzyme that has been activated by autophosphorylation via preincubation in buffer with ATP and magnesium. Activated enzyme is then diluted and added to titrated compound and the substrate mix.

200 nM VEGFR3 enzyme is activated for 45 minutes at room temperature by incubating the enzyme in buffer containing 100 mM HEPES (pH7.2), 75 µM ATP, 0.3 mM DTT, 0.1 mg/mL BSA, and 10 mM $MgCl_2$. After activation, VEGFR3 is diluted 100-fold into 2× dilution buffer: 200 mM HEPES (pH 7.5), 0.2 mg/mL BSA, 0.6 mM DTT. 20 µL of the diluted enzyme mix is added to 20 µL of 2× substrate mix (150 µM ATP, 20 mM $MgCl_2$, 0.72 µM biotinylated peptide) in the assay plates. Final assay conditions are: 100 mM HEPES (pH 7.2), 75 µM ATP, 10 mM $MgCl_2$, 0.1 mg/mL BSA, 0.3 mM DTT, 0.36 µM biotinylated peptide, and 1 nM VEGFR3 enzyme. Assay plates are incubated for 1.5 hours at room temperature before the addition of 30 µL 100 mM EDTA to the wells to stop the enzymatic reaction. 40 µL/well of HTRF mix are then added to the assay plates for the detection of phosphorylated substrate. Final assay concentrations are: 100 mM HEPES (pH7.2), 0.1 mg/mL BSA, 15 nM streptavidin-labeled allophycocyanin (PerkinElmer), and 1 nM europium-labeled anti-phosphotyrosine antibody (PerkinElmer). Assay plates are left unsealed and are counted in a Wallac Multilabel Counter 1420 (PerkinElmer).

The data for dose responses are plotted as % Control calculated with the data reduction formula 100*(U1–C2)/(C1–C2) versus concentration of compound where U is the unknown value, C1 is the average control value obtained for DMSO, and C2 is the average control value obtained for 0.1M EDTA. Data are fitted to the curve described by: y=((Vmax*x)/(K+x)) where Vmax is the upper asymptote and K is the IC50.

The Experimental compounds (Examples 29–58, 61–68, 70, 71, 77, 78, 81–101, 103–122, 127–132, and 134–163) were tested for TIE2 kinase, VEGFR2 kinase, and/or VEGFR3 kinase activity. Results are shown in Table 1.

TABLE 1

| Example No. | TIE2 PIC50 TIE2-E2 assay | VEGFR2 PIC50 VEGFR-E2 assay | VEGFR3 PIC50 VEGFR-3-HTRF assay | TIE2 IC50 TIE2-FP assay | TIE2 % inhibition (at 10 µM) TIE2-FP assay | TIE2 TIE2-C assay |
|---|---|---|---|---|---|---|
| 29 | | | | | | xx |
| 30 | + | nd | nd | | | |
| 31 | +++ | + | + | | | |
| 32 | +++ | + | + | | | |
| 33 | | nd | nd | x | | |
| 34 | | + | + | | xxx | |
| 35 | +++ | + | ++ | | | |
| 36 | ++ | nd | nd | | | |
| 37 | +++ | -- | + | | | |
| 38 | +++ | nd | nd | | | |
| 39 | ++ | + | + | | | |
| 40 | + | nd | nd | | | |
| 41 | ++ | -- | nd | | | |
| 42 | ++++ | nd | + | | | |
| 43 | +++ | nd | nd | | | |
| 44 | ++ | nd | nd | | | |
| 45 | ++ | nd | nd | | | |
| 46 | ++ | -- | nd | | | |
| 47 | ++ | nd | nd | | | |
| 48 | ++ | nd | nd | | | |
| 49 | ++++ | + | + | | | |
| 50 | | ++ | + | xxx | | |
| 51 | | + | + | | 0 | |
| 52 | | + | + | xx | | |
| 53 | +++ | + | nd | | | |
| 54 | ++ | nd | nd | | | |
| 55 | ++ | -- | nd | | | |
| 56 | + | + | nd | | | |
| 57 | ++++ | + | + | | | xx |
| 58 | + | nd | nd | | | |
| 61 | +++ | ++ | + | | | |
| 62 | + | nd | nd | | | |
| 63 | ++ | nd | nd | | | |
| 64 | ++++ | -- | -- | | | x |
| 65 | + | nd | nd | | | |
| 66 | +++ | -- | -- | | | |
| 67 | + | + | + | | | |
| 68 | ++ | nd | nd | | | |
| 70 | ++ | + | nd | | | |
| 71 | + | + | ++ | | | |
| 77 | ++ | + | + | | | |
| 78 | +++ | + | + | | | x |
| 81 | + | nd | nd | | | |
| 82 | +++ | -- | -- | | | |
| 83 | ++ | -- | nd | | | |
| 84 | ++++ | + | -- | | | x |
| 85 | ++++ | nd | -- | | | x |
| 86 | ++++ | nd | nd | | | |
| 87 | ++++ | nd | nd | | | |
| 88 | ++++ | nd | nd | | | x |
| 89 | ++++ | nd | nd | | | x |
| 90 | +++ | + | + | | | x |
| 91 | ++++ | + | + | | | xx |
| 92 | ++++ | + | + | | | xxx |
| 93 | ++++ | + | + | | | xx |
| 94 | +++ | nd | nd | | | |
| 95 | ++++ | nd | nd | | | |
| 96 | +++ | + | + | | | |
| 97 | +++ | -- | + | | | |
| 98 | ++++ | + | -- | | | |
| 99 | +++ | nd | nd | | | |
| 100 | ++++ | ++ | + | | | x |
| 101 | ++++ | + | + | | | |
| 103 | -- | nd | nd | | | |
| 104 | -- | nd | nd | | | |
| 105 | -- | nd | nd | | | |
| 106 | -- | nd | nd | | | |
| 107 | -- | nd | nd | | | |
| 108 | -- | nd | nd | | | |
| 109 | -- | + | ++ | | | |
| 110 | -- | nd | nd | | | |
| 111 | + | nd | -- | | | |
| 112 | -- | + | + | | | |
| 113 | + | + | + | | | |
| 114 | + | + | + | | | |
| 115 | -- | nd | + | | | |

TABLE 1-continued

| Example No. | TIE2 PIC50 TIE2-E2 assay | VEGFR2 PIC50 VEGFR-E2 assay | VEGFR3 PIC50 VEGFR-3-HTRF assay | TIE2 IC50 TIE2-FP assay | TIE2 % inhibition (at 10 μM) TIE2-FP assay | TIE2-C assay |
|---|---|---|---|---|---|---|
| 116 | -- | nd | -- | | | |
| 117 | nd | nd | + | | | |
| 118 | -- | nd | nd | | | |
| 119 | + | nd | -- | | | |
| 120 | + | nd | nd | | | |
| 121 | + | nd | -- | | | |
| 122 | + | -- | + | | | |
| 127 | ++++ | nd | nd | | | |
| 128 | ++++ | nd | nd | | | |
| 129 | ++++ | nd | nd | | | |
| 130 | ++++ | nd | nd | | | |
| 131 | ++++ | nd | nd | | | |
| 132 | ++++ | + | + | | | |
| 134 | ++++ | -- | nd | | | xx |
| 135 | ++++ | nd | nd | | | x |
| 136 | ++++ | nd | nd | | | x |
| 137 | ++++ | nd | nd | | | x |
| 138 | ++++ | nd | nd | | | xx |
| 139 | ++++ | + | + | | | xx |
| 140 | +++ | nd | ++ | | | |
| 141 | ++ | nd | -- | | | |
| 142 | ++ | nd | nd | | | |
| 143 | ++ | + | -- | | | |
| 144 | ++ | nd | nd | | | |
| 145 | +++ | nd | + | | | x |
| 146 | +++ | nd | ++ | | | x |
| 147 | | nd | nd | | 49 | |
| 148 | | nd | nd | | 36 | |
| 149 | | nd | nd | | 38 | |
| 150 | | nd | nd | | 41 | |
| 151 | -- | nd | nd | | 41 | |
| 152 | | nd | nd | | 13 | |
| 153 | | nd | nd | | 44 | |
| 154 | | nd | nd | | 37 | |
| 155 | | nd | nd | | 23 | |
| 156 | | nd | nd | | 23 | |
| 157 | nd | -- | nd | | 0 | |
| 158 | nd | nd | nd | | | |
| 159 | nd | nd | nd | | | |
| 160 | nd | nd | nd | | | |
| 161 | | | | | | |
| 162 | + | nd | nd | | | |
| 163 | -- | nd | nd | | 25 | | blank = not tested
nd = inconclusive*
-- = PIC50 less than 5.00
+ = PIC50 = 5.00 to less than 6.00
++ = PIC50 = 6.00 to less than 7.00
+++ = PIC50 = 7.00 to less than 7.40
++++ = PIC50 = greater than or equal to 7.40
x = ≧300 nm
xx = ≧100 to ≧300 nm
xxx = <100 nm
*An inconclusive result or null % inhibition is reported where, under the conditions of the assay, no detectable activity is observed. While certain compounds exhibited inconclusive results or null % inhibition under the conditions of the assay, such compounds may exhibit higher and detectable activity under other test conditions.

What is claimed is:

1. A compound selected from:

1-(2-Fluoro-5-trifluoromethyl-phenyl)-3-{4-[(2-hydroxy-ethylamino)-methyl-1H-pyrazolo[3,4-d]pyrimidin-3-yl]-phenyl}-urea;

(Fluoro-trifluoromethyl-phenyl)-carbamic acid 2-(3-{4-[3-(fluoro-trifluoromethyl-phenyl)-ureido]-phenyl}-1-methyl-1-H-pyrazolo[3,4-d]pyrimidin-6-ylamino)-ethyl ester;

1-(2-Fluoro-5-trifluoromethyl-phenyl)-3-{4-[1-methyl-6-(2-morpholin-4-yl-ethylamino-1H -pyrazolo[3,4-d]pyrimidin-3-yl]-phenyl}-urea;

1-(2-Fluoro-5-trifluoromethyl-phenyl)-3-{4-[(2-methoxy-ethylamino)-methyl-1H- pyrazolo3,4-d]pyrimidin-3-yl]-phenyl}-urea;

1-{4-[(2-Diethylamino-ethylamino)-methyl-1H-pyrazolo[3,4-d]pyrimidin-3-yl]-phenyl}-3-(2fluoro-5-trifluoromethyl-phenyl)-urea;

1-{4-[(4-Diethylamino-butylamino)-methyl-1H-pyrazolo[3,4-d]pyrimidin-3-yl]-phenyl}-3-(2-fluoro-5-trifluoromethyl-phenyl)-urea;

1-(5-tert-Butyl-isoxazol-3-yl)-3-{4-[1-methyl-6-(2-morpholin-4-yl-ethylamino)-1H-pyrazolo[3,4-d]]pyrimidin-3-yl]-phenyl}-urea;

1-{4-[1-Methyl-6-(2-morpholin-4-yl-ethylamino)-1H-pyrazolo[3,4-d]pyrimidin-3-yl]-phenyl}-3-(3-trifluoromethyl-phenyl)-thiourea;

1-(Chloro-trifluoromethyl-phenyl)-3-{4-[methyl-(2-morpholin-4-yl-ethylamino)-1H-pyrazolo[3,4-d]pyrimidin-3-yl]-phenyl}-urea;

1-(3-Ethyl-phenyl)-3-{4-[1-methyl-6-(2-morpholin-4-yl-ethylamino)-1H-pyrazolo[3,4d]pyrimidin-3-yl]-phenyl}-urea;

1-{4-[1-Methyl-6-(2-morpholin-4-yl-ethylamino)-1H-pyrazolo[3,4-d]pyrimidin-3-yl]-phenyl}-3-naphthalen-2-yl-urea;

1-(3-Acetyl-phenyl)-3-{4-[1-methyl-6-(2-morpholin-4-yl-ethylamino)-1H-pyrazolo[3,4-d]pyrimidin-3-yl]-phenyl}-urea;

1-(Bis-trifluoromethyl-phenyl)-3-{4-[1-methyl-6-(2-morpholin-4-yl-ethylamino)-1H-pyrazolo[3,4-d]pyrimidin-3-yl]-phenyl}-urea;

1-{4-[1-Methyl-6-(2-morpholin-4-yl-ethylamino)-1H-pyrazolo[3,4-d]pyrimidin-3-yl]-phenyl}-3-(3-trifluoromethyl-phenyl)-urea;

1-(2-Fluoro-5-trifluoromethyl-phenyl)-3-{methyl-[methyl-(2-morpholin-4-yl-ethylamino)-1H-pyrazolo[3,4-d]pyrimidin-3-yl]-phenyl}-urea;

1-(Chloro-trifluoromethyl-phenyl)-3-{methyl-[methyl-(2-morpholin-4-yl-ethylamino)-1H-pyrazolo[3,4-d]pyrimidin-3-yl]-phenyl}-urea;

1-(3-Ethyl-phenyl)-3-{2-methyl-4-[1-methyl-6-(2-morpholin-4-yl-ethylamino)-1H-pyrazolo[3,4-d]pyrimidin-3-yl]-phenyl}-urea;

1-{2-Methyl-4-[1-methyl-6-(2-morpholin-4-yl-ethylamino)-1H-pyrazolo[3,4-d]pyrimidin-3-yl]-phenyl}-3-naphthalen-2-yl-urea;

1-(Bis-trifluoromethyl-phenyl)-3-{methyl-[methyl-(2-morpholin-4-yl-methylamino)-1H-pyrazolo[3,4-d]pyrimidin-3-yl]-phenyl}-urea;

1-{2-Methyl-4-[methyl-(2-morpholin-4-yl-ethylamino)-1H-pyrazolo[3,4-d]pyrimidin-3-yl]-phenyl}-3-(3-trifluoromethyl-phenyl)-urea;

1-{2-Fluoro-]methyl-(2-morpholin-4-yl-ethylamino)-1H-pyrazolo[3,4-d]]pyrimidin-3-yl]-phenyl}-3-(2-fluoro-5-trifluoromethyl-phenyl)-urea;

1-{4-[Benzyl-(2-morpholin-4-yl-ethylamino)-1H-pyrazolo[3,4-d]pyrimidin-3-yl]-phenyl}-3-(fluoro-trifluoromethyl-phenyl)-urea;

1-{4-[Benzyl-(2-morpholin-4-yl-ethylamino)-1H-pyrazolo[3,4-d]pyrimidin-3-yl]-phenyl}-3-(fluoro-trifluoromethyl-phenyl)-thiourea;

1-{4-[Benzyl-(2-morpholin-4-yl-ethylamino)-1H-pyrazolo[3,4-d]pyrimidin-3-yl]-phenyl}-3-(ethyl-phenyl)-urea;

1-(3,5-Bis-trifluoromethyl-phenyl)-3-{2-fluoro-[methyl-(2-morpholin-4-yl-ethylamino)-1H-pyrazolo[3,4-d]pyrimidin-3-yl]-phenyl}-urea;

1-(3-Acetyl-phenyl)-3-{2-fluoro-4-[1-methyl-6-(2-morpholin-4-yl-ethylamino)-1H-pyrazolo[3,4-d]pyrimidin-3-yl]-phenyl}-urea;

1-{2-Fluoro-4-[1-methyl-6-(2-morpholin-4-yl-ethylamino)-1H-pyrazolo[3,4-d]pyrimidin-3-yl]-phenyl]}-3-naphthalen-2-yl-urea;

1-(2-Fluoro-5-trifluoromethyl-phenyl)-3-{[methyl-(2-morpholin-4-yl-ethylamino)-1H-pyrazolo[3,4-d]pyrimidin-3-yl]-(2-trifluoromethyl-phenyl)}-urea;

1-(5-tert-Butyl-isoxazol-3-yl)-3-{2-fluoro-4-[1-methyl-6-(2-morpholin-4-yl-ethylamino)-1H-pyrazolo[3,4-d]]pyrimidin-3-yl]-phenyl}-urea;

1-{2-Methyl-4-[1-methyl-6-(2-morpholin-4-yl-ethylamino)-1H-pyrazolo[3,4-d]-pyrimidin-3-yl]-phenyl}-3-(3-trifluoromethyl-phenyl)-thiourea;

1-(2-fluoro-5-trifluoromethyl-phenyl)-3-(4-{methyl-6-(2-oxopyrrolidin-2-yl)- 1H-pyrazolo[3,4-d]pyrimidin-3-yl}-phenyl)-urea;

1-(2-fluoro-5-trifluoromethyl-phenyl-3-{4-[1-methyl-6-(benzylamino)-1H-pyrazolo[3,4-d]pyrimidin-3-yl]-phenyl}-urea;

1-(2-fluoro-5-trifluoromethyl-phenyl)-3-{4-[1-methyl-6-(3-chloroanilino)-1H-pyrazolo[3,4-d]pyrimidin-3-yl]-phenyl}-urea;

1-(2-fluoro-5-trifluoromethyl-phenyl)-3-(4-methyl-[3-(4-methyl-piperazine-1-yl)-propylamino]1H-pyrazolo[3,4-d]pyrimidin-3-yl]phenyl)-urea;

1-(2-fluoro-5-trifluoromethyl-phenyl)-3-(4-[methyl-(1-methyl-piperidin-4-ylamino]1H-pyrazolo[3,4-d]pyrimidin-3-yl]-phenyl)-urea;

2,5-Dichloro-{4-{1-methyl-6-[3-(4-methyl-piperazin-1-yl)-propylamino]-1H-pyrazolo[3,4-d]pyrimidin-3-yl}-phenyl}-thiophene-3-sulfonamide;

2,3-Dichloro-N-{4-(1-methyl-6-(2-oxopyrrolidin-2-yl)-1H-pyrazolo[3,4-d]pyrimidin-3-yl}-phenyl}-benzenesulfonamide;

2,3-Dichloro-{4-{1-methyl-6-[1-methyl-piperadin-4-ylamino)-propylamino]-1H-pyrazolo[3,4-d]pyrimidin-3-yl}-phenyl}-benzenesulfonamide;

1-(2-fluoro-5-trifluoromethyl-phenyl)-3-{4-]6-acetylamino-1-methyl]-1H-pyrazolo[3,4-d]pyrimidin-3-yl]-phenyl}-urea;

2,3-Dichloro-N-{4-(6-(acylamino)-1-methyl)-1H-pyrazolo[3,4-d]pyrimidin-3-yl}-phenyl}-benzenesulfonamide;

2,3-Dichloro-N-{4-(1-isopropyl-6-(2-morpholin-4-yl-ether)-1H-pyrazolo[3,4-d]pyrimidin-3-yl}-phenyl}-benzenesulfonamide; 1-(2-Fluoro-5-trifluoromethyl-phenyl)-3-{4-[(2-morpholin-4-yl-ethyl)-isopropyl-1H-pyrazolo[3,4-d]pyrimidin-3-yl]-phenyl}-urea;

1-(2-Fluoro-5-trifluoromethyl-phenyl)-3-{4-[(1-methyl-6-phenethylamino)-1H-pyrazolo[3,4-d]pyrimidin-3-yl]-phenyl} urea;

1-(2-Fluoro-5-trifluoromethyl-phenyl)-3-{4-[(1-methyl-6-(5-hydroxy-pentylamino)-1H-pyrazolo[3,4-d]pyrimidin-3-yl]-phenyl} urea;

1-(2-Fluoro-5-trifluoromethyl-phenyl)-3-{4-[(1-methyl-6-(2-hydroxy-1-hydroxymethyl-ethylamino)-1H-pyrazolo[3,4-d]pyrimidin-3-yl]-phenyl} urea;

1-(2-Fluoro-5-trifluoromethyl-phenyl)-3-{4-[(1-methyl-6-(3-morpholin-4-yl-propylamino)-1H-pyrazolo[3,4-d]pyrimidin-3-yl]-phenyl} urea;

1-(2-Fluoro-5-trifluoromethyl-phenyl)-3-{4-[(1-methyl-6-[3-(2-methyl-piperidin-1-yl)-propylamino]-1H-pyrazolo[3,4-d]pyrimidin-3-yl]-phenyl} urea;

1-(2-Fluoro-5-trifluoromethyl-phenyl)-3-{4-[1-methyl-6-(3-pyrrolidin-1-yl)-propylamino]-1H-pyrazolo[3,4-d]pyrimidin-3-yl]phenyl} urea;

1-(2-Fluoro-5-trifluoromethyl-phenyl)-3-{4-[1-methyl-6-(3-dimethylamino-propylamino)-1H-pyrazolo[3,4-d]pyrimidin-3-yl]phenyl} urea;

1-(2-Fluoro-5-trifluoromethyl-phenyl)-3-{4-[1-methyl-6-(3-diethylamino-propylamino)-1H-pyrazolo[3,4-d]pyrimidin-3-yl]phenyl} urea;

1-(2-Fluoro-5-trifluoromethyl-phenyl-3-{4-[1-methyl-6-[2-(1-methyl-pyrrolidin-2-yl)-ethylamino]-1H-pyrazolo[3,4-d]pyrimidin-3-yl]-phenyl} urea;

1-(2-Fluoro-5-trifluoromethyl-phenyl)-3-{4-[1-methyl-6-[2-(2-oxo-imidazolidin-1-yl-ethylamino]-1H-pyrazolo[3,4-d]pyrimidin-3-yl]-phenyl} urea;

1-(2-Fluoro-5-trifluoromethyl-phenyl)-3-{4-[1-methyl-6-[(4-pyrrolidin-1-yl)-butylamino]-1H-pyrazolo[3,4-d]pyrimidin-3-yl]phenyl} urea;

1-(2-Fluoro-5-trifluoromethyl-phenyl)-3-{4-[1-methyl-6-(3-hydroxy-propylamino)-1H-pyrazolo[3,4-d]pyrimidin-3-yl]-phenyl} urea;

1-(2-Fluoro-5-trifluoromethyl-phenyl)-3-{4-[1-methyl-6-(4-hydroxy-butylamino)-1H-pyrazolo[3,4-d]pyrimidin-3-yl]-phenyl} urea;

1-(2-Fluoro-5-trifluoromethyl-phenyl)-3-{4-[1-methyl-6-(3-amino-propylamino)-1H-pyrazolo[3,4-d]pyrimidin-3-yl]-phenyl} urea;

1-(2-Fluoro-5-trifluoromethyl-phenyl)-3-{4-[1-methyl-6-(4-amino-butylamino)-1H-pyrazolo[3,4-d]pyrimidin-3-yl]-phenyl} urea;

N-[3-(3-{4-[3-(2-Fluoro-5-trifluoromethyl-phenyl)-ureido]-phenyl}-1-methyl-1H-pyrazolo[3,4-d]pyrimidin-6-ylamino)-propyl]-methanesulfonamide;

N-[4-(3-{4-[3-(2-Fluoro-5-trifluoromethyl-phenyl)-ureido]-phenyl}-1-methyl-1H-pyrazolo[3,4-d]pyrimidin-6-ylamino)-butyl]-methanesulfonamide;

1-(2-Fluoro-5-trifluoromethyl-phenyl)-3-{4-[1-methyl-6-(2-acetylamino-ethylamino))-1H-pyrazolo[3,4-d]pyrimidin-3-yl]-phenyl} urea;

1-(2-Fluoro-5-trifluoromethyl-phenyl)-3-{4-[1-methyl-6-(4-guanidino-butylamino)-1H-pyrazolo[3,4-d]pyrimidin-3-yl]-phenyl} urea;

1-(2-Fluoro-5-trifluoromethyl-phenyl)-3-{4-[1-methyl-6-(3-imidazol-1-yl-propylamino)-1H-pyrazolo[3,4-d]pyrimidin-3-yl]-phenyl} urea;

1-(2-Fluoro-5-trifluoromethyl-phenyl)-3-{4-]1-methyl-6-(2-[1-methyl-1H-pyrrol-2-yl]-ethylamino)-1H-pyrazolo[3,4-d]pyrimidin-3-yl]-phenyl} urea;

2,3-Dichloro-N-(4-{1-methyl-6-[2-(2-oxo-imidazolidin-1-yl)-ethylamino]-1H-pyrazolo[3,4-d]pyrimidin-3-yl]-phenyl}-benzenesulfonamide;

2,3-Dichloro-N-(4-{1-methyl-6-[3-(4-methyl-piperazin-1-yl)-propylamino]-1H-pyrazolo[3,4-d]pyrimidin-3-yl]-phenyl}-benzenesulfonamide;

2,3-Dichloro-N-{4-[1-methyl-6-(3-hydroxy-propylamino)-1H-pyrazolo[3,4-d]pyrimidin-3-yl]-phenyl}-benzenesulfonamide;

2,3-Dichloro-N-{4-[1-methyl-6-(4-hydroxy-butylamino)-1H-pyrazolo[3,4-d]pyrimidin-3-yl]-phenyl}-benzenesulfonamide;

2,3-Dichloro-N-{4-[1-methyl-6-(5-hydroxy-pentylamino)-1H-pyrazolo[3,4-d]pyrimidin-3-yl]-phenyl)-benzenesulfonamide;

2,3-Dichloro-N-{4-[1-methyl-6-(2-acetylamino-ethylamino)-1H-pyrazolo[3,4-d]pyrimidin-3-yl]-phenyl}-benzenesulfonamide;
2,3-Dichloro-N-(4-{1-methyl-6-[2-(1-methyl-1H-pyrrol-2-yl)ethylamino]-1H-pyrazolo[3,4-d]pyrimidin-3-yl]-phenyl}-benzenesulfonamide;
2,3-Dichloro-N-{4-[1-methyl-6-(3-amino-propylamino)-1H-pyrazolo[3,4-d]pyrimidin-3-yl]-phenyl}-benzenesulfonamide;
2,3-Dichloro-N-{4-[1-methyl-6-(4-amino-butylamino)-1H-pyrazolo[3,4d]pyrimidin-3-yl]-phenyl}-benzenesulfonamide;
2,3-Dichloro-N-{4-[1-methyl-6-(4-guanidino-butylamino)-1H-pyrazolo[3,4-d]pyrimidin-3-yl]-phenyl}-benzenesulfonamide;
2,3-Dichloro-N-{4-[1-methyl-6-(4-methanesulfonylamino-butylamino)-1H-pyrazolo[3,4-d]pyrimidin-3-yl]-phenyl}-benzenesulfonamide;
1-(2-Fluoro-5-trifluoromethyl-phenyl)-3-{2-fluoro-4-[1-methyl-6-(3-morpholin-4-yl-propylamino)-1H-pyrazolo[3,4-d]pyrimidin-3-yl)-phenyl]} urea;
1-(2-Fluoro-5-trifluoromethyl-phenyl)-3-{2-fluoro-4-[1-methyl-6-(3-(2-methyl-piperidin-1-yl)-propylamino)-1H-pyrazolo[3,4-d]pyrimidin-3-yl)-phenyl]} urea;
1-(2-Fluoro-5-trifluoromethyl-phenyl)-3-{2-fluoro-4-[1-methyl-6-(3-diethylamino-propylamino)-1H-pyrazolo[3,4-d]pyrimidin-3-yl)-phenyl]} urea;
1-(2-Fluoro-5-trifluoromethyl-phenyl)-3-{2-fluoro-4-[1-methyl-6-(2-(1-methyl-pyrrolidin-2-yl)-ethylamino)-1H-pyrazolo[3,4-d]pyrimidin-3-yl)-phenyl]} urea;
1-(2-Fluoro-5-trifluoromethyl-phenyl)-3-{2-fluoro-4-[1-methyl-6-(3-(4-methyl-piperazin-1-yl)-propylamino)-1H-pyrazolo[3,4-d]pyrimidin-3-yl)-phenyl]} urea;
1-(2-Fluoro-5-trifluoromethyl-phenyl)-3-{2-fluoro-4-[1-methyl-6-(3-(imidazol-1-yl propylamino)-1H-pyrazolo[3,4-d]pyrimidin-3-yl)-phenyl]} urea;
1-(5-tert-Butyl-isoxazol-3-yl)-3-{2-fluoro-4-[1-methyl-6-(3-morpholin-4-yl-propylamino)-1H-pyrazolo[3,4-d]pyrimidin-3-yl)-phenyl]} urea;
1-(5-tert-Butyl-isoxazol-3-yl)-3-{2-fluoro-4-[1-methyl-6-(3-(2-methyl-piperidin-1-yl)-propylamino)-1H-pyrazolo[3,4-d]pyrimidin-3-yl)-phenyl]} urea;
1-(5-tert-Butyl-isoxazol-3-yl)-3-{2-fluoro-4-[1-methyl-6-(3-diethylamino-propylamino)-1H-pyrazolo[3,4-d]pyrimidin-3-yl)-phenyl[} urea;
1-(5-tert-Butyl-isoxazol-3-yl)-3-{2-fluoro-4-[1-methyl-6-(2-(1-methyl-pyrrolidin-2-yl)-ethylamino)-1H-pyrazolo[3,4-d]pyrimidin-3-yl)-phenyl]} urea;
1-(5-tert-Butyl-isoxazol-3-yl)-3-{2-fluoro-4-[1-methyl-6-(3-(4-methyl-piperazin-1-yl)-propylamino)-1H-pyrazolo[3,4-d]pyrimidin-3-yl)-phenyl]} urea;
1-(5-tert-Butyl-isoxazol-3-yl)-3-{2-fluoro-4-[1-methyl-6-(3-(imidazol-1-ylpropylamino)-1H-pyrazolo[3,4-d]pyrimidin-3-yl)-phenyl]} urea;
1-(2-Fluoro-5-trifluoromethyl-phenyl)-3-{4-[(1-methyl-6-(2-pyridin-4-yl-ethylamino)-1H-pyrazolo[3,4-d]pyrimidin-3-yl]-phenyl} urea;
1-(2-Fluoro-5-trifluoromethyl-phenyl)-3-{4-[(1-methyl-6-(2-pyridin-3-yl-ethylamino)-1H-pyrazolo[3,4-d]pyrimidin-3-yl]-phenyl} urea;
1-(2-Fluoro-5-trifluoromethyl-phenyl)-3-{4-[(1-methyl-6-(2-pyridin-2-yl-ethylamino)-1H-pyrazolo[3,4-d]pyrimidin-3-yl]-phenyl} urea;
1-(2-Fluoro-5-trifluoromethyl-phenyl)-3-{4-[(1-methyl-6-(pyridin-4-ylmethyl)-amino)-1H-pyrazolo[3,4-d]pyrimidin-3-yl]-phenyl} urea;
1-(2-Fluoro-5-trifluoromethyl-phenyl)-3-{4-[(1-methyl-6-(pyridin-3-ylmethyl)-amino)-1H-pyrazolo[3,4-d]pyrimidin-3-yl]-phenyl} urea;
1-Fluoro-5-trifluoromethyl-phenyl)-3-{4-[(1-methyl-6-(2-[1H-imidazol-4-yl)-ethylamino)-1H-pyrazolo[3,4-d]pyrimidin-3-yl]-phenyl} urea; and
1-(2-Fluoro-5-trifluoromethyl-phenyl)-3-{4-[(1-methyl-6-(2-[3-methyl-3H-imidazol-4-yl)-ethylamino)-1H-pyrazolo[3,4-d]pyrimidin-3-yl]-phenyl} urea;
or a salt thereof.

2. A pharmaceutical composition, comprising:
a) a therapeutically effective amount of a compound as claimed in claim 1, or a salt, thereof, and
b) one or more of pharmaceutically acceptable carriers, diluents and excipients,
c) the composition optionally further comprising an additional agent selected from anti-neoplastic agents, agents which inhibit angiogenesis, or a combination thereof.

3. A compound selected from:

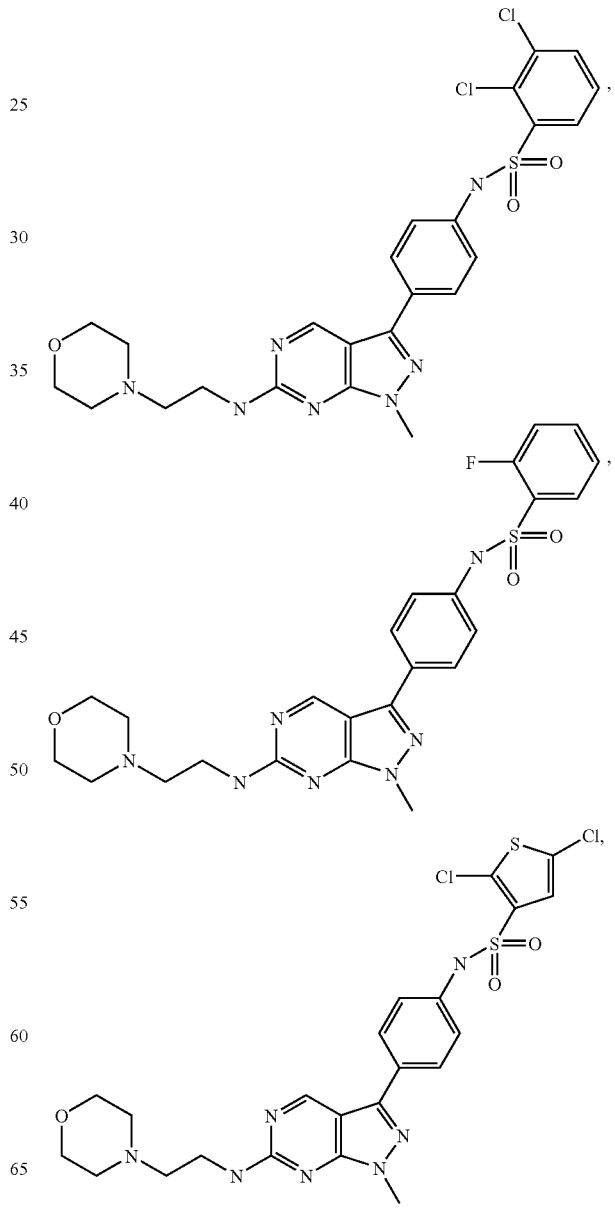

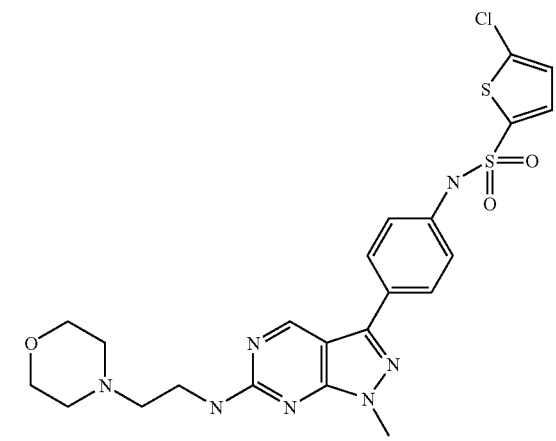
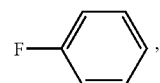
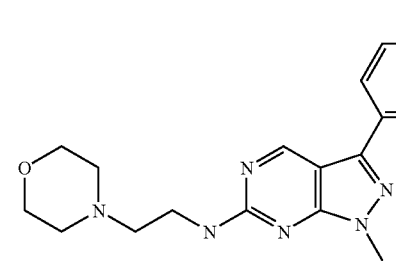
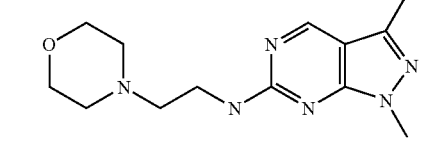
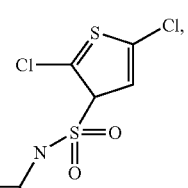
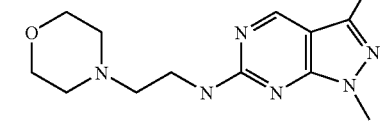
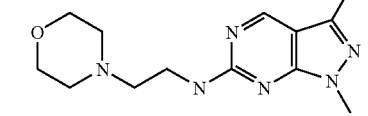

-continued

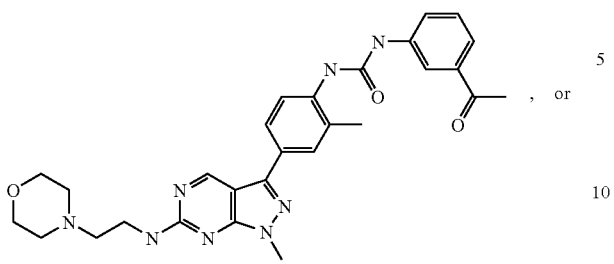

, or salts thereof.

4. A pharmaceutical composition, comprising:
a) a therapeutically effective amount of a compound as claimed in claim 3, or a salt thereof, and
b) one or more of pharmaceutically acceptable carriers, diluents and excipients,
c) the composition optionally further comprising an additional agent selected from anti-neoplastic agents, agents which inhibit angiogenesis, or a combination thereof.

* * * * *